United States Patent
Allain et al.

(10) Patent No.: US 8,343,219 B2
(45) Date of Patent: Jan. 1, 2013

(54) INTERSOMATIC CAGE, INTERVERTEBRAL PROSTHESIS, ANCHORING DEVICE AND IMPLANTATION INSTRUMENTS

(75) Inventors: Jérôme Allain, Bagnolet (FR); Jean Lombard, Niort (FR); Jeff Phelps, North Richland Hills, TX (US); Pierce D. Nunley, Shreveport, LA (US); Charles Gordon, Tyler, TX (US); Vincent J. Leone, Manhasset, NY (US); Michael M. D. Hisey, Flower Mound, TX (US)

(73) Assignee: LDR Medical, Rosières Près Troyes (FR)

( * ) Notice: Subject to any disclaimer, the term of this patent is extended or adjusted under 35 U.S.C. 154(b) by 985 days.

(21) Appl. No.: 12/134,884

(22) Filed: Jun. 6, 2008

(65) Prior Publication Data
US 2009/0105832 A1    Apr. 23, 2009

(30) Foreign Application Priority Data
Jun. 8, 2007    (FR) ..................... 07 04155

(51) Int. Cl.
*A61F 2/44* (2006.01)
*A61F 2/46* (2006.01)
*A61B 17/90* (2006.01)
*A61B 17/92* (2006.01)

(52) U.S. Cl. .................... 623/17.11; 606/86 A; 606/100
(58) Field of Classification Search .................... 606/100
See application file for complete search history.

(56) References Cited

U.S. PATENT DOCUMENTS

| | | |
|---|---|---|
| 566,360 A | 8/1896 | White |
| 1,022,999 A | 4/1912 | Bashaw |
| 1,436,573 A | 11/1922 | Choppinet et al. |
| 1,750,687 A | 3/1930 | Pitkin |
| 2,836,442 A | 5/1958 | Moskovitz |
| 3,325,197 A | 6/1967 | Wehner |

(Continued)

FOREIGN PATENT DOCUMENTS
CA        1304267        6/1992
(Continued)

OTHER PUBLICATIONS

A biological basis for instantaneous centres of rotation of the vertebral column. N. Bouduk, B. Amevo, M. Pearcy, Proc Institution Mechanical Engineers, Jun. 16, 1995, pp. 177-183.

(Continued)

*Primary Examiner* — David H. Willse
(74) *Attorney, Agent, or Firm* — Denko Coburn & Lauff LLP

(57) ABSTRACT

An intersomatic cage, an intervertebral prosthesis, an anchoring device and an instrument for implantation of the cage or the prosthesis and the anchoring device are provided. An intersomatic cage or an intervertebral prosthesis fit closely to the anchoring device, which includes a body of elongated shape on a longitudinal axis, of curved shape describing, along the longitudinal axis, an arc whose dimensions and radius of curvature are designed in such a manner that the anchoring device may be implanted in the vertebral plate of a vertebra by presenting its longitudinal axis substantially along the plane of the intervertebral space, where the anchoring device is inserted, by use of the instrument, through a slot located in at least one peripheral wall of the cage or on at least one plate of the intervertebral disc prosthesis to penetrate into at least one vertebral plate.

46 Claims, 11 Drawing Sheets

U.S. PATENT DOCUMENTS

Figure 2A:
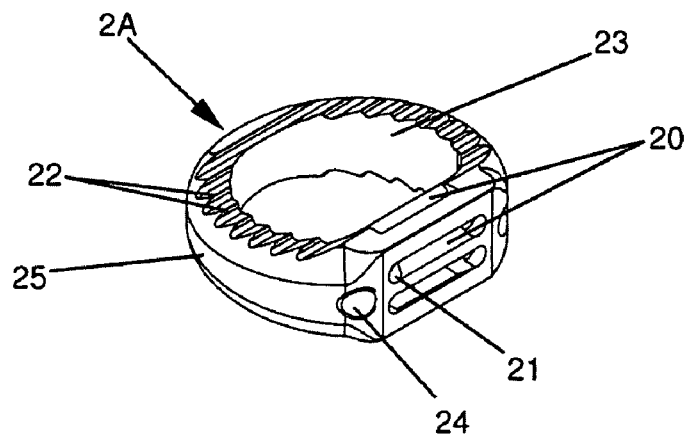

| | | |
|---|---|---|
| 3,374,786 A | 3/1968 | Callender, Jr. |
| 3,486,505 A | 12/1969 | Morrison |
| 3,791,380 A | 2/1974 | Dawidowski |
| 3,857,642 A | 12/1974 | Miller |
| 3,892,232 A | 7/1975 | Neufeld |
| 3,958,278 A | 5/1976 | Lee et al. |
| 4,009,712 A | 3/1977 | Burstein et al. |
| 4,041,939 A | 8/1977 | Hall |
| 4,047,524 A | 9/1977 | Hall |
| 4,055,385 A | 10/1977 | Bjors |
| 4,074,542 A | 2/1978 | Hankosky et al. |
| 4,085,466 A | 4/1978 | Goodfellow et al. |
| 4,135,506 A | 1/1979 | Ulrich |
| 4,175,555 A | 11/1979 | Herbert |
| 4,185,762 A | 1/1980 | Froehlich |
| 4,237,875 A | 12/1980 | Termanini |
| 4,309,777 A | 1/1982 | Patil |
| 4,349,921 A | 9/1982 | Kuntz |
| 4,379,451 A | 4/1983 | Getscher |
| 4,409,974 A | 10/1983 | Freedland |
| 4,429,690 A | 2/1984 | Angelino-Pievani |
| 4,432,358 A | 2/1984 | Fixel |
| 4,488,543 A | 12/1984 | Tornier |
| 4,494,535 A | 1/1985 | Haig |
| 4,519,100 A | 5/1985 | Wills et al. |
| 4,561,432 A | 12/1985 | Mazor |
| 4,599,086 A | 7/1986 | Doty |
| 4,612,920 A | 9/1986 | Lower |
| 4,621,629 A | 11/1986 | Koeneman |
| 4,632,101 A | 12/1986 | Freedland |
| 4,648,388 A | 3/1987 | Steffee |
| 4,653,481 A | 3/1987 | Howland et al. |
| 4,653,489 A | 3/1987 | Tronzo |
| 4,655,778 A | 4/1987 | Koeneman |
| 4,657,001 A | 4/1987 | Fixel |
| 4,664,305 A | 5/1987 | Blake, III et al. |
| 4,696,290 A | 9/1987 | Steffee |
| 4,714,469 A | 12/1987 | Kenna |
| 4,721,103 A | 1/1988 | Freedland |
| 4,756,711 A | 7/1988 | Mai et al. |
| 4,759,352 A | 7/1988 | Lozier |
| 4,759,766 A | 7/1988 | Buettner-Janz et al. |
| 4,759,769 A | 7/1988 | Hedman et al. |
| 4,773,402 A | 9/1988 | Asher et al. |
| 4,787,378 A | 11/1988 | Sodhi |
| 4,787,908 A | 11/1988 | Wyss et al. |
| 4,790,303 A | 12/1988 | Steffee |
| 4,791,918 A | 12/1988 | Von Hasselbach |
| 4,863,476 A | 9/1989 | Shepperd |
| 4,874,389 A | 10/1989 | Downey |
| 4,892,545 A | 1/1990 | Day et al. |
| 4,898,156 A | 2/1990 | Gatturna et al. |
| 4,904,261 A | 2/1990 | Dove et al. |
| 4,911,718 A | 3/1990 | Lee et al. |
| 4,932,975 A | 6/1990 | Main |
| 4,946,378 A | 8/1990 | Hirayama et al. |
| 4,946,458 A | 8/1990 | Harms et al. |
| 4,946,468 A | 8/1990 | Li |
| 4,955,908 A | 9/1990 | Frey et al. |
| 4,955,916 A | 9/1990 | Carignan et al. |
| 4,964,403 A | 10/1990 | Karas et al. |
| 4,968,315 A | 11/1990 | Gatturna |
| 4,969,887 A | 11/1990 | Sodhi |
| 4,973,332 A | 11/1990 | Kummer |
| 4,973,333 A | 11/1990 | Treharne |
| 4,997,432 A | 3/1991 | Keller |
| 5,002,550 A | 3/1991 | Li |
| 5,002,576 A | 3/1991 | Fuhrmann et al. |
| 5,007,880 A | 4/1991 | Walker |
| 5,007,910 A | 4/1991 | Anapliotis et al. |
| 5,024,213 A | 6/1991 | Asher et al. |
| 5,032,125 A | 7/1991 | Durham et al. |
| 5,041,114 A | 8/1991 | Chapman et al. |
| 5,041,116 A | 8/1991 | Wilson |
| 5,041,139 A | 8/1991 | Branemark |
| 5,046,513 A | 9/1991 | Gatturna et al. |
| 5,057,103 A | 10/1991 | Davis |
| 5,062,851 A | 11/1991 | Branemark |
| 5,067,955 A | 11/1991 | Cotrel |
| 5,071,437 A | 12/1991 | Steffee |
| 5,087,266 A | 2/1992 | Connell et al. |
| 5,092,893 A | 3/1992 | Smith |
| 5,098,433 A | 3/1992 | Freedland |
| 5,116,336 A | 5/1992 | Frigg |
| 5,122,130 A | 6/1992 | Keller |
| 5,123,926 A | 6/1992 | Pisharodi |
| 5,129,899 A | 7/1992 | Small et al. |
| 5,129,901 A | 7/1992 | Decoste |
| 5,171,281 A | 12/1992 | Parsons et al. |
| 5,176,680 A | 1/1993 | Vignaud et al. |
| 5,176,681 A | 1/1993 | Lawes et al. |
| 5,192,303 A | 3/1993 | Gatturna et al. |
| 5,192,327 A | 3/1993 | Brantigan |
| 5,197,986 A | 3/1993 | Mikhail |
| 5,207,679 A | 5/1993 | Li |
| 5,217,486 A | 6/1993 | Rice et al. |
| 5,226,766 A | 7/1993 | Lasner |
| 5,234,447 A | 8/1993 | Kaster et al. |
| 5,242,448 A | 9/1993 | Pettine et al. |
| 5,246,458 A | 9/1993 | Graham |
| 5,258,009 A | 11/1993 | Conners |
| 5,258,031 A | 11/1993 | Salib et al. |
| 5,269,784 A | 12/1993 | Mast |
| 5,275,600 A | 1/1994 | Allard et al. |
| 5,282,863 A | 2/1994 | Burton |
| 5,290,312 A | 3/1994 | Kojimoto et al. |
| 5,300,074 A | 4/1994 | Frigg |
| 5,306,307 A | 4/1994 | Senter et al. |
| 5,306,309 A | 4/1994 | Wagner et al. |
| 5,314,477 A | 5/1994 | Marnay |
| 5,324,292 A | 6/1994 | Meyers |
| 5,330,473 A | 7/1994 | Howland |
| 5,342,394 A | 8/1994 | Matsuno et al. |
| 5,344,421 A | 9/1994 | Crook et al. |
| 5,356,410 A | 10/1994 | Pennig |
| 5,356,413 A | 10/1994 | Martins et al. |
| 5,358,526 A | 10/1994 | Tornier |
| 5,370,697 A | 12/1994 | Baumgartner |
| 5,372,599 A | 12/1994 | Martins |
| 5,374,267 A | 12/1994 | Siegal |
| 5,397,364 A | 3/1995 | Kozak et al. |
| 5,401,269 A | 3/1995 | Buttner-Janz et al. |
| 5,417,692 A | 5/1995 | Goble et al. |
| 5,417,712 A | 5/1995 | Whittaker et al. |
| 5,425,772 A | 6/1995 | Brantigan |
| 5,425,773 A | 6/1995 | Boyd et al. |
| 5,429,641 A | 7/1995 | Gotfried |
| 5,437,669 A | 8/1995 | Yuan et al. |
| 5,437,674 A | 8/1995 | Worcel et al. |
| 5,456,698 A | 10/1995 | Byland et al. |
| 5,456,721 A | 10/1995 | Legrand |
| 5,458,601 A | 10/1995 | Young, Jr. et al. |
| 5,458,638 A | 10/1995 | Kuslich et al. |
| 5,472,452 A | 12/1995 | Trott |
| 5,478,342 A | 12/1995 | Kohrs |
| 5,486,174 A | 1/1996 | Fournet-Fayard et al. |
| 5,486,176 A | 1/1996 | Hildebrand et al. |
| 5,489,210 A | 2/1996 | Hanosh |
| 5,501,684 A | 3/1996 | Schlapfer |
| 5,507,754 A | 4/1996 | Green et al. |
| 5,507,816 A | 4/1996 | Bullivant |
| 5,520,689 A | 5/1996 | Schlapfer et al. |
| 5,522,845 A | 6/1996 | Wenstrom, Jr. |
| 5,522,899 A | 6/1996 | Michelson |
| 1,191,676 A | 7/1996 | Di Maggio |
| 5,531,747 A | 7/1996 | Ray |
| 5,531,792 A | 7/1996 | Huene |
| 5,534,004 A | 7/1996 | Santangelo |
| 5,534,029 A | 7/1996 | Shima |
| 5,534,030 A | 7/1996 | Navarro et al. |
| 5,536,268 A | 7/1996 | Griss |
| 5,545,163 A | 8/1996 | Miller et al. |
| 5,545,167 A | 8/1996 | Lin |
| 5,545,229 A | 8/1996 | Parsons et al. |
| 5,549,617 A | 8/1996 | Green et al. |
| 5,554,191 A | 9/1996 | Lahille et al. |
| 5,556,431 A | 9/1996 | Buttner-Janz et al. |

| | | | | | |
|---|---|---|---|---|---|
| 5,562,689 A | 10/1996 | Green et al. | 5,947,966 A | 9/1999 | Drewry et al. |
| 5,562,738 A | 10/1996 | Boyd et al. | 5,951,557 A | 9/1999 | Luter |
| 5,571,104 A | 11/1996 | Li | 5,968,098 A | 10/1999 | Winslow |
| 5,571,109 A | 11/1996 | Bertagnoli | 5,980,522 A | 11/1999 | Koros et al. |
| 5,571,189 A | 11/1996 | Kuslich | 5,984,928 A | 11/1999 | Hermann |
| 5,578,033 A | 11/1996 | Errico et al. | 5,984,967 A | 11/1999 | Zdeblick et al. |
| 5,578,035 A | 11/1996 | Lin | 5,989,250 A | 11/1999 | Wagner et al. |
| 5,582,612 A | 12/1996 | Lin | 5,989,254 A | 11/1999 | Katz |
| 5,584,833 A | 12/1996 | Fournet-Fayard et al. | 5,989,289 A | 11/1999 | Coates et al. |
| 5,584,834 A | 12/1996 | Errico et al. | 6,001,130 A | 12/1999 | Bryan et al. |
| 5,591,166 A | 1/1997 | Bernhardt et al. | 6,010,502 A | 1/2000 | Bagby |
| 5,591,168 A | 1/1997 | Judet et al. | 6,030,389 A | 2/2000 | Wagner et al. |
| 5,593,409 A | 1/1997 | Michelson | 6,033,436 A | 3/2000 | Steinke et al. |
| 5,601,552 A | 2/1997 | Cotrel | 6,033,438 A | 3/2000 | Bianchi et al. |
| 5,603,714 A | 2/1997 | Kaneda et al. | 6,039,763 A | 3/2000 | Shelokov |
| 5,609,592 A | 3/1997 | Brumfield et al. | 6,045,552 A | 4/2000 | Zucherman et al. |
| 5,609,635 A | 3/1997 | Michelson | 6,045,579 A | 4/2000 | Hochshuler et al. |
| 5,609,636 A | 3/1997 | Kohrs et al. | 6,050,997 A | 4/2000 | Mullane et al. |
| 5,613,968 A | 3/1997 | Lin | 6,053,921 A | 4/2000 | Wagner et al. |
| 5,613,974 A | 3/1997 | Andreas et al. | 6,063,088 A | 5/2000 | Winslow |
| 5,620,012 A | 4/1997 | Benderev et al. | 6,063,090 A | 5/2000 | Schlaepfer |
| 5,620,443 A | 4/1997 | Gertzbein et al. | 6,063,121 A | 5/2000 | Xavier et al. |
| 5,628,740 A | 5/1997 | Mullane | 6,066,140 A | 5/2000 | Gertzbein et al. |
| 5,643,321 A | 7/1997 | McDevitt | 6,066,174 A | 5/2000 | Farris |
| 5,645,596 A | 7/1997 | Kim | 6,066,175 A | 5/2000 | Henderson et al. |
| 5,651,789 A | 7/1997 | Cotrel | 6,074,393 A | 6/2000 | Sitoto |
| 5,655,698 A | 8/1997 | Yoon et al. | 6,077,262 A | 6/2000 | Schlapfer et al. |
| 5,674,294 A | 10/1997 | Bainville et al. | 6,080,158 A | 6/2000 | Lin |
| 5,676,701 A | 10/1997 | Yuan et al. | 6,080,193 A | 6/2000 | Hochshuler et al. |
| 5,676,702 A | 10/1997 | Ratron | 6,083,224 A | 7/2000 | Gertzbein et al. |
| 5,683,464 A | 11/1997 | Wagner et al. | 6,093,205 A | 7/2000 | McLeod et al. |
| 5,683,465 A | 11/1997 | Shinn et al. | 6,096,038 A | 8/2000 | Michelson |
| 5,702,449 A | 12/1997 | McKay | 6,096,080 A | 8/2000 | Nicholson et al. |
| 5,702,450 A | 12/1997 | Bisserie | 6,099,531 A | 8/2000 | Bonutti |
| 5,702,472 A | 12/1997 | Huebner | 6,102,950 A | 8/2000 | Vaccaro |
| 5,713,899 A | 2/1998 | Godard | 6,111,164 A | 8/2000 | Rainey et al. |
| 5,722,977 A | 3/1998 | Wilhelmy | 6,113,601 A | 9/2000 | Tatar |
| 5,725,528 A | 3/1998 | Errico et al. | 6,113,637 A | 9/2000 | Gill et al. |
| 5,733,286 A | 3/1998 | Ralph et al. | 6,113,638 A | 9/2000 | Williams et al. |
| 5,735,851 A | 4/1998 | Errico et al. | 6,117,135 A | 9/2000 | Schlapfer |
| 5,738,586 A | 4/1998 | Arriaga | 6,120,502 A | 9/2000 | Michelson |
| 5,741,253 A | 4/1998 | Michelson | 6,123,705 A | 9/2000 | Michelson |
| 5,743,907 A | 4/1998 | Asher et al. | 6,123,706 A | 9/2000 | Lange |
| 5,743,911 A | 4/1998 | Cotrel | 6,129,730 A | 10/2000 | Bono et al. |
| 5,755,798 A | 5/1998 | Papavero et al. | 6,129,763 A | 10/2000 | Chauvin et al. |
| 5,766,252 A | 6/1998 | Henry et al. | 6,132,430 A | 10/2000 | Wagner |
| 5,766,253 A | 6/1998 | Brosnahan, III | 6,136,000 A | 10/2000 | Louis et al. |
| 5,772,661 A | 6/1998 | Michelson | 6,136,002 A | 10/2000 | Shih et al. |
| 5,776,199 A | 7/1998 | Michelson | 6,136,031 A | 10/2000 | Middleton |
| 5,782,830 A | 7/1998 | Farris | 6,143,032 A | 11/2000 | Schafer et al. |
| 5,782,832 A | 7/1998 | Larsen et al. | 6,146,421 A | 11/2000 | Gordon et al. |
| 5,782,833 A | 7/1998 | Haider | 6,146,422 A | 11/2000 | Lawson |
| 5,782,919 A | 7/1998 | Zdeblick et al. | 6,149,650 A | 11/2000 | Michelson |
| 5,797,909 A | 8/1998 | Michelson | 6,156,067 A | 12/2000 | Bryan et al. |
| 5,797,911 A | 8/1998 | Sherman et al. | 6,174,311 B1 | 1/2001 | Branch et al. |
| 5,800,435 A | 9/1998 | Errico et al. | 6,179,873 B1 | 1/2001 | Zientek |
| 5,800,547 A | 9/1998 | Schafer et al. | 6,179,874 B1 | 1/2001 | Cauthen |
| 5,800,550 A | 9/1998 | Sertich | 6,179,875 B1 | 1/2001 | Von Strempel |
| 5,807,403 A | 9/1998 | Beyar et al. | 6,193,757 B1 | 2/2001 | Foley et al. |
| 5,824,094 A | 10/1998 | Serhan et al. | 6,206,879 B1 | 3/2001 | Marnay et al. |
| 5,827,328 A | 10/1998 | Buttermann | 6,206,922 B1 | 3/2001 | Zdeblick et al. |
| 5,833,418 A | 11/1998 | Shoji | 6,206,923 B1 | 3/2001 | Boyd et al. |
| 5,860,973 A | 1/1999 | Michelson | 6,210,412 B1 | 4/2001 | Michelson |
| 5,865,845 A | 2/1999 | Thalgott | 6,214,012 B1 | 4/2001 | Karpman et al. |
| 5,865,848 A | 2/1999 | Baker | 6,214,050 B1 | 4/2001 | Huene |
| 5,876,403 A | 3/1999 | Shitoto | 6,221,077 B1 | 4/2001 | Rinner et al. |
| 5,888,222 A | 3/1999 | Coates et al. | 6,224,595 B1 | 5/2001 | Michelson |
| 5,888,223 A | 3/1999 | Bray | 6,224,607 B1 | 5/2001 | Michelson |
| 5,888,224 A | 3/1999 | Beckers et al. | 6,228,118 B1 | 5/2001 | Gordon |
| 5,888,226 A | 3/1999 | Rogozinski | 6,231,609 B1 | 5/2001 | Mehdizadeh |
| 5,888,227 A | 3/1999 | Cottle | 6,235,034 B1 | 5/2001 | Bray |
| 5,893,889 A | 4/1999 | Harrington | 6,235,059 B1 | 5/2001 | Benezech et al. |
| 5,895,427 A | 4/1999 | Kuslich et al. | 6,241,733 B1 | 6/2001 | Nicholson et al. |
| 5,895,428 A | 4/1999 | Berry | 6,241,769 B1 | 6/2001 | Nicholson et al. |
| 5,899,903 A | 5/1999 | Cotrel | 6,241,770 B1 | 6/2001 | Michelson |
| 5,899,941 A | 5/1999 | Nishijima et al. | 6,245,072 B1 | 6/2001 | Zdeblick et al. |
| 5,910,142 A | 6/1999 | Tatar | 6,245,108 B1 | 6/2001 | Biscup |
| 5,938,663 A | 8/1999 | Petreto | 6,248,104 B1 | 6/2001 | Chopin et al. |
| 5,947,965 A | 9/1999 | Bryan | 6,248,105 B1 | 6/2001 | Schlapfer et al. |

| Patent | Kind | Date | Inventor |
|---|---|---|---|
| 6,251,140 | B1 | 6/2001 | Marino et al. |
| 6,254,603 | B1 | 7/2001 | Gertzbein et al. |
| 6,258,094 | B1 | 7/2001 | Nicholson et al. |
| 6,258,125 | B1 | 7/2001 | Paul et al. |
| 6,261,288 | B1 | 7/2001 | Jackson |
| 6,261,293 | B1 | 7/2001 | Nicholson et al. |
| 6,261,295 | B1 | 7/2001 | Nicholson et al. |
| 6,264,656 | B1 | 7/2001 | Michelson |
| 6,264,658 | B1 | 7/2001 | Lee et al. |
| 6,267,763 | B1 | 7/2001 | Castro |
| 6,267,764 | B1 | 7/2001 | Elberg |
| 6,267,765 | B1 | 7/2001 | Taylor et al. |
| 6,270,498 | B1 | 8/2001 | Michelson |
| 6,277,119 | B1 | 8/2001 | Walulik et al. |
| 6,277,149 | B1 | 8/2001 | Boyle et al. |
| 6,280,445 | B1 | 8/2001 | Morrison et al. |
| 6,283,998 | B1 | 9/2001 | Eaton |
| 6,287,308 | B1 | 9/2001 | Betz et al. |
| 6,287,309 | B1 | 9/2001 | Baccelli et al. |
| 6,296,664 | B1 | 10/2001 | Middleton |
| 6,302,914 | B1 | 10/2001 | Michelson |
| 6,306,136 | B1 | 10/2001 | Baccelli |
| 6,306,170 | B2 | 10/2001 | Ray |
| 6,315,797 | B1 | 11/2001 | Middleton |
| 6,319,257 | B1 | 11/2001 | Carignan et al. |
| 6,344,057 | B1 | 2/2002 | Rabbe et al. |
| 6,348,071 | B1 | 2/2002 | Steffee et al. |
| 6,350,283 | B1 | 2/2002 | Michelson |
| 6,355,038 | B1 | 3/2002 | Pisharodi |
| 6,364,880 | B1 | 4/2002 | Michelson |
| 6,368,350 | B1 | 4/2002 | Erickson et al. |
| 6,371,987 | B1 | 4/2002 | Weiland et al. |
| 6,371,988 | B1 | 4/2002 | Pafford et al. |
| 6,375,655 | B1 | 4/2002 | Zdeblick et al. |
| 6,387,130 | B1 | 5/2002 | Stone et al. |
| 6,391,030 | B1 | 5/2002 | Wagner et al. |
| 6,395,031 | B1 | 5/2002 | Foley et al. |
| 6,395,035 | B2 | 5/2002 | Bresina et al. |
| 6,402,750 | B1 | 6/2002 | Atkinson et al. |
| 6,402,785 | B1 | 6/2002 | Zdeblick et al. |
| 6,409,765 | B1 | 6/2002 | Bianchi et al. |
| 6,413,259 | B1 | 7/2002 | Lyons et al. |
| 6,413,278 | B1 | 7/2002 | Marchosky |
| 6,416,515 | B1 | 7/2002 | Wagner |
| 6,416,551 | B1 | 7/2002 | Keller |
| 6,419,703 | B1 | 7/2002 | Fallin et al. |
| 6,419,704 | B1 | 7/2002 | Ferree |
| 6,419,706 | B1 | 7/2002 | Graf |
| 6,423,063 | B1 | 7/2002 | Bonutti |
| 6,423,095 | B1 | 7/2002 | Van Hoeck et al. |
| 6,432,106 | B1 | 8/2002 | Fraser |
| 6,432,107 | B1 | 8/2002 | Ferree |
| 6,440,168 | B1 | 8/2002 | Cauthen |
| 6,447,512 | B1 | 9/2002 | Landry et al. |
| 6,447,544 | B1 | 9/2002 | Michelson |
| 6,447,546 | B1 | 9/2002 | Bramlet et al. |
| 6,447,547 | B1 | 9/2002 | Michelson |
| 6,454,769 | B2 | 9/2002 | Wagner et al. |
| 6,458,132 | B2 | 10/2002 | Choi |
| 6,458,159 | B1 | 10/2002 | Thalgott |
| 6,461,359 | B1 | 10/2002 | Tribus et al. |
| 6,468,310 | B1 | 10/2002 | Ralph et al. |
| 6,471,704 | B2 | 10/2002 | Gertzbein et al. |
| 6,471,724 | B2 | 10/2002 | Zdeblick et al. |
| 6,475,218 | B2 | 11/2002 | Gournay et al. |
| 6,478,798 | B1 | 11/2002 | Howland |
| 6,478,800 | B1 | 11/2002 | Fraser et al. |
| 6,478,823 | B1 | 11/2002 | Michelson |
| 6,482,233 | B1 | 11/2002 | Aebi et al. |
| 6,482,234 | B1 | 11/2002 | Weber et al. |
| 6,482,584 | B1 | 11/2002 | Mills et al. |
| 6,485,517 | B1 | 11/2002 | Michelson |
| 6,488,682 | B2 | 12/2002 | Kikuchi et al. |
| 6,497,726 | B1 | 12/2002 | Carter et al. |
| 6,500,205 | B1 | 12/2002 | Michelson |
| 6,506,216 | B1 | 1/2003 | McCue et al. |
| 6,514,260 | B1 | 2/2003 | Zdeblick et al. |
| 6,517,580 | B1 | 2/2003 | Ramadan et al. |
| 6,520,967 | B1 | 2/2003 | Cauthen |
| 6,520,996 | B1 | 2/2003 | Manasas et al. |
| 6,524,312 | B2 | 2/2003 | Landry et al. |
| 6,527,804 | B1 | 3/2003 | Gauchet et al. |
| 6,527,806 | B2 | 3/2003 | Ralph et al. |
| 6,540,785 | B1 | 4/2003 | Gill et al. |
| 6,547,790 | B2 | 4/2003 | Harkey, III et al. |
| 6,551,322 | B1 | 4/2003 | Lieberman |
| 6,554,831 | B1 | 4/2003 | Rivard et al. |
| 6,554,863 | B2 | 4/2003 | Paul et al. |
| 6,558,423 | B1 | 5/2003 | Michelson |
| 6,558,424 | B2 | 5/2003 | Thalgott |
| 6,562,040 | B1 | 5/2003 | Wagner |
| 6,565,565 | B1 | 5/2003 | Yuan et al. |
| 6,565,605 | B2 | 5/2003 | Goble et al. |
| 6,572,653 | B1 | 6/2003 | Simonson |
| 6,576,016 | B1 | 6/2003 | Hochshuler et al. |
| 6,579,291 | B1 | 6/2003 | Keith et al. |
| 6,579,319 | B2 | 6/2003 | Goble et al. |
| 6,579,320 | B1 | 6/2003 | Gauchet et al. |
| 6,582,468 | B1 | 6/2003 | Gauchet |
| 6,585,738 | B1 | 7/2003 | Mangione et al. |
| 6,592,624 | B1 | 7/2003 | Fraser et al. |
| 6,595,992 | B1 | 7/2003 | Wagner et al. |
| 6,599,320 | B1 | 7/2003 | Kuslich et al. |
| 6,602,254 | B2 | 8/2003 | Gertzbein et al. |
| 6,605,089 | B1 | 8/2003 | Michelson |
| 6,607,530 | B1 | 8/2003 | Carl et al. |
| 6,607,558 | B2 | 8/2003 | Kuras |
| 6,610,063 | B2 | 8/2003 | Kumar et al. |
| 6,610,065 | B1 | 8/2003 | Branch et al. |
| 6,610,089 | B1 | 8/2003 | Liu et al. |
| 6,610,092 | B2 | 8/2003 | Ralph et al. |
| 6,610,093 | B1 | 8/2003 | Pisharodi |
| 6,613,050 | B1 | 9/2003 | Wagner et al. |
| 6,613,053 | B1 | 9/2003 | Collins et al. |
| 6,613,091 | B1 | 9/2003 | Zdeblick et al. |
| 6,613,278 | B1 | 9/2003 | Mills et al. |
| 6,616,664 | B2 | 9/2003 | Walulik et al. |
| 6,616,671 | B2 | 9/2003 | Landry et al. |
| 6,620,164 | B2 | 9/2003 | Ueyama et al. |
| 6,626,904 | B1 | 9/2003 | Jammet et al. |
| 6,635,086 | B2 | 10/2003 | Lin |
| 6,635,087 | B2 | 10/2003 | Angelucci et al. |
| 6,641,583 | B2 | 11/2003 | Shluzas et al. |
| 6,641,585 | B2 | 11/2003 | Sato et al. |
| 6,641,586 | B2 | 11/2003 | Varieur |
| 6,641,614 | B1 | 11/2003 | Wagner et al. |
| 6,645,206 | B1 | 11/2003 | Zdeblick et al. |
| 6,645,249 | B2 | 11/2003 | Ralph et al. |
| 6,648,893 | B2 | 11/2003 | Dudasik |
| 6,652,533 | B2 | 11/2003 | O'Neil |
| 6,652,584 | B2 | 11/2003 | Michelson |
| 6,652,586 | B2 | 11/2003 | Hunter et al. |
| 6,652,818 | B1 | 11/2003 | Mills et al. |
| 6,656,224 | B2 | 12/2003 | Middleton |
| 6,660,038 | B2 | 12/2003 | Boyer, II et al. |
| 6,663,631 | B2 | 12/2003 | Kuntz |
| 6,666,890 | B2 | 12/2003 | Michelson |
| 6,669,697 | B1 | 12/2003 | Pisharodi |
| 6,669,730 | B2 | 12/2003 | Ralph et al. |
| 6,669,731 | B2 | 12/2003 | Ralph et al. |
| 6,669,732 | B2 | 12/2003 | Serhan et al. |
| 6,673,113 | B2 | 1/2004 | Ralph et al. |
| 6,676,703 | B2 | 1/2004 | Biscup |
| 6,679,887 | B2 | 1/2004 | Nicholson et al. |
| 6,679,915 | B1 | 1/2004 | Cauthen |
| 6,682,530 | B2 | 1/2004 | Dixon et al. |
| 6,682,533 | B1 | 1/2004 | Dinsdale et al. |
| 6,682,562 | B2 | 1/2004 | Viart et al. |
| 6,695,851 | B2 | 2/2004 | Zdeblick et al. |
| 6,695,882 | B2 | 2/2004 | Bianchi et al. |
| 6,702,814 | B2 | 3/2004 | Walulik et al. |
| 6,702,815 | B2 | 3/2004 | Kuntz |
| 6,706,067 | B2 | 3/2004 | Shimp et al. |
| 6,706,068 | B2 | 3/2004 | Ferree |
| 6,709,439 | B2 | 3/2004 | Rogers et al. |
| 6,709,458 | B2 | 3/2004 | Michelson |
| 6,716,247 | B2 | 4/2004 | Michelson |
| 6,719,794 | B2 | 4/2004 | Gerber et al. |

| | | | | | | |
|---|---|---|---|---|---|---|
| 6,723,127 B2 | 4/2004 | Ralph et al. | | 7,090,698 B2 | 8/2006 | Goble et al. |
| 6,723,128 B2 | 4/2004 | Uk | | 7,094,239 B1 | 8/2006 | Michelson |
| 6,726,687 B2 | 4/2004 | Jackson | | 7,105,023 B2 | 9/2006 | Eckman |
| 6,726,720 B2 | 4/2004 | Ross et al. | | 7,105,024 B2 | 9/2006 | Richelsoph |
| 6,730,088 B2 | 5/2004 | Yeh | | 7,112,206 B2 | 9/2006 | Michelson |
| 6,733,504 B2 | 5/2004 | Lin et al. | | 7,118,579 B2 | 10/2006 | Michelson |
| 6,733,531 B1 | 5/2004 | Trieu | | 7,118,580 B1 | 10/2006 | Beyersdorff et al. |
| 6,733,532 B1 | 5/2004 | Gauchet et al. | | 7,118,598 B2 | 10/2006 | Michelson |
| 6,733,535 B2 | 5/2004 | Michelson | | 7,128,760 B2 | 10/2006 | Michelson |
| 6,736,816 B2 | 5/2004 | Ritland | | 7,128,761 B2 | 10/2006 | Kuras et al. |
| 6,736,850 B2 | 5/2004 | Davis | | 7,153,325 B2 | 12/2006 | Kim et al. |
| 6,740,117 B2 | 5/2004 | Ralph et al. | | 7,163,561 B2 | 1/2007 | Michelson |
| 6,740,118 B2 | 5/2004 | Eisermann et al. | | 7,169,153 B2 | 1/2007 | Keller |
| 6,743,255 B2 | 6/2004 | Ferree | | 7,175,662 B2 | 2/2007 | Link et al. |
| 6,743,256 B2 | 6/2004 | Mason | | 7,179,294 B2 | 2/2007 | Eisermann et al. |
| 6,743,257 B2 | 6/2004 | Castro | | 7,198,644 B2 | 4/2007 | Schultz et al. |
| 6,749,613 B1 | 6/2004 | Conchy et al. | | 7,204,851 B2 | 4/2007 | Trieu et al. |
| 6,749,635 B1 | 6/2004 | Bryan | | 7,204,852 B2 | 4/2007 | Marnay et al. |
| 6,749,636 B2 | 6/2004 | Michelson | | 7,211,112 B2 | 5/2007 | Baynham et al. |
| 6,752,832 B2 | 6/2004 | Neumann | | 7,217,291 B2 | 5/2007 | Zucherman et al. |
| 6,755,829 B1 | 6/2004 | Bono et al. | | 7,217,292 B2 | 5/2007 | Ralph et al. |
| 6,755,841 B2 | 6/2004 | Fraser et al. | | 7,217,293 B2 | 5/2007 | Branch, Jr. |
| 6,758,849 B1 | 7/2004 | Michelson | | 7,223,289 B2 | 5/2007 | Trieu et al. |
| 6,764,512 B2 | 7/2004 | Keller | | 7,232,463 B2 | 6/2007 | Falahee |
| 6,764,515 B2 | 7/2004 | Ralph et al. | | 7,232,464 B2 | 6/2007 | Mathieu et al. |
| 6,767,367 B1 | 7/2004 | Michelson | | 7,276,081 B1 | 10/2007 | Coates et al. |
| 6,770,074 B2 | 8/2004 | Michelson | | 7,291,170 B2 | 11/2007 | Huppert |
| 6,770,095 B2 | 8/2004 | Grinberg et al. | | 7,326,248 B2 | 2/2008 | Michelson |
| 6,770,096 B2 | 8/2004 | Bolger et al. | | 7,326,250 B2 | 2/2008 | Beaurain et al. |
| 6,793,678 B2 | 9/2004 | Hawkins | | 7,361,196 B2 | 4/2008 | Fallin et al. |
| 6,793,679 B2 | 9/2004 | Michelson | | 7,410,501 B2 | 8/2008 | Michelson |
| RE38,614 E | 10/2004 | Paul et al. | | 7,419,505 B2 | 9/2008 | Fleischmann et al. |
| 6,800,092 B1 | 10/2004 | Williams et al. | | 7,431,735 B2 | 10/2008 | Liu et al. |
| 6,800,093 B2 | 10/2004 | Nicholson et al. | | 7,435,262 B2 | 10/2008 | Michelson |
| 6,805,713 B1 | 10/2004 | Carter et al. | | 7,442,209 B2 | 10/2008 | Michelson |
| 6,805,714 B2 | 10/2004 | Sutcliffe | | 7,445,635 B2 | 11/2008 | Fallin et al. |
| 6,808,537 B2 | 10/2004 | Michelson | | 7,445,636 B2 | 11/2008 | Michelson |
| 6,814,737 B2 | 11/2004 | Cauthen | | 7,455,692 B2 | 11/2008 | Michelson |
| 6,824,565 B2 | 11/2004 | Muhanna et al. | | 7,465,317 B2 | 12/2008 | Malberg et al. |
| 6,835,206 B2 | 12/2004 | Jackson | | 7,479,160 B2 | 1/2009 | Branch et al. |
| 6,849,093 B2 | 2/2005 | Michelson | | 7,494,508 B2 | 2/2009 | Zeegers |
| 6,884,241 B2 | 4/2005 | Bertranou et al. | | 7,503,933 B2 | 3/2009 | Michelson |
| 6,890,355 B2 | 5/2005 | Michelson | | 7,540,882 B2 | 6/2009 | Michelson |
| 6,899,735 B2 | 5/2005 | Coates et al. | | 7,566,345 B1 | 7/2009 | Fallin et al. |
| 6,902,580 B2 | 6/2005 | Fallin et al. | | 7,588,590 B2 | 9/2009 | Chervitz et al. |
| 6,916,340 B2 | 7/2005 | Metzger et al. | | 7,591,851 B2 | 9/2009 | Winslow et al. |
| 6,923,811 B1 | 8/2005 | Carl et al. | | 7,594,931 B2 | 9/2009 | Louis et al. |
| 6,923,830 B2 | 8/2005 | Michelson | | 7,594,932 B2 | 9/2009 | Aferzon et al. |
| 6,936,071 B1 | 8/2005 | Marnay et al. | | 7,601,170 B2 | 10/2009 | Winslow et al. |
| 6,955,691 B2 | 10/2005 | Chae et al. | | 7,604,654 B2 | 10/2009 | Fallin et al. |
| 6,962,606 B2 | 11/2005 | Michelson | | 7,608,107 B2 | 10/2009 | Michelson |
| 6,964,686 B2 | 11/2005 | Gordon | | 7,618,453 B2 | 11/2009 | Goble et al. |
| 6,964,687 B1 | 11/2005 | Bernard et al. | | 7,618,455 B2 | 11/2009 | Goble et al. |
| 6,966,929 B2 | 11/2005 | Mitchell | | 7,618,456 B2 | 11/2009 | Mathieu et al. |
| 6,972,019 B2 | 12/2005 | Michelson | | 7,621,955 B2 | 11/2009 | Goble et al. |
| 6,972,035 B2 | 12/2005 | Michelson | | 7,621,958 B2 | 11/2009 | Zdeblick et al. |
| 6,981,975 B2 | 1/2006 | Michelson | | 7,625,393 B2 | 12/2009 | Fallin et al. |
| 6,984,234 B2 | 1/2006 | Bray | | 7,632,282 B2 | 12/2009 | Dinville |
| 6,984,245 B2 | 1/2006 | McGahan et al. | | 7,637,951 B2 | 12/2009 | Michelson |
| 6,986,789 B2 | 1/2006 | Schultz et al. | | 7,637,954 B2 | 12/2009 | Michelson |
| 6,994,727 B2 | 2/2006 | Khandkar et al. | | 7,641,690 B2 | 1/2010 | Abdou |
| 7,001,385 B2 | 2/2006 | Bonutti | | 7,655,027 B2 | 2/2010 | Michelson |
| 7,001,432 B2 | 2/2006 | Keller et al. | | 7,658,766 B2 | 2/2010 | Melkent et al. |
| 7,008,453 B1 | 3/2006 | Michelson | | 7,682,396 B2 | 3/2010 | Beaurain et al. |
| 7,011,684 B2 | 3/2006 | Eckman | | 7,695,516 B2 | 4/2010 | Zeegers |
| 7,018,412 B2 | 3/2006 | Ferreira et al. | | 7,695,517 B2 | 4/2010 | Benzel et al. |
| 7,025,787 B2 | 4/2006 | Bryan et al. | | 7,727,280 B2 | 6/2010 | McLuen |
| 7,033,394 B2 | 4/2006 | Michelson | | 7,749,252 B2 | 7/2010 | Zucherman et al. |
| 7,041,135 B2 | 5/2006 | Michelson | | 7,749,274 B2 | 7/2010 | Razian |
| 7,041,136 B2 | 5/2006 | Goble et al. | | 7,753,937 B2 | 7/2010 | Chervitz et al. |
| 7,048,762 B1 | 5/2006 | Sander et al. | | 7,771,473 B2 | 8/2010 | Thramann |
| 7,048,765 B1 | 5/2006 | Grooms et al. | | 7,771,475 B2 | 8/2010 | Michelson |
| 7,056,344 B2 | 6/2006 | Huppert et al. | | 7,776,090 B2 | 8/2010 | Winslow et al. |
| 7,060,097 B2 | 6/2006 | Fraser et al. | | 7,780,670 B2 | 8/2010 | Bonutti |
| 7,060,099 B2 | 6/2006 | Carli et al. | | 7,789,914 B2 | 9/2010 | Michelson |
| 7,063,701 B2 | 6/2006 | Michelson | | 7,794,502 B2 | 9/2010 | Michelson |
| 7,063,702 B2 | 6/2006 | Michelson | | 7,799,053 B2 | 9/2010 | Haid, Jr. et al. |
| 7,066,961 B2 | 6/2006 | Michelson | | 7,799,057 B2 | 9/2010 | Hudgins et al. |
| 7,074,237 B2 | 7/2006 | Goble et al. | | 7,799,081 B2 | 9/2010 | McKinley |

| | | |
|---|---|---|
| 7,811,326 B2 | 10/2010 | Braddock, Jr. et al. |
| 7,819,903 B2 | 10/2010 | Fraser et al. |
| 7,824,445 B2 | 11/2010 | Biro et al. |
| 7,833,255 B2 | 11/2010 | Chow et al. |
| 7,842,088 B2 | 11/2010 | Rashbaum et al. |
| 7,846,207 B2 | 12/2010 | Lechmann et al. |
| 7,850,731 B2 | 12/2010 | Brittan et al. |
| 7,850,732 B2 | 12/2010 | Heinz |
| 7,850,733 B2 | 12/2010 | Baynham et al. |
| 7,862,616 B2 | 1/2011 | Lechmann et al. |
| 7,871,441 B2 | 1/2011 | Eckman |
| 7,875,076 B2 | 1/2011 | Mathieu et al. |
| 7,887,591 B2 | 2/2011 | Aebi et al. |
| 7,892,261 B2 | 2/2011 | Bonutti |
| 7,892,286 B2 | 2/2011 | Michelson |
| 7,909,871 B2 | 3/2011 | Abdou |
| 7,914,560 B2 | 3/2011 | Hoy et al. |
| 7,922,729 B2 | 4/2011 | Michelson |
| 7,931,674 B2 | 4/2011 | Zucherman et al. |
| 7,931,840 B2 | 4/2011 | Michelson |
| 7,935,149 B2 | 5/2011 | Michelson |
| 7,951,198 B2 | 5/2011 | Sucec et al. |
| 7,955,390 B2 | 6/2011 | Fallin et al. |
| 7,972,337 B2 | 7/2011 | Boyajian et al. |
| 7,972,363 B2 | 7/2011 | Moskowitz et al. |
| 7,972,365 B2 | 7/2011 | Michelson |
| 7,976,566 B2 | 7/2011 | Michelson |
| 7,985,255 B2 | 7/2011 | Bray et al. |
| 7,985,258 B2 | 7/2011 | Zdeblick et al. |
| 7,993,373 B2 | 8/2011 | Hoy et al. |
| 7,998,177 B2 | 8/2011 | Hoy et al. |
| 7,998,178 B2 | 8/2011 | Hoy et al. |
| 7,998,211 B2 | 8/2011 | Baccelli et al. |
| 8,002,835 B2 | 8/2011 | Zeegers |
| 8,007,534 B2 | 8/2011 | Michelson |
| 8,021,401 B2 | 9/2011 | Carl et al. |
| 8,021,430 B2 | 9/2011 | Michelson |
| 8,043,334 B2 | 10/2011 | Fisher et al. |
| 8,062,336 B2 | 11/2011 | Triplett et al. |
| 8,062,375 B2 | 11/2011 | Glerum et al. |
| 8,066,741 B2 | 11/2011 | Fallin et al. |
| 8,066,749 B2 | 11/2011 | Winslow et al. |
| 8,070,816 B2 | 12/2011 | Taylor |
| 8,070,819 B2 | 12/2011 | Aferzon et al. |
| 8,075,593 B2 | 12/2011 | Hess |
| 8,075,618 B2 | 12/2011 | Trieu et al. |
| 8,075,621 B2 | 12/2011 | Michelson |
| 8,097,034 B2 | 1/2012 | Michelson |
| 8,114,082 B2 | 2/2012 | Boyajian et al. |
| 8,118,873 B2 | 2/2012 | Humphreys et al. |
| 8,137,405 B2 | 3/2012 | Kostuik et al. |
| 8,147,556 B2 | 4/2012 | Louis et al. |
| 8,167,946 B2 | 5/2012 | Michelson |
| 8,167,949 B2 | 5/2012 | Tyber et al. |
| 8,167,950 B2 | 5/2012 | Aferzon et al. |
| 8,182,539 B2 | 5/2012 | Tyber et al. |
| 8,187,329 B2 | 5/2012 | Theofilos |
| 8,187,332 B2 | 5/2012 | Mcluen |
| 8,216,312 B2 | 7/2012 | Gray |
| 8,241,359 B2 | 8/2012 | Davis et al. |
| 2001/0001119 A1 | 5/2001 | Lombardo |
| 2001/0010000 A1 | 7/2001 | Gertzbein et al. |
| 2001/0018614 A1 | 8/2001 | Bianchi |
| 2001/0020185 A1 | 9/2001 | Ray |
| 2001/0031254 A1 | 10/2001 | Bianchi et al. |
| 2001/0031967 A1 | 10/2001 | Nicholson et al. |
| 2001/0047173 A1 | 11/2001 | Schlapfer et al. |
| 2002/0010467 A1 | 1/2002 | Cooper et al. |
| 2002/0013585 A1 | 1/2002 | Gournay et al. |
| 2002/0016592 A1 | 2/2002 | Branch et al. |
| 2002/0026243 A1 | 2/2002 | Lin |
| 2002/0032483 A1 | 3/2002 | Nicholson et al. |
| 2002/0040243 A1 | 4/2002 | Attali et al. |
| 2002/0072806 A1 | 6/2002 | Buskirk et al. |
| 2002/0082597 A1 | 6/2002 | Fraser |
| 2002/0082700 A1 | 6/2002 | Bianchi et al. |
| 2002/0087212 A1 | 7/2002 | James et al. |
| 2002/0106393 A1 | 8/2002 | Bianchi et al. |
| 2002/0107572 A1 | 8/2002 | Foley et al. |
| 2002/0119437 A1 | 8/2002 | Grooms et al. |
| 2002/0138143 A1 | 9/2002 | Grooms et al. |
| 2002/0143343 A1 | 10/2002 | Castro |
| 2002/0151893 A1 | 10/2002 | Santilli |
| 2002/0161444 A1 | 10/2002 | Choi |
| 2002/0165612 A1 | 11/2002 | Gerber et al. |
| 2002/0165613 A1 | 11/2002 | Lin et al. |
| 2002/0193795 A1 | 12/2002 | Gertzbein et al. |
| 2002/0193880 A1 | 12/2002 | Fraser |
| 2003/0023304 A1 | 1/2003 | Carter et al. |
| 2003/0027125 A1 | 2/2003 | Mills et al. |
| 2003/0028249 A1 | 2/2003 | Baccelli et al. |
| 2003/0045875 A1 | 3/2003 | Bertranou et al. |
| 2003/0055503 A1 | 3/2003 | O'Neil |
| 2003/0060886 A1 | 3/2003 | Van Hoeck et al. |
| 2003/0069586 A1 | 4/2003 | Errico et al. |
| 2003/0069640 A1 | 4/2003 | Ferreira et al. |
| 2003/0074075 A1 | 4/2003 | Thomas, Jr. et al. |
| 2003/0088251 A1 | 5/2003 | Braun et al. |
| 2003/0093153 A1 | 5/2003 | Banick et al. |
| 2003/0093156 A1 | 5/2003 | Metzger et al. |
| 2003/0097179 A1 | 5/2003 | Carter et al. |
| 2003/0100950 A1 | 5/2003 | Moret |
| 2003/0109928 A1 | 6/2003 | Pasquet et al. |
| 2003/0114853 A1 | 6/2003 | Burgess et al. |
| 2003/0135279 A1 | 7/2003 | Michelson |
| 2003/0139815 A1 | 7/2003 | Grooms et al. |
| 2003/0149438 A1 | 8/2003 | Nichols et al. |
| 2003/0167091 A1 | 9/2003 | Scharf |
| 2003/0171814 A1 | 9/2003 | Muhanna et al. |
| 2003/0187436 A1 | 10/2003 | Bolger et al. |
| 2003/0187441 A1 | 10/2003 | Bolger et al. |
| 2003/0187506 A1 | 10/2003 | Ross et al. |
| 2003/0195514 A1 | 10/2003 | Trieu et al. |
| 2003/0195626 A1 | 10/2003 | Huppert |
| 2003/0195629 A1 | 10/2003 | Pafford et al. |
| 2003/0195632 A1 | 10/2003 | Foley et al. |
| 2003/0204260 A1 | 10/2003 | Ferree |
| 2003/0220691 A1 | 11/2003 | Songer et al. |
| 2003/0233145 A1 | 12/2003 | Landry et al. |
| 2003/0233147 A1 | 12/2003 | Nicholson et al. |
| 2004/0002758 A1 | 1/2004 | Landry et al. |
| 2004/0002761 A1 | 1/2004 | Rogers et al. |
| 2004/0010312 A1 | 1/2004 | Enayati |
| 2004/0010316 A1 | 1/2004 | William et al. |
| 2004/0024406 A1 | 2/2004 | Ralph et al. |
| 2004/0030387 A1 | 2/2004 | Landry et al. |
| 2004/0034423 A1 | 2/2004 | Lyons et al. |
| 2004/0073307 A1 | 4/2004 | Keller |
| 2004/0073309 A1 | 4/2004 | Bianchi et al. |
| 2004/0073311 A1 | 4/2004 | Ferree |
| 2004/0073313 A1 | 4/2004 | Link et al. |
| 2004/0083000 A1 | 4/2004 | Keller et al. |
| 2004/0093082 A1 | 5/2004 | Ferree |
| 2004/0093083 A1 | 5/2004 | Branch et al. |
| 2004/0097929 A1 | 5/2004 | Branch et al. |
| 2004/0102846 A1 | 5/2004 | Keller et al. |
| 2004/0111160 A1 | 6/2004 | Evans et al. |
| 2004/0115172 A1 | 6/2004 | Bianchi et al. |
| 2004/0117022 A1 | 6/2004 | Marnay et al. |
| 2004/0127990 A1 | 7/2004 | Bartish, Jr. et al. |
| 2004/0127993 A1 | 7/2004 | Kast et al. |
| 2004/0127994 A1 | 7/2004 | Kast et al. |
| 2004/0133278 A1 | 7/2004 | Marino et al. |
| 2004/0133281 A1 | 7/2004 | Khandkar et al. |
| 2004/0143332 A1 | 7/2004 | Krueger et al. |
| 2004/0148029 A1 | 7/2004 | Bianchi et al. |
| 2004/0153157 A1 | 8/2004 | Keller |
| 2004/0158251 A1 | 8/2004 | Morrison et al. |
| 2004/0158254 A1 | 8/2004 | Eisermann |
| 2004/0158328 A1 | 8/2004 | Eisermann |
| 2004/0162617 A1 | 8/2004 | Zucherman et al. |
| 2004/0172020 A1 | 9/2004 | Beaurain et al. |
| 2004/0172130 A1 | 9/2004 | Nakahara et al. |
| 2004/0193273 A1 | 9/2004 | Huang |
| 2004/0199254 A1 | 10/2004 | Louis et al. |
| 2004/0210219 A1 | 10/2004 | Bray |
| 2004/0210308 A1 | 10/2004 | Carter et al. |
| 2004/0210313 A1 | 10/2004 | Michelson |

| Pub. No. | Date | Inventor |
|---|---|---|
| 2004/0220582 A1 | 11/2004 | Keller |
| 2004/0225295 A1 | 11/2004 | Zubok et al. |
| 2004/0225363 A1 | 11/2004 | Richelsoph |
| 2004/0225364 A1 | 11/2004 | Richelsoph |
| 2004/0230306 A1 | 11/2004 | Hoeck et al. |
| 2004/0243238 A1 | 12/2004 | Arnin et al. |
| 2004/0243240 A1 | 12/2004 | Beaurain et al. |
| 2004/0254577 A1 | 12/2004 | Delecrin et al. |
| 2004/0254643 A1 | 12/2004 | Jackson |
| 2005/0004672 A1 | 1/2005 | Pafford et al. |
| 2005/0010215 A1 | 1/2005 | Delecrin et al. |
| 2005/0015094 A1 | 1/2005 | Keller |
| 2005/0015095 A1 | 1/2005 | Keller |
| 2005/0015149 A1 | 1/2005 | Michelson |
| 2005/0021042 A1 | 1/2005 | Marnay et al. |
| 2005/0027359 A1 | 2/2005 | Mashburn |
| 2005/0027360 A1 | 2/2005 | Webb et al. |
| 2005/0027363 A1 | 2/2005 | Gordon |
| 2005/0033305 A1 | 2/2005 | Schultz |
| 2005/0033428 A1 | 2/2005 | Keller |
| 2005/0033435 A1 | 2/2005 | Belliard et al. |
| 2005/0033437 A1 | 2/2005 | Bao et al. |
| 2005/0033438 A1 | 2/2005 | Schultz |
| 2005/0038511 A1 | 2/2005 | Martz et al. |
| 2005/0038512 A1 | 2/2005 | Michelson |
| 2005/0043798 A1 | 2/2005 | Eckman |
| 2005/0043800 A1 | 2/2005 | Paul et al. |
| 2005/0043804 A1 | 2/2005 | Gordon et al. |
| 2005/0049590 A1 | 3/2005 | Alleyne et al. |
| 2005/0060034 A1 | 3/2005 | Berry et al. |
| 2005/0060037 A1 | 3/2005 | Michelson |
| 2005/0065608 A1 | 3/2005 | Michelson |
| 2005/0065611 A1 | 3/2005 | Huppert et al. |
| 2005/0071009 A1 | 3/2005 | Muhanna et al. |
| 2005/0085911 A1 | 4/2005 | Link |
| 2005/0085917 A1 | 4/2005 | Marnay et al. |
| 2005/0096742 A1 | 5/2005 | Mills et al. |
| 2005/0096745 A1 | 5/2005 | Andre et al. |
| 2005/0100862 A1 | 5/2005 | Mills et al. |
| 2005/0101957 A1 | 5/2005 | Buskirk et al. |
| 2005/0107788 A1 | 5/2005 | Beaurain et al. |
| 2005/0113926 A1 | 5/2005 | Zucherman et al. |
| 2005/0119665 A1 | 6/2005 | Keller |
| 2005/0119744 A1 | 6/2005 | Buskirk et al. |
| 2005/0119747 A1 | 6/2005 | Fabris Monterumici et al. |
| 2005/0131542 A1 | 6/2005 | Benzel et al. |
| 2005/0131544 A1 | 6/2005 | Kuras et al. |
| 2005/0143733 A1* | 6/2005 | Petit ............................ 606/60 |
| 2005/0143824 A1 | 6/2005 | Richelsoph et al. |
| 2005/0143825 A1 | 6/2005 | Enayati |
| 2005/0149189 A1 | 7/2005 | Mokhtar et al. |
| 2005/0154462 A1 | 7/2005 | Zucherman et al. |
| 2005/0159818 A1 | 7/2005 | Blain |
| 2005/0165408 A1 | 7/2005 | Puno et al. |
| 2005/0165483 A1 | 7/2005 | Ray, III et al. |
| 2005/0165486 A1 | 7/2005 | Trieu |
| 2005/0171554 A1 | 8/2005 | Estes et al. |
| 2005/0171610 A1 | 8/2005 | Humphreys et al. |
| 2005/0192671 A1 | 9/2005 | Bao et al. |
| 2005/0197705 A1 | 9/2005 | Arnin et al. |
| 2005/0197706 A1 | 9/2005 | Hovorka et al. |
| 2005/0216086 A1 | 9/2005 | Marik et al. |
| 2005/0216092 A1 | 9/2005 | Marik et al. |
| 2005/0228500 A1 | 10/2005 | Kim et al. |
| 2005/0234553 A1 | 10/2005 | Gordon |
| 2005/0240273 A1 | 10/2005 | Khandkar et al. |
| 2005/0246024 A1 | 11/2005 | Zeegers |
| 2005/0251260 A1 | 11/2005 | Gerber et al. |
| 2005/0256579 A1 | 11/2005 | Keller et al. |
| 2005/0267581 A1 | 12/2005 | Marnay et al. |
| 2005/0273171 A1 | 12/2005 | Gordon et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0278026 A1 | 12/2005 | Gordon et al. |
| 2005/0283242 A1 | 12/2005 | Zucherman et al. |
| 2005/0283244 A1 | 12/2005 | Gordon et al. |
| 2005/0283245 A1 | 12/2005 | Gordon et al. |
| 2005/0283247 A1 | 12/2005 | Gordon et al. |
| 2005/0283248 A1 | 12/2005 | Gordon et al. |
| 2005/0288788 A1 | 12/2005 | Dougherty-Shah |
| 2006/0015183 A1 | 1/2006 | Gilbert et al. |
| 2006/0016768 A1 | 1/2006 | Grichar et al. |
| 2006/0020341 A1 | 1/2006 | Schneid et al. |
| 2006/0030860 A1 | 2/2006 | Peterman |
| 2006/0036261 A1 | 2/2006 | McDonnell |
| 2006/0036325 A1 | 2/2006 | Paul et al. |
| 2006/0036326 A1 | 2/2006 | Baumgartner et al. |
| 2006/0041313 A1 | 2/2006 | Allard et al. |
| 2006/0041314 A1 | 2/2006 | Milliard |
| 2006/0058878 A1 | 3/2006 | Michelson |
| 2006/0064091 A1 | 3/2006 | Ludwig et al. |
| 2006/0069437 A1 | 3/2006 | Weber |
| 2006/0069441 A1 | 3/2006 | Zucherman et al. |
| 2006/0085076 A1 | 4/2006 | Krishna et al. |
| 2006/0085077 A1 | 4/2006 | Cook et al. |
| 2006/0089717 A1 | 4/2006 | Krishna et al. |
| 2006/0095136 A1 | 5/2006 | McLuen |
| 2006/0111783 A1 | 5/2006 | Aflatoon et al. |
| 2006/0116768 A1 | 6/2006 | Krueger et al. |
| 2006/0116769 A1 | 6/2006 | Marnay et al. |
| 2006/0122703 A1 | 6/2006 | Aebi et al. |
| 2006/0129244 A1 | 6/2006 | Ensign |
| 2006/0136063 A1 | 6/2006 | Zeegers |
| 2006/0142863 A1 | 6/2006 | Fraser et al. |
| 2006/0149273 A1 | 7/2006 | Ross et al. |
| 2006/0149371 A1 | 7/2006 | Marik et al. |
| 2006/0149378 A1 | 7/2006 | Chase et al. |
| 2006/0155377 A1 | 7/2006 | Beaurain et al. |
| 2006/0155378 A1 | 7/2006 | Eckman |
| 2006/0173544 A1 | 8/2006 | Gau |
| 2006/0178745 A1 | 8/2006 | Bartish, Jr. et al. |
| 2006/0178746 A1 | 8/2006 | Bartish, Jr. et al. |
| 2006/0190082 A1 | 8/2006 | Keller et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206208 A1 | 9/2006 | Michelson |
| 2006/0212123 A1 | 9/2006 | Lechmann et al. |
| 2006/0235426 A1 | 10/2006 | Lim et al. |
| 2006/0235520 A1 | 10/2006 | Pannu |
| 2006/0235526 A1 | 10/2006 | Lemaire |
| 2006/0241764 A1 | 10/2006 | Michelson |
| 2006/0253201 A1 | 11/2006 | McLuen |
| 2006/0259143 A1 | 11/2006 | Navarro et al. |
| 2006/0265072 A1 | 11/2006 | Richelsoph |
| 2006/0282074 A1 | 12/2006 | Renaud et al. |
| 2006/0287728 A1 | 12/2006 | Mokhtar et al. |
| 2007/0010886 A1 | 1/2007 | Banick et al. |
| 2007/0010887 A1 | 1/2007 | Williams et al. |
| 2007/0016217 A1 | 1/2007 | Dinville |
| 2007/0016297 A1 | 1/2007 | Johnson |
| 2007/0016299 A1 | 1/2007 | Eckman |
| 2007/0032871 A1 | 2/2007 | Michelson |
| 2007/0055378 A1 | 3/2007 | Ankney et al. |
| 2007/0073403 A1 | 3/2007 | Lombardo et al. |
| 2007/0073404 A1 | 3/2007 | Rashbaum et al. |
| 2007/0083201 A1 | 4/2007 | Jones et al. |
| 2007/0088362 A1 | 4/2007 | Bonutti et al. |
| 2007/0100454 A1 | 5/2007 | Burgess et al. |
| 2007/0100455 A1 | 5/2007 | Parsons |
| 2007/0100456 A1 | 5/2007 | Dooris et al. |
| 2007/0118223 A1 | 5/2007 | Allard et al. |
| 2007/0123985 A1 | 5/2007 | Errico et al. |
| 2007/0149974 A1 | 6/2007 | Mangione |
| 2007/0162130 A1 | 7/2007 | Rashbaum et al. |
| 2007/0179623 A1 | 8/2007 | Trieu et al. |
| 2007/0250167 A1 | 10/2007 | Bray et al. |
| 2007/0250168 A1 | 10/2007 | Lechmann et al. |
| 2007/0260249 A1 | 11/2007 | Boyajian et al. |
| 2007/0270951 A1 | 11/2007 | Davis et al. |
| 2007/0270954 A1 | 11/2007 | Wu |
| 2007/0270961 A1 | 11/2007 | Ferguson |
| 2007/0270967 A1 | 11/2007 | Fallin et al. |
| 2007/0276498 A1 | 11/2007 | Aebi et al. |
| 2007/0288094 A1 | 12/2007 | Krishna et al. |
| 2007/0299524 A1 | 12/2007 | Rivin |
| 2008/0021562 A1 | 1/2008 | Huppert |

| | | |
|---|---|---|
| 2008/0027547 A1 | 1/2008 | Yu et al. |
| 2008/0027550 A1 | 1/2008 | Link et al. |
| 2008/0033555 A1 | 2/2008 | Link et al. |
| 2008/0033562 A1 | 2/2008 | Krishna et al. |
| 2008/0051887 A1 | 2/2008 | Carter et al. |
| 2008/0109083 A1 | 5/2008 | Van Hoeck et al. |
| 2008/0125865 A1 | 5/2008 | Abdelgany et al. |
| 2008/0161930 A1 | 7/2008 | Carls et al. |
| 2008/0161933 A1 | 7/2008 | Grotz et al. |
| 2008/0195211 A1 | 8/2008 | Lin et al. |
| 2008/0200984 A1 | 8/2008 | Jodaitis et al. |
| 2008/0234686 A1 | 9/2008 | Beaurain et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0262504 A1 | 10/2008 | Ralph et al. |
| 2008/0281425 A1 | 11/2008 | Thalgott et al. |
| 2008/0294260 A1 | 11/2008 | Gray |
| 2008/0300634 A1 | 12/2008 | Gray |
| 2008/0300685 A1 | 12/2008 | Carls et al. |
| 2008/0306596 A1 | 12/2008 | Jones et al. |
| 2009/0030461 A1 | 1/2009 | Hoy et al. |
| 2009/0030519 A1 | 1/2009 | Falahee |
| 2009/0030520 A1 | 1/2009 | Biedermann et al. |
| 2009/0076615 A1 | 3/2009 | Duggal et al. |
| 2009/0099601 A1 | 4/2009 | Aferzon et al. |
| 2009/0105830 A1 | 4/2009 | Jones et al. |
| 2009/0105831 A1 | 4/2009 | Jones et al. |
| 2009/0105832 A1 | 4/2009 | Allain et al. |
| 2009/0118771 A1 | 5/2009 | Gonzalez-Hernandez |
| 2009/0125071 A1 | 5/2009 | Skinlo et al. |
| 2009/0132054 A1 | 5/2009 | Zeegers |
| 2009/0157188 A1 | 6/2009 | Zeegers |
| 2009/0164020 A1 | 6/2009 | Janowski et al. |
| 2009/0182429 A1 | 7/2009 | Humphreys et al. |
| 2009/0182430 A1 | 7/2009 | Tyber et al. |
| 2009/0186333 A1 | 7/2009 | Mills et al. |
| 2009/0192613 A1 | 7/2009 | Wing et al. |
| 2009/0192615 A1 | 7/2009 | Tyber et al. |
| 2009/0204219 A1 | 8/2009 | Beaurain et al. |
| 2009/0210062 A1 | 8/2009 | Thalgott et al. |
| 2009/0216241 A1 | 8/2009 | Dinville |
| 2009/0222092 A1 | 9/2009 | Davis et al. |
| 2009/0222100 A1 | 9/2009 | Cipoletti et al. |
| 2009/0228108 A1 | 9/2009 | Keller |
| 2009/0234455 A1 | 9/2009 | Moskowitz et al. |
| 2009/0265007 A1 | 10/2009 | Colleran |
| 2009/0270990 A1 | 10/2009 | Louis et al. |
| 2010/0004664 A1 | 1/2010 | Boyajian et al. |
| 2010/0049259 A1 | 2/2010 | Lambrecht et al. |
| 2010/0057206 A1 | 3/2010 | Duffield et al. |
| 2010/0057207 A1 | 3/2010 | Ray, III et al. |
| 2010/0063554 A1 | 3/2010 | Branch et al. |
| 2010/0070037 A1 | 3/2010 | Parry et al. |
| 2010/0082104 A1 | 4/2010 | Carter et al. |
| 2010/0082109 A1 | 4/2010 | Greenhalgh et al. |
| 2010/0087925 A1 | 4/2010 | Kostuik et al. |
| 2010/0106249 A1 | 4/2010 | Tyber et al. |
| 2010/0114317 A1 | 5/2010 | Lambrecht et al. |
| 2010/0121455 A1 | 5/2010 | Lambrecht et al. |
| 2010/0145459 A1 | 6/2010 | McDonough et al. |
| 2010/0145460 A1 | 6/2010 | McDonough et al. |
| 2010/0145463 A1 | 6/2010 | Michelson |
| 2010/0152856 A1 | 6/2010 | Overes et al. |
| 2010/0160984 A1 | 6/2010 | Berry et al. |
| 2010/0161057 A1 | 6/2010 | Berry et al. |
| 2010/0179655 A1 | 7/2010 | Hansell et al. |
| 2010/0185289 A1 | 7/2010 | Kirwan et al. |
| 2010/0204796 A1 | 8/2010 | Bae et al. |
| 2010/0211108 A1 | 8/2010 | Lemole, Jr. |
| 2010/0211176 A1 | 8/2010 | Greenhalgh |
| 2010/0217393 A1 | 8/2010 | Theofilos |
| 2010/0217396 A1 | 8/2010 | Bianchi et al. |
| 2010/0234958 A1 | 9/2010 | Linares |
| 2010/0249935 A1 | 9/2010 | Slivka et al. |
| 2010/0249937 A1 | 9/2010 | Blain et al. |
| 2010/0268349 A1 | 10/2010 | Bianchi et al. |
| 2010/0280618 A1 | 11/2010 | Jodaitis et al. |
| 2010/0286777 A1 | 11/2010 | Errico et al. |
| 2010/0286787 A1 | 11/2010 | Villiers et al. |
| 2010/0305700 A1 | 12/2010 | Ben-Arye et al. |
| 2010/0305704 A1 | 12/2010 | Messerli et al. |
| 2010/0312344 A1 | 12/2010 | Reiley |
| 2010/0312345 A1 | 12/2010 | Duffield et al. |
| 2010/0312346 A1 | 12/2010 | Kueenzi et al. |
| 2011/0004310 A1 | 1/2011 | Michelson |
| 2011/0009966 A1 | 1/2011 | Michelson |
| 2011/0015745 A1 | 1/2011 | Bucci |
| 2011/0035007 A1 | 2/2011 | Patel et al. |
| 2011/0040382 A1 | 2/2011 | Muhanna |
| 2011/0054616 A1 | 3/2011 | Kamran et al. |
| 2011/0077738 A1 | 3/2011 | Ciupik et al. |
| 2011/0077739 A1 | 3/2011 | Rashbaum et al. |
| 2011/0082553 A1 | 4/2011 | Abdou |
| 2011/0087327 A1 | 4/2011 | Lechmann et al. |
| 2011/0093077 A1 | 4/2011 | Aebi et al. |
| 2011/0098747 A1 | 4/2011 | Donner et al. |
| 2011/0118843 A1 | 5/2011 | Mathieu et al. |
| 2011/0125267 A1 | 5/2011 | Michelson |
| 2011/0137420 A1 | 6/2011 | Michelson |
| 2011/0144703 A1 | 6/2011 | Krause et al. |
| 2011/0160860 A1 | 6/2011 | Johnston et al. |
| 2011/0166655 A1 | 7/2011 | Michelson |
| 2011/0166656 A1 | 7/2011 | Thalgott et al. |
| 2011/0166657 A1 | 7/2011 | Thalgott et al. |
| 2011/0166658 A1 | 7/2011 | Garber et al. |
| 2011/0172774 A1 | 7/2011 | Varela |
| 2011/0196492 A1 | 8/2011 | Lambrecht et al. |
| 2011/0196493 A1 | 8/2011 | Pimenta |
| 2011/0196494 A1 | 8/2011 | Yedlicka et al. |
| 2011/0202136 A1 | 8/2011 | Brittan et al. |
| 2011/0208311 A1 | 8/2011 | Janowski |
| 2011/0208313 A1 | 8/2011 | Michelson |
| 2011/0230969 A1 | 9/2011 | Biedermann et al. |
| 2011/0230971 A1 | 9/2011 | Donner et al. |
| 2011/0264227 A1 | 10/2011 | Boyajian et al. |
| 2011/0295371 A1 | 12/2011 | Moskowitz et al. |
| 2011/0301707 A1 | 12/2011 | Buskirk et al. |
| 2011/0301713 A1 | 12/2011 | Theofilos |
| 2011/0301714 A1 | 12/2011 | Theofilos |
| 2011/0313528 A1 | 12/2011 | Laubert et al. |
| 2012/0004660 A1 | 1/2012 | Grooms et al. |
| 2012/0053693 A1 | 3/2012 | Zeegers |
| 2012/0116466 A1 | 5/2012 | Dinville et al. |
| 2012/0191196 A1 | 7/2012 | Louis et al. |

FOREIGN PATENT DOCUMENTS

| | | |
|---|---|---|
| CA | 2443215 | 10/2002 |
| CA | 2472708 | 2/2005 |
| CA | 2533473 | 3/2011 |
| DE | 3741493 | 6/1989 |
| DE | 29911422 | 8/1999 |
| DE | 20320454 | 10/2004 |
| DE | 10323363 | 12/2004 |
| EP | 42271 | 12/1981 |
| EP | 0274713 A | 7/1988 |
| EP | 0301489 A | 2/1989 |
| EP | 0317972 A | 5/1989 |
| EP | 0333990 A | 9/1989 |
| EP | 0356112 | 2/1990 |
| EP | 0512529 A | 11/1992 |
| EP | 0560141 A | 9/1993 |
| EP | 0566810 A1 | 10/1993 |
| EP | 0637439 | 2/1995 |
| EP | 0697200 | 2/1996 |
| EP | 0566810 B1 | 5/1996 |
| EP | 0747025 A1 | 12/1996 |
| EP | 0951879 | 10/1999 |
| EP | 0955021 A | 11/1999 |
| EP | 0965313 | 12/1999 |
| EP | 1222903 | 7/2002 |
| EP | 1254640 A | 11/2002 |
| EP | 1287795 | 3/2003 |
| EP | 1504733 | 2/2005 |
| EP | 1374808 | 12/2005 |
| EP | 2113228 | 11/2009 |
| EP | 2327375 | 6/2011 |
| EP | 2340788 | 7/2011 |

| | | |
|---|---|---|
| EP | 2363080 | 9/2011 |
| FR | 2124815 A | 9/1972 |
| FR | 2632516 A | 2/1989 |
| FR | 2659226 A | 9/1991 |
| FR | 2703580 | 10/1994 |
| FR | 2723841 | 3/1996 |
| FR | 2724108 A | 3/1996 |
| FR | 2730159 A1 | 8/1996 |
| FR | 2733413 | 10/1996 |
| FR | 2747034 | 10/1997 |
| FR | 2787021 A | 6/2000 |
| FR | 2808995 | 11/2001 |
| FR | 2824261 | 11/2002 |
| FR | 2827156 | 1/2003 |
| FR | 2831796 | 5/2003 |
| FR | 2846550 | 5/2004 |
| FR | 2861582 | 5/2005 |
| FR | 2865629 | 8/2005 |
| FR | 2879436 | 6/2006 |
| FR | 2880795 | 7/2006 |
| FR | 2887762 | 1/2007 |
| FR | 2891135 | 3/2007 |
| FR | 2893838 | 6/2007 |
| FR | 2897259 | 8/2007 |
| FR | 2916956 | 12/2008 |
| GB | 2178323 A | 2/1987 |
| JP | 2261446 | 10/1990 |
| JP | 9098983 | 4/1997 |
| WO | WO9107931 | 6/1991 |
| WO | WO9301771 A | 2/1993 |
| WO | WO9307823 | 4/1993 |
| WO | WO9404100 | 3/1994 |
| WO | WO9508306 | 3/1995 |
| WO | WO9510240 A | 4/1995 |
| WO | WO9515133 | 6/1995 |
| WO | WO9715248 | 5/1997 |
| WO | WO9801091 | 1/1998 |
| WO | WO9817209 | 4/1998 |
| WO | WO9855052 | 12/1998 |
| WO | WO9900065 | 1/1999 |
| WO | WO9909914 | 3/1999 |
| WO | WO9933405 A | 7/1999 |
| WO | WO9953871 | 10/1999 |
| WO | WO9956675 A | 11/1999 |
| WO | WO9956676 | 11/1999 |
| WO | WO9963914 | 12/1999 |
| WO | WO9965412 | 12/1999 |
| WO | WO9966864 | 12/1999 |
| WO | WO0015125 A | 3/2000 |
| WO | WO0018312 A | 4/2000 |
| WO | WO0024327 | 5/2000 |
| WO | WO0053127 A | 9/2000 |
| WO | WO0074606 A | 12/2000 |
| WO | WO0101874 A | 1/2001 |
| WO | WO0103592 A | 1/2001 |
| WO | WO0119295 A | 3/2001 |
| WO | WO0126566 A | 4/2001 |
| WO | WO0141680 | 6/2001 |
| WO | WO0143620 | 6/2001 |
| WO | WO0162191 | 8/2001 |
| WO | WO0170141 | 9/2001 |
| WO | WO0187194 | 11/2001 |
| WO | WO0213732 | 2/2002 |
| WO | WO0228299 A | 4/2002 |
| WO | WO0230307 A | 4/2002 |
| WO | WO02058599 | 8/2002 |
| WO | WO02071960 | 9/2002 |
| WO | WO02080788 | 10/2002 |
| WO | WO02089701 A2 | 11/2002 |
| WO | WO03005939 | 1/2003 |
| WO | WO03015646 | 2/2003 |
| WO | WO03026522 | 4/2003 |
| WO | WO03032850 A1 | 4/2003 |
| WO | WO03032851 | 4/2003 |
| WO | WO03039400 A2 | 5/2003 |
| WO | WO03045262 | 6/2003 |
| WO | WO03049629 A1 | 6/2003 |
| WO | WO03059212 A | 7/2003 |
| WO | WO03075803 | 9/2003 |
| WO | WO03075804 A | 9/2003 |
| WO | WO2004034935 | 4/2004 |
| WO | WO2004039291 | 5/2004 |
| WO | WO2004041129 | 5/2004 |
| WO | WO2004041129 A1 | 5/2004 |
| WO | WO2004041131 | 5/2004 |
| WO | WO2004071360 | 8/2004 |
| WO | WO2004084742 | 10/2004 |
| WO | WO2004089256 | 10/2004 |
| WO | WO2005007040 | 1/2005 |
| WO | WO2005020829 A1 | 3/2005 |
| WO | WO2005044119 A2 | 5/2005 |
| WO | WO2005046534 | 5/2005 |
| WO | WO2005051243 | 6/2005 |
| WO | WO2005074839 | 8/2005 |
| WO | WO2005104996 | 11/2005 |
| WO | WO2005117728 | 12/2005 |
| WO | WO2006016384 | 2/2006 |
| WO | WO2006047587 | 5/2006 |
| WO | WO2006062960 | 6/2006 |
| WO | WO2006120505 | 11/2006 |
| WO | WO2006130460 | 12/2006 |
| WO | WO2006136760 | 12/2006 |
| WO | WO2007000654 | 1/2007 |
| WO | WO2007034310 | 3/2007 |
| WO | WO2007063398 | 6/2007 |
| WO | WO2007078978 | 7/2007 |
| WO | WO2007093900 | 8/2007 |
| WO | WO2008099277 | 8/2008 |
| WO | WO2008149223 | 12/2008 |
| WO | WO2009033100 | 3/2009 |
| WO | WO2011080535 | 7/2011 |

OTHER PUBLICATIONS

A Multicenter Retrospective Study of the Clinical Results of the Link SB Charite Intervertebral Prosthesis, S.L. Griffith, PhD, A.P. Shelokov, MD, K. Buttner-Janz, MD, Jean-Phillipe LeMaire, MD and W.S. Zeegers, MD, Spine, vol. 19, No. 16, pp. 1842-1849, Mar. 21, 1994.

A New Technique for the Three-Dimensional Study of the Spine in Vitro and in Vivo by Using a Motion-Analysis System, X. Liu, G. Fabry, K. Labey, L. Van Den Berghe, R. Van Audekercke, G. Molenaers, P. Moens, Journal of Spinal Disorders, vol. 10, No. 4, pp. 329-338, Jan. 30, 1997.

Alternatives to Spinal Fusion, J.P., Kostuik, Spinal Fusion, vol. 29, No. 4, Oct. 1998, pp. 701-713.

Centrode Patterns and Segmental Instability in Degenerative Disc Disease, S.D. Gertzban, MD, FRCSC, J. Seligman, MD, R. Holtby, MD, K.H. Chan, MD, A. Kapasouri, BSc, M. Title, MD, BSc, (MED), FRCSC ©, and B. Cruickshank, MD, FRCPath, Spine, vol. 10, No. 3, pp. 257-261, Jan. 21, 1984.

Clinical Biomechanics of the Spine, A.A. White III, M.M. Panjabi, pp. 128-130, 2nd Edition, J.B. Lippincott Co., 1990.

Computer Analysis of Spinal Segment Motion in Degenerative Disc Disease with and Without Axial Loading, J.V. Seligman, S.D. Gertzbein, M. Tile, A., Kapasouri, Spine, vol. 9., No. 6, pp. 566-573, Dec. 31, 1983.

FR 2 718 635 Preliminary Search Report, National Institute of Industrial Property (France), Jan. 16, 1995.

FR 2 730 159 Preliminary Search Report, National Institute of Industrial Property (France), Sep. 29, 1995.

FR 2 824 261 Preliminary Search Report, National Institute of Industrial Property (France), Feb. 25, 2002.

FR 2 831 796 Preliminary Search Report, National Institute of Industrial Property (France), Aug. 2, 2002.

FR 2 846 550 Preliminary Search Report, National Institute of Industrial Property (France), Jul. 10, 2003.

FR 2 865 629 Preliminary Search Report, National Institute of Industrial Property (France), Sep. 14, 2004.

FR 2 865 630 Preliminary Search Report, National Institute of Industrial Property (France), Jan. 12, 2005.

FR 2 869 528 Preliminary Search Report, National Institute of Industrial Property (France), Dec. 13, 2004.

Instantaneous Axis of Rotation as a Function of the Three Columns of the Spine, T.R. Haher, MD, M. O'Brien, MD, W.T. Felmly, MD, D. Welin, MD, G. Perrier, MD, J. Choueka, JD, V. Devlin, MD, A. Vassioiou, ME, and G. Chow, MD, Spine, vol. 17, No. 6, pp. S149-S154, Jan. 9, 1992.
Instantaneous Axis of Rotation of the Lumbar Intervertebral Joints, M.J. Pearcy, H. Bogduk, Spine, vol. 13, No. 9, pp. 1033-1041, Nov. 15, 1987.
Mobidisc (website) 1 page, www.ldrmedical.fr/mobidisc.htm, Sep. 19, 2004.
Motion Characteistics of the Normal Lumbar Spine in Young Adults: Instantaneous of Axis of Rotation and Vertebral Center Motion Analysis. t. Yoshioka, H. Tsuji, N.Hirano and S. Sainoh, Journal of Spinal Disorders, vol. 3, No. 2, pp. 103-113, 1990.
PCT/IB02/02998 International Search Report, EPO, Sep. 16, 2003.
PCT/IB02/04642 International Search Report, EPO, Jul. 2, 2003.
PCT/IB05/00280 International Search Report, EPO, Jun. 24, 2005.
PCT/IB05/01151 International Search Report, EPO, Sep. 12, 2005.
PCT/IB03/04672 International Search Report, EPO, Mar. 3, 2004.
PCT/IB02/02998 International Preliminary Examination Report, EPO, Dec. 22, 2003.
PCT/IB02/04642 International Preliminary Examination Report, EPO, Apr. 1, 2004.
PCT/IB03/04872 International Preliminary Examination Report, EPO, Mar. 1, 2005.
Relocation of the Bending Axis During Flexion-Extension of Lumbar Intervertebral Discs and its Implications for Prolapse, J.A. Klein and D.W.L. Hukins, Spine, vol. 8, No. 6, pp. 659-664. Nov. 18, 1982.
The Effect of the Three Columns of the Spine on the Instantaneous Axis of Rotation in Flexion and Extension, T. R. Haher, M. Bergman, M. O'Brien, W.T. Felmly, J. Choueka, D. Welin, G. Chow, A. Vassiliou, Spine, vol. 16, No. 8, pp. S312-S318, Apr. 16, 1991.
USPTO OA of Feb. 6, 2007 in U.S. Appl. No. 11/109,276.
USPTO OA of Oct. 16, 2007 in U.S. Appl. No. 11/109,276.
USPTO OA of Jul. 24, 2008 in U.S. Appl. No. 11/109,276.
USPTO OA of Feb. 13, 2009 in U.S. Appl. No. 11/109,276.
Applicant's Reply to USPTO OA of Feb. 6, 2007 in U.S. Appl. No. 11/109,276.
Applicant's Reply to USPTO OA of Oct. 16, 2007 in U.S. Appl. No. 11/109,276.
Applicant's Reply to USPTO OA of Jul. 24, 2008 in U.S. Appl. No. 11/109,276.
Applicant's response to USPTO OA of Feb. 13, 2009 in U.S. Appl. No. 11/109,276.
USPTO OA of Apr. 18, 2007 in U.S. Appl. No. 10/533,846.
Applicant's Response to USPTO OA of Apr. 18, 2007 in U.S. Appl. No. 10/533,846.
USPTO OA of Dec. 26, 2007 in U.S. Appl. No. 10/533,846.
Applicant's Response to USPTO OA of Dec. 26, 2007 in U.S. Appl. No. 10/533,846.
USPTO OA of Oct. 15, 2008 in U.S. Appl. No. 10/533,846.
Applicant's Response to USPTO OA of Oct. 15, 2008 in U.S. Appl. No. 10/533,846.
USPTO OA of Jan. 22, 2008 in U.S. Appl. No. 11/180,868.
Applicant's Response to USPTO OA of Jan. 22, 2008 in U.S. Appl. No. 11/180,868.
USPTO OA of Nov. 5, 2008 in U.S. Appl. No. 11/180,868.
Response to USPTO OA of Nov. 5, 2008 in U.S. Appl. No. 11/180,868.
USPTO OA of Apr. 13, 2009 in U.S. Appl. No. 11/341,007.
USPTO OA of Mar. 20, 2009 in U.S. Appl. No. 11/676,237.
USPTO OA of Feb. 18, 2009 in U.S. Appl. No. 11/632,253.
Applicants' Response to USPTO OA of Feb. 18, 2009 in U.S. Appl. No. 11/632,253.
A unique self-contained connexion; Website; www.ldrmedical.dr/connexion_uk.htm; Oct. 11, 2004.
FR 2 704 136 Preliminary Search Report, National Institute of Industrial Property (France), Nov. 24, 1993.
FR 2 823 095 Preliminary Search Report, National Institute of Industrial Property (France), Dec. 20, 2001.
FR 2 827 150 Preliminary Search Report, National Institute of Industrial Property (France), Apr. 8, 2002.
FR 2 831 048 Preliminary Search Report, National Institute of Industrial Property (France), Jul. 3, 2002.
FR 2 831 049 Preliminary Search Report, National Institute of Industrial Property (France), Jul. 3, 2002.
FR 2 833 151 Preliminary Search Report, National Institute of Industrial Property (France), Aug. 28, 2002.
FR 2 859 095 Preliminary Search Report, National Institute of Industrial Property (France), Apr. 14, 2004.
PCT/FR98/01363 (Publication WO9900065 Jan. 7, 1999), International Search Report, EPO, Oct. 14, 1998.
PCT/IB02/02827 International Search Report, EPO, Oct. 4, 2002.
PCT/IB02/04306 International Search Report, EPO, Feb. 4, 2003.
PCT/IB02/04307 International Search Report, EPO, Feb. 4, 2003.
PCT/IB02/05302 International Search Report, EPO, Mar. 25, 2003.
PCT/IB04/002825 International Search Report, EPO, Jan. 7, 2005.
PCT/IB02/02827 International Preliminary Examination Report, EPO, May 15, 2003.
PCT/IB02/04306 International Preliminary Examination Report, EPO, Jul. 9, 2003.
PCT/IB02/04307 International Preliminary Examination Report, EPO, Jan. 13, 2004.
PCT/IB02/04642, International Preliminary Examination Reort, EPO, Apr. 1, 2004.
PCT/IB02/05302 International Preliminary Examination Report, EPO, Mar. 23, 2004.
PCT/IB04/002825, International Preliminary Report on Patentability, EPO, Oct. 25, 2005.
PCT/IB04/002825, Written Opinion of the International Searching Authority, EPO, Jan. 5, 2005.
PCT/IB08/001815, International Search Report and Written Opinion, EPO, Apr. 6, 2009.
Un nouveau standard: la barre á méplat LDR: Website: www.ldrmedical.fr/easyspine.htm; Sep. 19, 2004.
USPTO OA of May 8, 2006 in U.S. Appl. No. 10/498,234.
USPTO OA of Dec. 26, 2006 in U.S. Appl. No. 10/498,234.
USPTO OA of Aug. 29, 2007 in U.S. Appl. No. 10/498,234.
USPTO OA of Nov. 21, 2007 in U.S. Appl. No. 10/498,234.
USPTO OA of Aug. 20, 2008 in U.S. Appl. No. 10/498,234.
USPTO OA of Sep. 12, 2005 in U.S. Appl. No. 10/473,999.
USPTO OA of May 4, 2006, in U.S. Appl. No. 10/473,999.
USPTO OA of Oct. 19, 2006 in U.S. Appl. No. 10/473,999.
USPTO OA of Jul. 30, 2007 in U.S. Appl. No. 10/473,999.
USPTO OA of Jan. 24, 2008 in U.S. Appl. No. 10/473,999.
USPTO OA of Apr. 3, 2008 in U.S. Appl. No. 10/473,999.
USPTO OA of Jun. 14, 2006 in U.S. Appl. No. 10/492,753.
USPTO OA of Feb. 21, 2007, in U.S. Appl. No. 10/492,753.
USPTO OA of Oct. 16, 2007, in U.S. Appl. No. 10/492,753.
USPTO OA of Oct. 6, 2008, in U.S. Appl. No. 10/492,753.
USPTO OA of Dec. 14, 2005 in U.S. Appl. No. 10/492,827.
USPTO OA of Oct. 20, 2006 in U.S. Appl. No. 10/492,827.
USPTO OA of Apr. 3, 2007 in U.S. Appl. No. 10/492,827.
USPTO OA of Dec. 24, 2008, in U.S. Appl. No. 10/492,827.
Reply to USPTO OA of Nov. 21, 2007 in U.S. Appl. No. 10/498,234.
Reply to USPTO Action of May 8, 2006 in U.S. Appl. No. 10/498,234.
Reply to USPTO Action of Dec. 26, 2006 in U.S. Appl. No. 10/498,234.
Reply to USPTO Action of Aug. 29, 2007 in U.S. Appl. No. 10/498,234.
Reply to USPTO OA of Sep. 12, 2005 in U.S. Appl. No. 10/473,999.
Reply to USPTO OA of May 4, 2006, in U.S. Appl. No. 10/473,999.
Reply to USPTO OA of Oct. 19, 2006 in U.S. Appl. No. 10/473,999.
Reply to USPTO OA of Jul. 30, 2007 in U.S. Appl. No. 10/473,999.
Reply to USPTO OA of Apr. 3, 2008 in U.S. Appl. No. 10/473,999.
Reply to USPTO OA of Jun. 14, 2006 in U.S. Appl. No. 10/492,753.
Reply to USPTO OA of Feb. 21, 2007, in U.S. Appl. No. 10/492,753.
Reply to USPTO OA of Oct. 16, 2007, in U.S. Appl. No. 10/492,753.
Reply to USPTO OA of Oct. 6, 2008, in U.S. Appl. No. 10/492,753.
Reply to USPTO OA of Dec. 14, 2005 in U.S. Appl. No. 10/492,827.
Reply to USPTO OA of Oct. 20, 2006 in U.S. Appl. No. 10/492,827.
Reply to USPTO OA of Apr. 3, 2007 in U.S. Appl. No. 10/492,827.
LDR Medical, by its attorneys; Amendment for Pub'n No. EP2162098; Jan. 6, 2010; EPO; Munich, Germany; all pages.

European Patent Office; Office Action for Pub'n No. EP2162098; Jan. 17, 2012; EPO; Munich, Germany; all pages.
LDR Medical, by its attorneys; Reply to Office Action for Pub'n No. EP2162098; Jul. 27, 2012; EPO; Munich, Germany; all pages.
National Institute of Industrial Property (France); Search Report for Pub'n No. FR2916956; Jan. 30, 2008; National Institute of Industrial Property (France); France; all pages.
World Intellectual Property Organization; Written Opinion of the International Searching Authority for PCT Pub'n No. WO2008149223; Feb. 16, 2009; WIPO; Geneva, Switzerland; all pages.
World Intellectual Property Organization; International Search Report for PCT Pub'n No. WO2008149223; Feb. 16, 2009; WIPO; Geneva, Switzerland; all pages.
LDR Medical, by its attorneys; Amendment for Pub'n No. WO2008149223; May 13, 2009; WIPO; Geneva, Switzerland; all pages.
World Intellectual Property Organization; International Preliminary Report on Patentability for PCT Pub'n No. WO2008149223; Aug. 5, 2009; WIPO; Geneva, Switzerland; all pages.
World Intellectual Property Organization; Written Opinon of the International Searching Authority for PCT Pub'n No. WO2011080535; Feb. 2, 2011; WIPO; Geneva, Switzerland; all pages.
World Intellectual Property Organization; International Search Report for PCT Pub'n No. WO2011080535; Feb. 2, 2011; WIPO; Geneva, Switzerland; all pages.
LDR Medical, by its attorneys; Demand for PCT Pub'n. No. WO2011080535; Apr. 22, 2011; WIPO; Geneva, Switzerland; all pages.
World Intellectual Property Organization; Interview Summary for PCT Pub'n No. WO2011080535; Feb. 14, 2012; WIPO; Geneva, Switzerland; all pages.
LDR Medical, by its attorneys; Amendment for Pub'n. No. WO2011080535; Apr. 2, 2012; WIPO; Geneva, Switzerland; all pages.
World Intellectual Property Organization; International Preliminary Report on Patentability for PCT Pub'n No. WO2011080535; Apr. 18, 2012; WIPO; Geneva, Switzerland; all pages.
European Patent Office; Office Action for Pub'n No. EP1406563; Mar. 13, 2009; EPO; Munich, Germany; all pages.
LDR Medical, by its attorneys; Reply to Office Action for Pub'n No. EP1406563; Jul. 22, 2009; EPO; Munich, Germany; all pages.
European Patent Office; Office Action for Pub'n No. EP1406563; Aug. 4, 2009; EPO; Munich, Germany; all pages.
LDR Medical, by its attorneys; Reply to Office Action for Pub'n No. EP1406563; Oct. 14, 2009; EPO; Munich, Germany; all pages.
European Patent Office; Notice of Intent to Grant Patent for Pub'n No. EP1406563; Aug. 26, 2010; EPO; Munich, Germany; all pages.
European Patent Office; Search Report for Pub'n No. EP2113228; Oct. 6, 2009; EPO; Munich, Germany; all pages.
LDR Medical, by its attorneys; Amendment for Pub'n No. EP2113228; Apr. 26, 2010; EPO; Munich, Germany; all pages.
European Patent Office; Search Report for Pub'n No. EP2340788; Jun. 8, 2011; EPO; Munich, Germany; all pages.
National Institute of Industrial Property (France); Search Report for Pub'n No. FR2827156; Apr. 5, 2012; National Institute of Industrial Property (France); France; all pages.
World Intellectual Property Organization; International Search Report for PCT Pub'n No. WO03005939; Mar. 3, 2003; WIPO; Geneva, Switzerland; all pages.
World Intellectual Property Organization; International Preliminary Examination Report for PCT Pub'n No. WO03005939; Nov. 6, 2003; WIPO; Geneva, Switzerland; all pages.
U.S. Patent & Trademark Office; Office Action in U.S. Appl. No. 10/483,563; Feb. 21, 2007; USPTO; Alexandria, Virginia; All pages.
LDR Medical, by its attorneys; Reply to Office Action in U.S. Appl. No. 10/483,563; Aug. 21, 2007; USPTO; Alexandria, Virginia; All pages.
U.S. Patent & Trademark Office; Office Action in U.S. Appl. No. 10/483,563; Oct. 30, 2007; USPTO; Alexandria,Virginia; All pages.
LDR Medical, by its attorneys; Reply to Office Action in U.S. Appl. No. 10/483,563; Nov. 19, 2007; USPTO; Alexandria, Virginia; All pages.
U.S. Patent & Trademark Office; Office Action in U.S. Appl. No. 10/483,563; Jan. 31, 2008; USPTO; Alexandria, Virgina; All pages.
LDR Medical, by its attorneys; Reply to Office Action in U.S. Appl. No. 10/483,563; Jul. 31, 2008; USPTO; Alexandria, Virgina; All pages.
U.S. Patent & Trademark Office; Office Action in U.S. Appl. No. 10/483,563; Oct. 28, 2008; USPTO; Alexandria, Virgina; All pages.
LDR Medical, by its attorneys; Reply to Office Action in U.S. Appl. No. 10/483,563; Apr. 28, 2009; USPTO; Alexandria, Virgina; All pages.
U.S. Patent & Trademark Office; Notice of Allowance in U.S. Appl. No. 10/483,563; Jun. 5, 2009; USPTO; Alexandria, Virgina; All pages.
U.S. Patent & Trademark Office; Notice of Allowance in U.S. Appl. No. 10/483,563; Jun. 19, 2009; USPTO; Alexandria, Virgina; All pages.
U.S. Patent & Trademark Office; Office Action in U.S. Appl. No. 12/430,768; Jun. 14, 2011; USPTO; Alexandria, Virgina; All pages.
LDR Medical, by its attorneys; Reply to Office Action in U.S. Appl. No. 12/430,768; Dec. 14, 2011; USPTO; Alexandria, Virgina; All pages.
U.S. Patent & Trademark Office; Notice of Allowance in U.S. Appl. No. 12/430,768; Jan. 11, 2012; USPTO; Alexandria, Virgina; All pages.
U.S. Patent & Trademark Office; Notice of Allowance in U.S. Appl. No. 12/430,768; Jan. 19, 2012; USPTO; Alexandria, Virgina; All pages.
LDR Medical, by its attorneys; Amendment for Pub'n No. EP1996127; Nov. 26, 2008; EPO; Munich, Germany; all pages.
National Institute of Industrial Property (France); Search Report for Pub'n No. FR2897259; Oct. 11, 2006; National Institute of Industrial Property (France); France; all pages.
World Intellectual Property Organization; Written Opinon of the International Searching Authority for PCT Pub'n No. WO2007093900; Oct. 22, 2007; WIPO; Geneva, Switzerland; all pages.
World Intellectual Property Organization; International Search Report for PCT Pub'n No. WO2007093900; Oct. 22, 2007; WIPO; Geneva, Switzerland; all pages.
World International Property Organization; International Preliminary Report on Patentability for PCT Pub'n No. WO2007093900; Feb. 5, 2008, WIPO; Geneva, Switzerland; all pages.
U.S. Patent & Trademark Office; Office Action in U.S. Appl. No. 12/279,664; Sep. 14, 2011; USPTO; Alexandria, Virginia; All pages.
LDR Medical, by its attorneys; Reply to Office Action in U.S. Appl. No. 12/279,664; Mar. 14, 2012; USPTO; Alexandria, Virginia; All pages.
U.S. Patent & Trademark Office; Notice of Allowance and Interview Summary in U.S. Appl. No. 12/279,664; Apr. 11, 2012; USPTO; Alexandria, Virgina; All pages.
U.S. Patent & Trademark Office; Notice of Allowance in U.S. Appl. No. 12/279,664; May 29, 2012; USPTO; Alexandria, Virgina; All pages.
National Institute of Industrial Property (France); Search Report for Pub'n No. FR2879436; Aug. 11, 2005; National Institute of Industrial Property (France); France; all pages.
World Intellectual Property Organization; Written Opinon of the International Searching Authority for PCT Pub'n No. WO2006120505; Aug. 21, 2006; WIPO; Geneva, Switzerland; all pages.
World Intellectual Property Organization; International Search Report for PCT Pub'n No. WO2006120505; Aug. 21, 2006; WIPO; Geneva, Switzerland; all pages.
World Intellectual Property Organization; Chapter II amendments for PCT Pub'n No. W2006120505; Nov. 16, 2006; WIPO; Geneva, Switzerland; All pages.
World Intellectual Property Organization; International Preliminary Report on Patentability for PCT Pub'n No. WO2006120505; Feb. 22, 2007; WIPO; Geneva, Switzerland; all pages.

European Patent Office; Office action and search report in Application No. 05857774; May 6, 2009; European Patent Office; Munich, Germany; All pages.
LDR Medical, by its attorneys; Amendments and Reply in European Patent Application No. 05857774; Nov. 13, 2009; European Patent Office; Munich, Germany; All pages.
European Patent Office; Office action and search report in Application No. 05857774; Apr. 11, 2011; European Patent Office; Munich, Germany; All pages.
European Patent Office; Office action and search report in Application No. 11165170; Jul. 21, 2011; European Patent Office; Munich, Germany; All pages.
LDR Medical, by its attorneys; Amendments and Reply in European Patent Application No. 05857774; Oct. 11, 2011; European Patent Office; Munich, Germany; All pages.
LDR Medical, by its attorneys; Amendments and Reply in European Patent Application No. 11165170; Mar. 6, 2012; European Patent Office; Munich, Germany; All pages.
European Patent Office; Office action in Application No. 11165170; Jul. 21, 2011; European Patent Office; Munich, Germany; All pages.
U.S. Patent & Trademark Office; Notice of Allowance in U.S. Appl. No. 11/109,276; Dec. 8, 2009; USPTO; Alexandria, Virgina; All pages.
U.S. Patent & Trademark Office; Office Action and Notice of Reference Cited in U.S. Appl. No. 12/360,050; Dec. 17, 2010; USPTO; Alexandria, Va.; All pages.
U.S. Patent & Trademark Office; Office Action in U.S. Appl. No. 12/360,050; Dec. 17, 2010; USPTO; Alexandria, Virginia; All pages.
LDR Medical, by its attorneys; Reply to Office Action in U.S. Appl. No. 12/360,050; Jun. 16, 2011; USPTO; Alexandria, Va.; All pages.
LDR Medical, by its attorneys; Reply to Office Action in U.S. Appl. No. 12/360,050; Jun. 16, 2011; USPTO; Alexandria, Virgina; All pages.
U.S. Patent & Trademark Office; Notice of Allowability in Application U.S. Appl. No. 12/360,050; Mar. 26, 2012; Uspto; Alexandria, Va.; All pages.
U.S. Patent & Trademark Office; Office Action and Notice of Reference Cited in U.S. Appl. No. 12/360,050; Sep. 6, 2011; USPTO; Alexandria, Va.; All pages.
LDR Medical, by its attorneys; Reply to Office Action in U.S. Appl. No. 12/360,050; Mar. 6, 2012; USPTO; Alexandria, Va.; All pages.
LDR Medical, by its attorneys; Reply to Office Action in U.S. Appl. No. 12/360,050; Mar. 6, 2012; USPTO; Alexandria, Virgina; All pages.
U.S. Patent & Trademark Office; Notice of Allowance in U.S. Appl. No. 12/360,050; Mar. 26, 2012; USPTO; Alexandria, Va.; All pages.
U.S. Patent & Trademark Office; Notice of Allowance in U.S. Appl. No. 12/360,050; Mar. 26, 2012; USPTO; Alexandria, Virginia; All pages.
U.S. Patent & Trademark Office; Notice of Allowability in U.S. Appl. No. 12/360,050; May 18, 2012; USPTO; Alexandria, Va.; All pages.
LDR Medical, by its attorneys; Request for Continued Examination in U.S. Appl. No. 12/360,050; Jun. 25, 2012; USPTO; Alexandria, Va.; All pages.
U.S. Patent & Trademark Office; Notice of Allowability in U.S. Appl. No. 12/360,050; Jul. 6, 2012; USPTO; Alexandria, Va.; All pages.
U.S. Patent & Trademark Office; Notice of Allowability in U.S. Appl. No. 12/360,050; Aug. 2, 2012; USPTO; Alexandria, Va.; All pages.
National Institute of Industrial Property (France); Search Report for Pub'n No. FR2808995; Jan. 29, 2001; National Institute of Industrial Property (France); France; all pages.
World Intellectual Property Organization; International Search Report for PCT Pub'n No. WO0187194; Sep. 5, 2001; WIPO; Geneva, Switzerland; all pages.
World Intellectual Property Organization; International Preliminary Examination Report for PCT Pub'n No. WO0187194; Aug. 30, 2002; WIPO; Geneva, Switzerland; all pages.
U.S. Patent & Trademark Office; Office Action in U.S. Appl. No. 10/276,712; Jan. 23, 2004; USPTO; Alexandria, Virgina; All pages.
U.S. Patent & Trademark Office; Office Action in U.S. Appl. No. 10/276,712; Jun. 30, 2004; USPTO; Alexandria, Virgina; All pages.
LDR Medical, by its attorneys; Reply to Office Action in U.S. Appl. No. 10/276,712; Sep. 27, 2004; USPTO; Alexandria, Virgina; All pages.
LDR Medical, by its attorneys; Reply to Office Action in U.S. Appl. No. 10/276,712; Mar. 1, 2005; USPTO; Alexandria, Virgina; All pages.
U.S. Patent & Trademark Office; Office Action in Applcation U.S. Appl. No. 10/276,712; May 27, 2005; USPTO; Alexandria, Virgina; All pages.
LDR Medical, by its Attorneys; Reply to Office Action in U.S. Appl. No. 10/276,712; Aug. 29, 2005; USPTO; Alexandria, Virgina; All pages.
U.S. Patent and Trademark Office; Office Action in U.S. Appl. No. 10/276,712; Nov. 14, 2005; USPTO; Alexandria, Virgina; All pages.
LDR Medical, by its attorneys; Reply to Office Action in U.S. Appl. No. 10/276,712; Jan. 17, 2006; USPTO; Alexandria, Virgina; All pages.
U.S. Patent & Trademark Office; Office Action in U.S. Appl. No. 10/276,712; Feb. 8, 2006; USPTO; Alexandria, Virgina; All pages.
LDR Medical, by its attorneys; Reply to Office Action in U.S. Appl. No. 10/276,712; Mar. 14, 2006; USPTO; Alexandria, Virgina; All pages.
U.S. Patent & Trademark Office; Office Action in U.S. Appl. No. 10/276,712; Jun. 7, 2006; USPTO; Alexandria, Virgina; All pages.
LDR Medical, by its attorneys; Reply to Office Action in U.S. Appl. No. 10/276,712; Oct. 6, 2006; USPTO; Alexandria, Virgina; All pages.
U.S. Patent & Trademark Office; Office Action in U.S. Appl. No. 10/276,712; Dec. 20, 2006; USPTO; Alexandria, Virgina; All pages.
LDR Medical, by its attorneys; Reply to Office Action in U.S. Appl. No. 10/276,712; Jun. 19, 2007; USPTO; Alexandria, Virgina; All pages.
U.S. Patent & Trademark Office; Notice of Allowance in U.S. Appl. No. 10/276,712; Jul. 30, 2007; USPTO; Alexandria, Virgina; All pages.
U.S. Patent & Trademark Office; Office Action in U.S. Appl. No. 11/767,386; Dec. 24, 2009; USPTO; Alexandria, Virgina; All pages.
LDR Medical, by its attorneys; Reply to Office Action in U.S. Appl. No. 11/767,386; Apr. 26, 2010; USPTO; Alexandria, Virgina; All pages.
U.S. Patent & Trademark Office; Office Action in U.S. Appl. No. 11/767,386; Jul. 21, 2010; USPTO; Alexandria, Virgina; All pages.
LDR Medical, by its attorneys; Reply to Office Action in U.S. Appl. No. 11/767,386; Jan. 21, 2011; USPTO; Alexandria, Virgina; All pages.
U.S. Patent & Trademark Office; Office Action in U.S. Appl. No. 11/767,386; Mar. 24, 2011; USPTO; Alexandria, Virgina; All pages.
LDR Medical, by its attorneys; Reply to Office Action in U.S. Appl. No. 11/767,386; Sep. 26, 2011; USPTO; Alexandria, Virgina; All pages.
U.S. Patent & Trademark Office; Restriction Requirement in U.S. Appl. No. 11/378,165; Sep. 28, 2007; USPTO; Alexandria, Virgina; All pages.
LDR Medical, by its attorneys; Reply to Restriction Requirement in U.S. Appl. No. 11/378,165; Feb. 28, 2008; USPTO; Alexandria, Virgina; All pages.
U.S. Patent & Trademark Office; Office Action in U.S. Appl. No. 11/378,165; May 27, 2008; USPTO; Alexandria, Virgina; All pages.
LDR Medical, by its attorneys; Reply to Office Action in U.S. Appl. No. 11/378,165; Nov. 26, 2008; USPTO; Alexandria, Virgina; All pages.
U.S. Patent & Trademark Office; Office Action in U.S. Appl. No. 11/378,165; Feb. 17, 2009; USPTO; Alexandria, Virgina; All pages.
LDR Medical, by its attorneys; Reply to Office Action in U.S. Appl. No. 11/378,165; Aug. 4, 2009; USPTO; Alexandria, Virgina; All pages.
U.S. Patent & Trademark Office; Office Action in U.S. Appl. No. 11/378,165; Aug. 11, 2009; USPTO; Alexandria, Virgina; All pages.
LDR Medical, by its attorneys; Request for Continued Examination in U.S. Appl. No. 11/378,165; Aug. 14, 2009; USPTO; Alexandria, Virgina; All pages.
U.S. Patent & Trademark Office; Office Action in U.S. Appl. No. 11/378,165; Oct. 26, 2009; USPTO; Alexandria, Virgina; All pages.

LDR Medical, by its attorneys; Reply to Office Action in U.S. Appl. No. 11/378,165; Apr. 26, 2010; USPTO; Alexandria, Virgina; All pages.

U.S. Patent & Trademark Office; Examiner's Interview Summary in U.S. Appl. No. 11/378,165; May 20, 2010; USPTO; Alexandria, Virgina; All pages.

LDR Medical, by its attorneys; Applicant's Interview Summary in U.S. Appl. No. 11/378,165; Jun. 18, 2010; USPTO; Alexandria, Virgina; All pages.

U.S. Patent & Trademark Office; Office Action in U.S. Appl. No. 11/378,165; Sep. 24, 2010; USPTO; Alexandria, Virgina; All pages.

LDR Medical, by its attorneys; Reply to Office Action in U.S. Appl. No. 11/378,165; Mar. 24, 2011; USPTO; Alexandria, Virgina; All pages.

U.S. Patent & Trademark Office; Office Action in U.S. Appl. No. 11/378,165; Jun. 4, 2012; USPTO; Alexandria, Virgina; All pages.

LDR Medical; ROI Privilegier la greffe en creant la chambre de fusion; Sep. 19, 2004; LDR Medical; France; all pages, one page.

LDR Medical; Mc+ Le choix de l'ancrage; Sep. 19, 2004; LDR Medical; France; all pages, one page.

LDR Medical; Greffe et fusion; Sep. 19, 2004; LDR Medical; France; all pages, one page.

U.S. Patent & Trademark Office; Office Action in U.S. Appl. No. 10/476,565; Jul. 18, 2006; USPTO; Alexandria, Virgina; All pages.

LDR Medical, by its attorneys; Reply to Office Action in U.S. Appl. No. 10/476,565; Jan. 18, 2007; USPTO; Alexandria, Virgina; All pages.

U.S. Patent & Trademark Office; Office Action in U.S. Appl. No. 10/476,565; May 7, 2007; USPTO; Alexandria, Virgina; All pages.

LDR Medical, by its attorneys; Reply to Office Action in U.S. Appl. No. 10/476,565; Nov. 6, 2007; USPTO; Alexandria, Virgina; All pages.

U.S. Patent & Trademark Office; Notice of Allowance in U.S. Appl. No. 10/476,565; Nov. 29, 2007; USPTO; Alexandria, Virgina; All pages.

LDR Medical, by its attorneys; Amendment after Final in U.S. Appl. No. 10/476,565; Nov. 29, 2007; USPTO; Alexandria, Virgina; All pages.

U.S. Patent & Trademark Office; Office Action in U.S. Appl. No. 12/025,677; Oct. 7, 2011; USPTO; Alexandria, Virgina; All pages.

LDR Medical, by its attorneys; Reply to Office Action in U.S. Appl. No. 12/025,677; Apr. 9, 2012; USPTO; Alexandria, Virgina; All pages.

U.S. Patent & Trademark Office; Office Action in U.S. Appl. No. 12/025,677; Jun. 29, 2012; USPTO; Alexandria, Virgina; All pages.

U.S. Patent & Trademark Office; Notice of Allowance in U.S. Appl. No. 10/494,418; Sep. 20, 2005; USPTO; Alexandria, Virgina; All pages.

U.S. Patent & Trademark Office; Notice of Allowance in U.S. Appl. No. 10/533,846; Nov. 4, 2009; USPTO; Alexandria, Virgina; All pages.

U.S. Patent & Trademark Office; Office Action in U.S. Appl. No. 12/424,364; May 18, 2011; USPTO; Alexandria, Virgina; All pages.

LDR Medical, by its attorneys; Reply to Office Action in U.S. Appl. No. 12/424,364; Nov. 18, 2011; USPTO; Alexandria, Virgina; All pages.

U.S. Patent & Trademark Office; Office Action in U.S. Appl. No. 12/424,364; Jan. 26, 2012; USPTO; Alexandria, Virgina; All pages.

LDR Medical, by its attorneys; Reply to Office Action in U.S. Appl. No. 12/424,364; Feb. 27, 2012; USPTO; Alexandria, Virgina; All pages.

LDR Medical, by its attorneys; Interview Summary and Terminal Disclaimer in U.S. Appl. No. 12/424,364; May 22, 2012; USPTO; Alexandria, Virgina; All pages.

U.S. Patent & Trademark Office; Office Action in U.S. Appl. No. 12/424,364; May 23, 2012; USPTO; Alexandria, Virgina; All pages.

LDR Medical, by its attorneys; Reply to Office Action in U.S. Appl. No. 12/424,364; Jul. 6, 2012; USPTO; Alexandria, Virgina; All pages.

U.S. Patent & Trademark Office; Notice of Allowance in U.S. Appl. No. 12/424,364; Jul. 24, 2012; USPTO; Alexandria, Virgina; All pages.

World Intellectual Property Organization; Written Opinon of the International Searching Authority for PCT Pub'n. No. WO2005074839; Jun. 24, 2005; WIPO; Geneva, Switzerland; all pages.

World Intellectual Property Organization; International Preliminary Report on Patentability for PCT Pub'n. No. WO2005074839; Jan. 16, 2006; WIPO; Geneva, Switzerland; all pages.

U.S. Patent & Trademark Office; Office Action in U.S. Appl. No. 11/051,710; Oct. 26, 2009; USPTO; Alexandria, Virgina; All pages.

LDR Medical, by its attorneys; Reply to Office Action in U.S. Appl. No. 11/051,710; Apr. 26, 2010; USPTO; Alexandria, Virgina; All pages.

U.S. Patent & Trademark Office; Office Action in U.S. Appl. No. 11/051,710; Jul. 20, 2010; USPTO; Alexandria, Virgina; All pages.

LDR Medical, by its attorneys; Reply to Office Action in U.S. Appl. No. 11/051,710; Jan. 20, 2011; USPTO; Alexandria, Virgina; All pages.

U.S. Patent & Trademark Office; Office Action in U.S. Appl. No. 11/051,710; Apr. 11, 2011; USPTO; Alexandria, Virgina; All pages.

LDR Medical, by its attorneys; Reply to Office Action in U.S. Appl. No. 11/051,710; Oct. 11, 2011; USPTO; Alexandria, Virgina; All pages.

U.S. Patent & Trademark Office; Office Action in U.S. Appl. No. 11/051,710; Dec. 15, 2011; USPTO; Alexandria, Virgina; All pages.

World Intellectual Property Organization; Written Opinon of the International Searching Authority for PCT Pub'n. No. WO2005104996; Sep. 12, 2005; WIPO; Geneva, Switzerland; all pages.

U.S. Patent & Trademark Office; Office Action in U.S. Appl. No. 11/098,766; Mar. 22, 2006; USPTO; Alexandria, Virgina; All pages.

World Intellectual Property Organization; International Preliminary Report on Patentability for PCT Pub'n No. WO2005104996; Jun. 28, 2006; WIPO; Geneva, Switzerland; all pages.

LDR Medical, by its attorneys; Reply to Office Action in U.S. Appl. No. 11/098,266; Aug. 22, 2006; USPTO; Alexandria, Virgina; All pages.

U.S. Patent & Trademark Office; Office Action in U.S. Appl. No. 11/098,266; Nov. 29, 2006; USPTO; Alexandria, Virgina; All pages.

LDR Medical, by its attorneys; Reply to Office Action in U.S. Appl. No. 11/098,266; May 23, 2007; USPTO; Alexandria, Virgina; All pages.

U.S. Patent & Trademark Office; Office Action in U.S. Appl. No. 11/098,266; Aug. 6, 2007; USPTO; Alexandria, Virgina; All pages.

LDR Medical, by its attorneys; Reply to Office Action in U.S. Appl. No. 11/098,266; Feb. 6, 2008; USPTO; Alexandria, Virgina; All pages.

U.S. Patent & Trademark Office; Notice of Allowance in U.S. Appl. No. 11/098,266; Apr. 21, 2008; USPTO; Alexandria, Virgina; All pages.

U.S. Patent & Trademark Office; Office Action in U.S. Appl. No. 12/391,086; Jul. 29, 2010; USPTO; Alexandria, Virgina; All pages.

LDR Medical, by its attorneys; Reply to Office Action in U.S. Appl. No. 12/391,086; Jan. 31, 2011; USPTO; Alexandria, Virgina; All pages.

U.S. Patent & Trademark Office; Notice of Allowance in U.S. Appl. No. 12/391,086; Apr. 15, 2011; USPTO; Alexandria, Virgina; All pages.

National Institute of Industrial Property (France); Preliminary Search Report in Fench Pub. No. FR2887762; Dec. 21, 2005; National Institute of Industrial Property (France); France; all pages.

World Intellectual Property Organization; Written Opinon of the International Searching Authority for PCT Pub'n No. WO2007000654; Mar. 14, 2007; WIPO; Geneva, Switzerland; all pages.

World Intellectual Property Organization; International Search Report for PCT Pub'n No. WO2007000654; Mar. 14, 2007; WIPO; Geneva, Switzerland; all pages.

World Intellectual Property Organization; International Preliminary Report on Patentability for PCT Pub'n No. WO2007000654; Jul. 19, 2007; WIPO; Geneva, Switzerland; all pages.

U.S. Patent & Trademark Office; Notice of Allowance in U.S. Appl. No. 11/180,868; Jul. 17, 2009; USPTO; Alexandria, Virgina; All pages.

U.S. Patent & Trademark Office; Notice of Allowance in U.S. Appl. No. 11/180,868; Jul. 31, 2009; USPTO; Alexandria, Virgina; All pages.
U.S. Patent & Trademark Office; Office Action in U.S. Appl. No. 12/435,955; Oct. 11, 2011; USPTO; Alexandria, Virgina; All pages.
LDR Medical, by its attorneys; Reply to Office Action in U.S. Appl. No. 12/435,955; Apr. 11, 2012; USPTO; Alexandria, Virgina; All pages.
National Institute of Industrial Property (France); Preliminary Search Report in Fench Pub. No. FR2891135; Jun. 27, 2006; National Institute of Industrial Property (France); France; all pages.
World Intellectual Property Organization; Written Opinon of the International Searching Authority for PCT Pub'n No. WO2007034310; Feb. 13, 2007; WIPO; Geneva, Switzerland; all pages.
World Intellectual Property Organization; International Search Report for PCT Pub'n No. WO2007034310; Feb. 13, 2007; WIPO; Geneva, Switzerland; all pages.
World Intellectual Property Organization; International Preliminary Report on Patentability for PCT Pub'n No. WO2007034310; Aug. 14, 2007; WIPO; Geneva Switzerland; all pages.
U.S. Patent & Trademark Office; Office Action in U.S. Appl. No. 11/341,007; Apr. 13, 2009; USPTO; Alexandria, Virgina; All pages.
LDR Medical, by its attorneys; Reply to Office Action in U.S. Appl. No. 11/341,007; Oct. 13, 2009; USPTO; Alexandria, Virgina; All pages.
U.S. Patent & Trademark Office; Office Action in U.S. Appl. No. 11/341,007; Dec. 17, 2009; USPTO; Alexandria, Virgina; All pages.
LDR Medical, by its attorneys; Reply to Office Action in U.S. Appl. No. 11/341,007; Jun. 17, 2010; USPTO; Alexandria, Virgina; All pages.
U.S. Patent & Trademark Office; Notice of Allowance in U.S. Appl. No. 11/341,007; Jul. 26, 2010; USPTO; Alexandria, Virgina; All pages.
U.S. Patent & Trademark Office; Office Action in U.S. Appl. No. 12/955,898; Mar. 19, 2012; USPTO; Alexandria, Virgina; All pages.
LDR Medical, by its attorneys; Reply to Office Action in U.S. Appl. No. 12/955,898; Apr. 19, 2012; USPTO; Alexandria, Virgina; All pages.
U.S. Patent & Trademark Office; Office Action in U.S. Appl. No. 12/955,898; Jun. 1, 2012; USPTO; Alexandria, Virgina; All pages.
National Institute of Industrial Property (France); Preliminary Search Report in Fench Pub. No. FR2893838; Aug. 4, 2006; National Institute of Industrial Property (France); France; all pages.
World Intellectual Property Organization; Written Opinon of the International Searching Authority for PCT Pub'n No. WO2007063398; Jul. 13, 2007; WIPO; Geneva, Switzerland; all pages.
World Intellectual Property Organization; International Search Report for PCT Pub'n No. WO2007063398; Jul. 13, 2007; WIPO; Geneva, Switzerland; all pages.
World Intellectual Property Organization; International Preliminary Report on Patentability for PCT Pub'n No. WO2007063398; Nov. 12, 2007; WIPO; Geneva, Switzerland; all pages.
U.S. Patent & Trademark Office; Office Action in U.S. Appl. No. 11/362,253; Feb. 18, 2009; USPTO; Alexandria, Virgina; All pages.
LDR Medical, by its attorneys; Reply to Office Action in U.S. Appl. No. 11/362,253; Aug. 18, 2009; USPTO; Alexandria, Virgina; All pages.
U.S. Patent & Trademark Office; Office Action in U.S. Appl. No. 11/362,253; Oct. 15, 2009; USPTO; Alexandria, Virgina; All pages.
LDR Medical, by its attorneys; Reply to Office Action in U.S. Appl. No. 11/362,253; Apr. 15, 2010; USPTO; Alexandria, Virgina; All pages.
U.S. Patent & Trademark Office; Office Action in U.S. Appl. No. 11/362,253; Jun. 18, 2010; USPTO; Alexandria, Virgina; All pages.
LDR Medical, by its attorneys; Reply to Office Action in U.S. Appl. No. 11/362,253; Dec. 20, 2010; USPTO; Alexandria, Virgina; All pages.
U.S. Patent & Trademark Office; Office Action in U.S. Appl. No. 11/362,253; Mar. 8, 2011; USPTO; Alexandria, Virgina; All pages.
LDR Medical, by its attorneys; Appeal Brief in U.S. Appl. No. 11/362,253; Apr. 9, 2012; USPTO; Alexandria, Virgina; All pages.
U.S. Patent & Trademark Office; Examiners Answer to Appeal Brief in U.S. Appl. No. 11/362,253; Jun. 20, 2012; USPTO; Alexandria, Virgina; All pages.
U.S. Patent & Trademark Office; Office Action in U.S. Appl. No. 11/676,237; Mar 20, 2009; USPTO; Alexandria, Virgina; All pages.
LDR Medical, by its attorneys; Reply to Office Action in U.S. Appl. No. 11/676,237; Sep. 21, 2009; USPTO; Alexandria, Virgina; All pages.
U.S. Patent & Trademark Office; Office Action in U.S. Appl. No. 11/676,237; Dec. 18, 2009; USPTO; Alexandria, Virgina; All pages.
LDR Medical, by its attorneys; Reply to Office Action in U.S. Appl. No. 11/676,237; Jun. 18, 2010; USPTO; Alexandria, Virgina; All pages.
U.S. Patent & Trademark Office; Office Action in U.S. Appl. No. 11/676,237; Sep. 15, 2010; USPTO; Alexandria, Virgina; All pages.
LDR Medical, by its attorneys; Appeal Brief in U.S. Appl. No. 11/676,237; Oct. 17, 2011; USPTO; Alexandria, Virgina; All pages.
U.S. Patent & Trademark Office; Office Action in U.S. Appl. No. 11/676,237; Feb. 16, 2012; USPTO; Alexandria, Virgina; All pages.
LDR Medical, by its attorneys; Reply to Office Action in U.S. Appl. No. 12/424,364; Jul. 16, 2012; USPTO; Alexandria, Virgina; All pages.
LDR Medical, by its attorneys; Reply to Office Action in U.S. Appl. No. 12/527,373; Jun. 21, 2012; USPTO; Alexandria, Virgina; All pages.
World Intellectual Property Organization; Written Opinon of the International Searching Authority for PCT Pub'n No. WO2008099277; Nov. 7, 2008; WIPO; Geneva, Switzerland; all pages.
World Intellectual Property Organization; International Search Report for PCT Pub'n No. WO2008099277; Nov. 7, 2008; WIPO; Geneva, Switzerland; all pages.
World Intellectual Property Organization; International Preliminary Report on Patentability for PCT Pub'n No. WO2008099277; May 29, 2009; WIPO; Geneva, Switzerland; all pages.
U.S. Patent & Trademark Office; Office Action in U.S. Appl. No. 12/527,373; Dec. 21, 2011; USPTO; Alexandria, Virgina; All pages.

* cited by examiner

FIGURE 1A
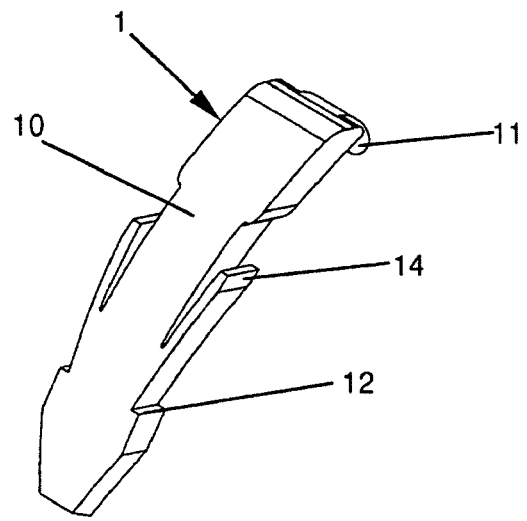
FIGURE 1B
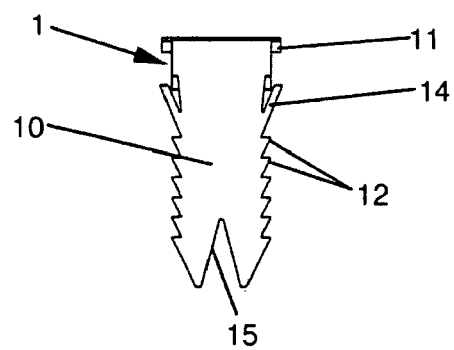
FIGURE 1C                FIGURE 1D
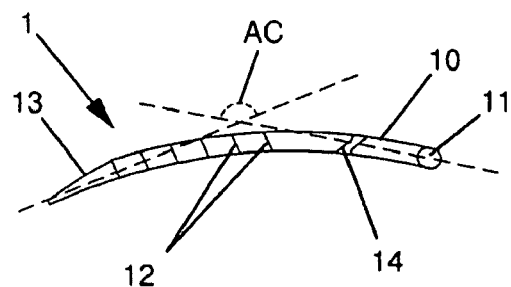   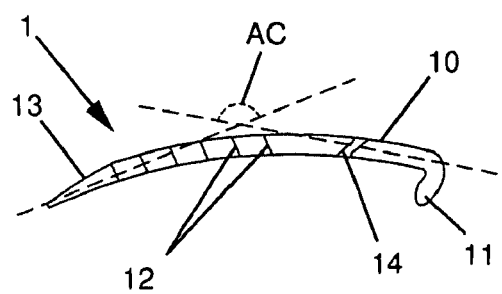

INTERSOMATIC CAGE, INTERVERTEBRAL PROSTHESIS, ANCHORING DEVICE AND IMPLANTATION INSTRUMENTS

RELATED APPLICATIONS

This application claims priority under 35 U.S.C. §119 to French Patent Application No. 07 04155, filed in FRANCE on Jun. 8, 2007.

TECHNICAL FIELD

This present invention concerns the area of orthopedic implants and more precisely of spinal implants, such as intervertebral prostheses and intersomatic cages.

BACKGROUND

An intervertebral prosthesis is implanted between two adjacent vertebrae in order to maintain or restore a space between the vertebrae while also preserving good mobility. An intersomatic cage is implanted between two adjacent vertebrae to allow the insertion and the growth of grafts of bony tissue (or a substitute) in the disc space, in order to achieve an arthrodesis (fusion of two vertebrae). After insertion of the cage, the intervertebral space may be filled with self-adapting spongy bone or suitable bony substitutes. The present invention concerns intervertebral prostheses and intersomatic cages for intervertebral fusion grafting and their attachment to the vertebrae by a bony anchoring device and their implantation in the disc space using implantation instruments.

A problem in this area concerns the stability of the intervertebral prostheses or of the intersomatic cages in the disc space after they have been implanted there, at least before the growth of the graft on either side of the cage and fusion with the vertebrae in the case of the intersomatic cages. For example, there exists a risk that the prosthesis or the cage will move within the intervertebral space under the effect of the stresses exerted upon it when the patient moves. The prosthesis or the cage must therefore not only have a shape that prevents it from pivoting but also have resources to prevent it from moving within the intervertebral space.

From previous designs, we know of solutions that consist of equipping the top and bottom surfaces of the prostheses or cages with notches so as to prevent movement. However, this type of solution is not perfect and the prosthesis or the cage still may move. We are also familiar, from previous designs, with solutions that consist of equipping the prosthesis or the cage with a bony anchoring device which is used to soundly attach the prosthesis or the cage to the vertebral plates of the vertebrae between which it is implanted. This type of bony anchoring device proves to be effective for securing the prosthesis or the cage. However, this type of solution presents problems during implantation.

Access to the intervertebral spaces is often particularly difficult because of the dimensions involved, and in particular due to the presence of blood vessels and nerves at the edges of the intervertebral space. The bony anchoring devices must penetrate into the vertebrae to a sufficient depth to secure the device. As a consequence, these bony anchoring devices are generally implanted along an approach axis that is more-or-less perpendicular to the plane of the intervertebral space or at least on a substantially oblique axis in relation to the plane of the intervertebral space. Other types of bony anchoring devices fit onto a plate that is substantially parallel to the axis of the vertebral column and extending the prosthesis or the cage on one of the faces of the vertebrae. These different types of device therefore require the surgeons to make large incisions, inducing prejudice and considerable risks for the patient. In addition, this type of bony anchoring device is not easy to implant since it requires that there is sufficient space at the edges of the intervertebral space to allow the implantation of the device, which unfortunately is not always the case, depending on the vertebrae in question.

In this context, it is useful to provide an anchoring device (which may be referenced below simply as a "device") for an intersomatic cage or an intervertebral disc prosthesis that reduces the space at the edges of the intervertebral space that is necessary for the implantation of the cage itself, that makes the application of the anchoring device more convenient, or that provides better anchoring than some of the known anchoring means.

SUMMARY

Some embodiments of this present invention have a purpose of overcoming certain drawbacks of some previous designs by providing an anchoring device that is implanted solidly and at a sufficient depth in the vertebral plates to retain the cage against these vertebrae, but on an approach axis that is substantially along the plane of the intervertebral space.

Some embodiments of this present invention have a purpose of overcoming certain drawbacks of some previous designs by providing an intersomatic cage that is implantable substantially along the plane of the intervertebral space, which may be attached to the vertebrae by means of an anchoring device that is implantable substantially along the plane of the intervertebral space.

Some embodiments of this present invention have a purpose of overcoming certain drawbacks of some previous designs by providing an intervertebral prosthesis that is implantable substantially along the plane of the intervertebral space, which may be solidly attached to the vertebrae by means of an anchoring device that is implantable substantially along the plane of the intervertebral space.

Some embodiments of this present invention have a purpose of overcoming certain drawbacks of some previous designs by providing an instrument for the implantation of an intersomatic cage or an intervertebral disc prosthesis between the vertebrae and for the implantation of an anchoring device in at least one of these vertebrae, which may be used to implant the cages or the prostheses substantially along the plane of the intervertebral space and to implant an anchoring device on an approach axis that is substantially along the plane of the intervertebral space.

BRIEF DESCRIPTIONS OF THE DRAWINGS

Other particular features and advantages of various embodiments of this present invention will appear more clearly on reading the description that follows, provided with reference to the appended drawings, in which:

FIG. 1A represents a view in perspective of an anchoring device according to one method of implementation of the invention, FIG. 1B represents a view from above of an anchoring device according to another method of implementation of the invention, and FIGS. 1C and 1D represent views in profile of anchoring devices according to two different methods of implementation of the invention.

Figure 2B:
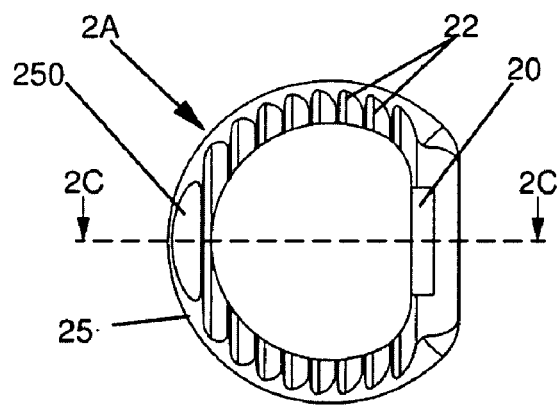
Figure 2C:
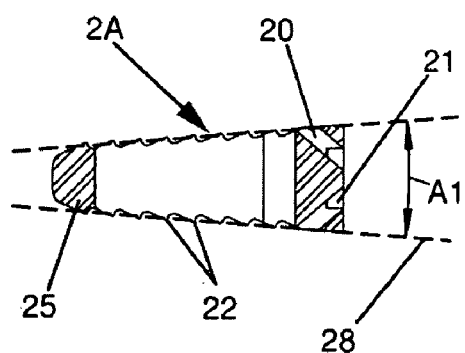
Figure 2D:
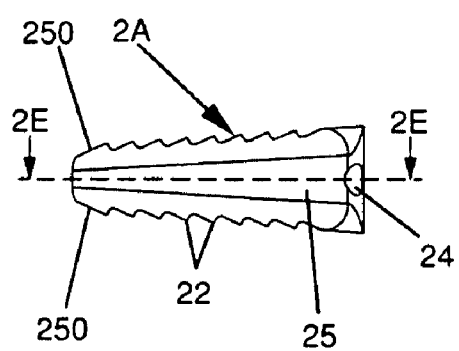
Figure 2E:
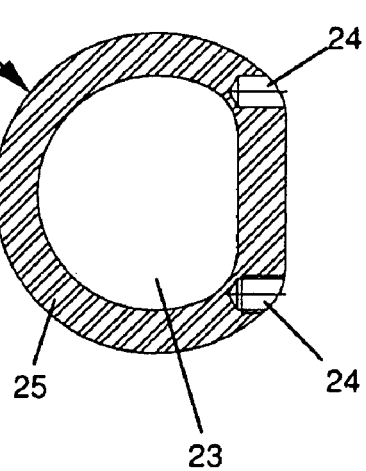

FIGS. 2A, 2B and 2D respectively represent a view in perspective, a view from above and a view in profile of an intersomatic cage according to one method of implementation of the invention, FIG. 2C represents a view in section of this intersomatic cage on section plane 2C-2C represented in FIG. 2B and FIG. 2E represents a view in section of this intersomatic cage on section plane 2E-2E represented in FIG. 2D.

Figure 3A:
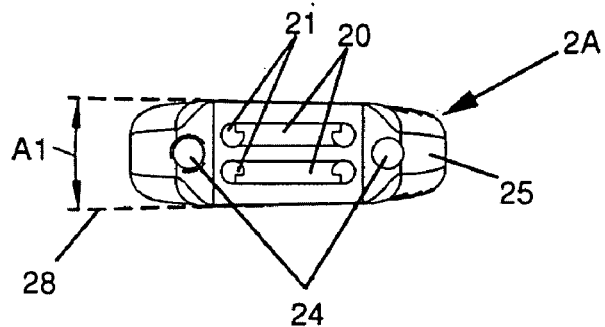
Figure 3B:
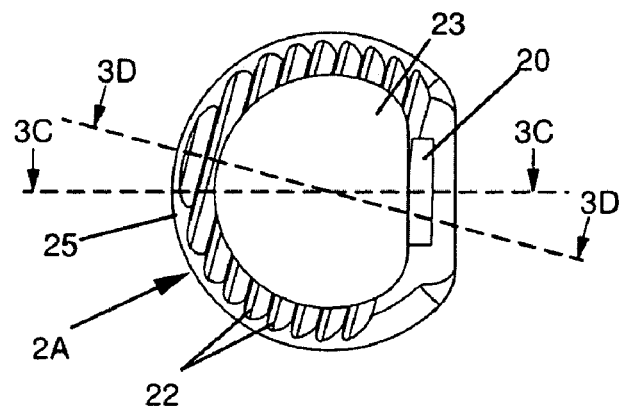
Figure 3C:
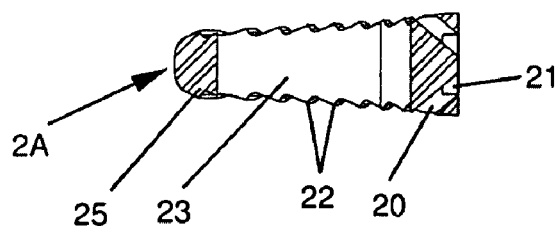
Figure 3D:
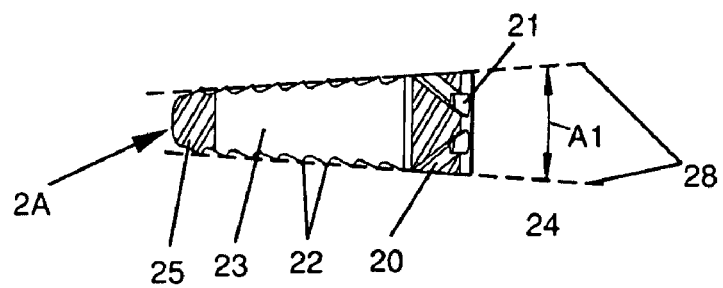

FIGS. 3A and 3B respectively represent a view in perspective from the front and a view from above of an intersomatic cage according to one method of implementation of the invention, FIG. 3C represents a view in section of this intersomatic cage on section plane 3C-3C represented in FIG. 3B and FIG. 3D represents a view in section of this intersomatic cage on section plane 3D-3D represented in FIG. 3B.

Figure 4A:
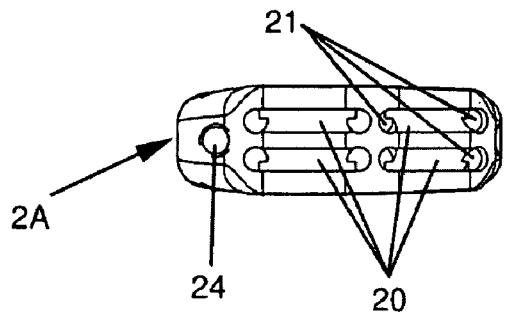
Figure 4B:
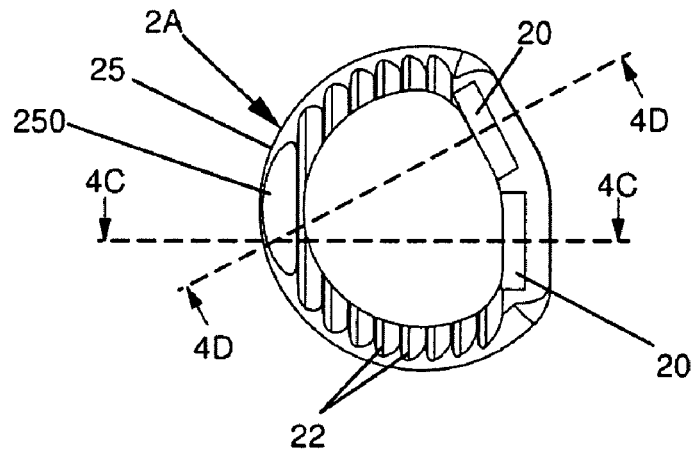
Figure 4C:
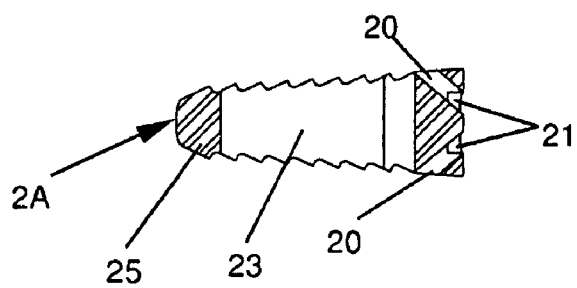
Figure 4D:
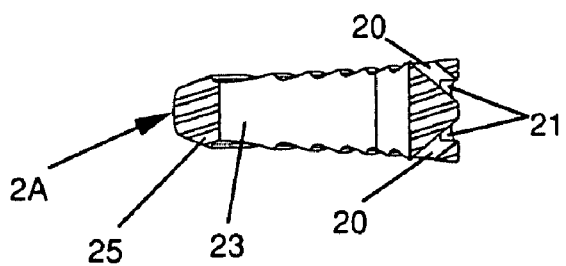

FIGS. 4A and 4B respectively represent a view in perspective from the front and a view from above of an intersomatic cage according to one method of implementation of the invention, FIG. 4C represents a view in section of this intersomatic cage on section plane 4C-4C represented in FIG. 4B, and FIG. 4D represents a view in section of this intersomatic cage on section plane 4D-4D represented in FIG. 4B.

Figure 5A:
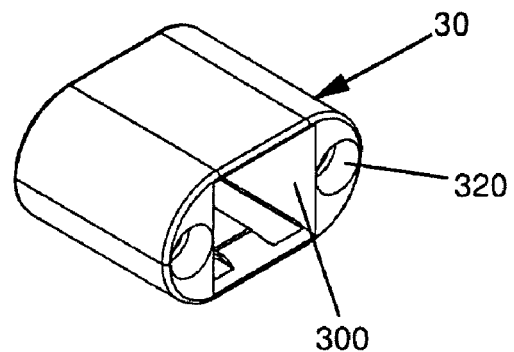
Figure 5B:
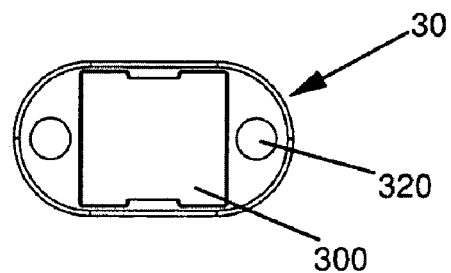
Figure 5C:
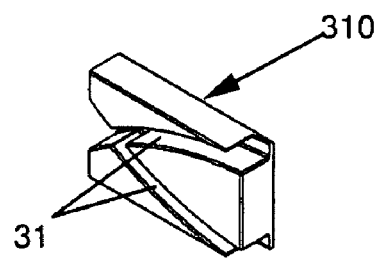
Figure 5D:
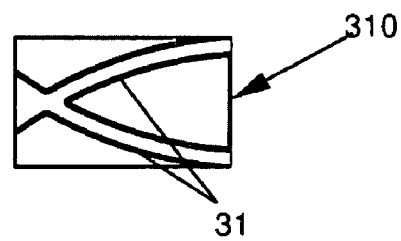
Figure 5E:
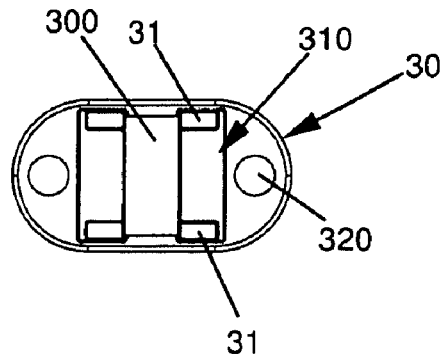

FIGS. 5A and 5B respectively represent a view in perspective and a view from the front of a head for the implantation guide of an anchoring device according to one method of implementation of the invention, FIGS. 5C and 5D respectively represent a view in perspective and a view in profile of a guidance element for an anchoring device according to one method of implementation of the invention and FIG. 5E represents a view from the front of the head of the guide equipped with two guidance elements according to one method of implementation of the invention.

Figure 6A:
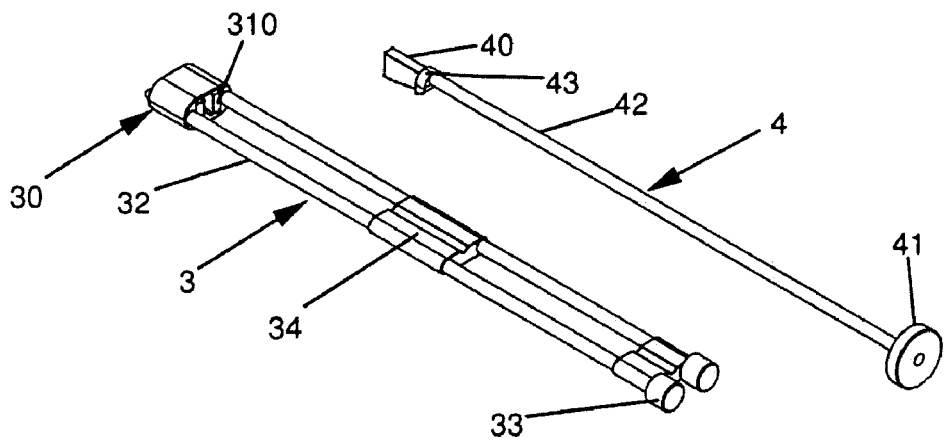
Figure 6B:
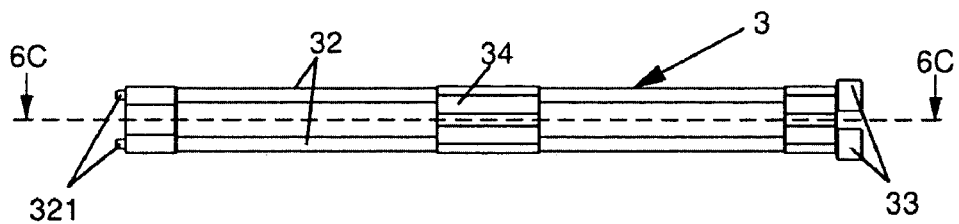
Figure 6C:
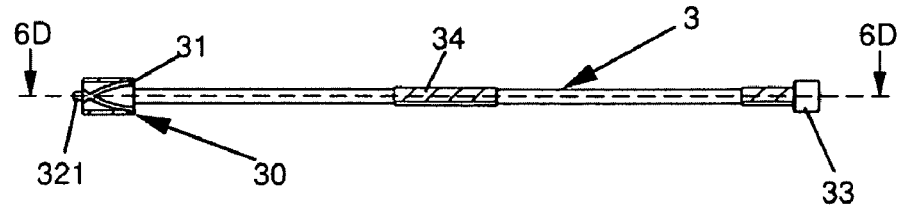
Figure 6D:
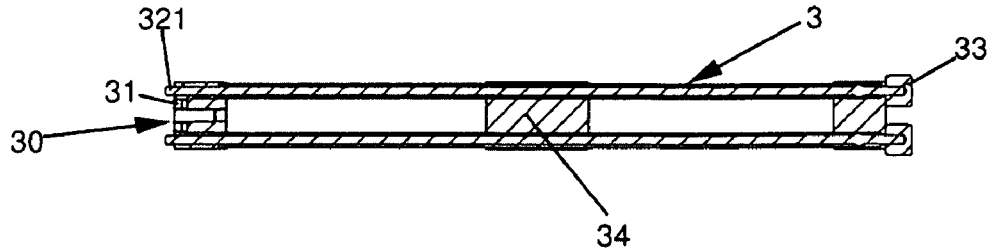
Figure 6E:
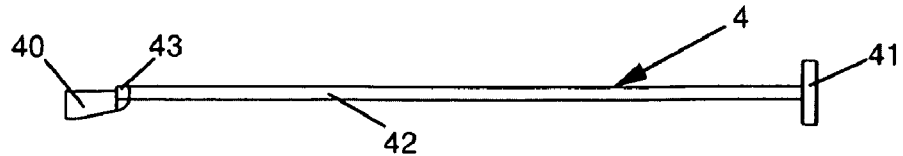

FIG. 6A represents a view in perspective of an implantation guide and of an impactor according to one method of implementation of the invention, FIGS. 6B, 6C and 6D respectively represent a view from above, a view in section on section plane 6C-6C represented in FIG. 6B and a view in section on section plane 6D-6D represented in FIG. 6C of an implantation guide according to one method of implementation of the invention and FIG. 6E represents a view in profile of an impactor according to one method of implementation of the invention.

Figure 7A:
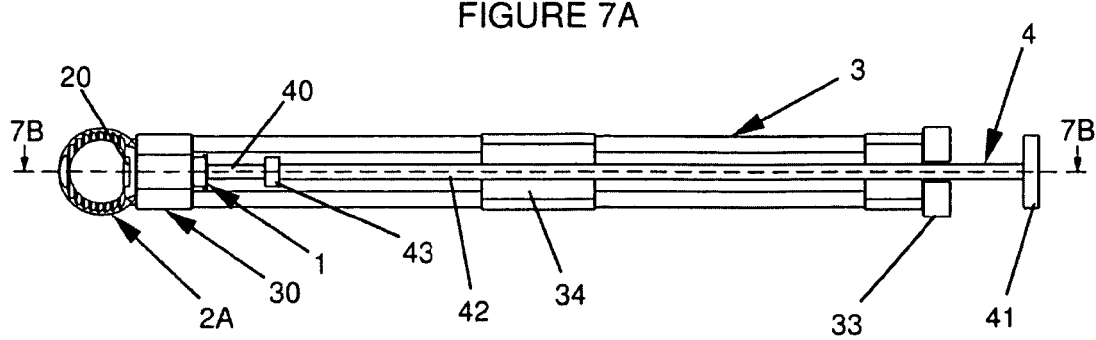
Figure 7B:
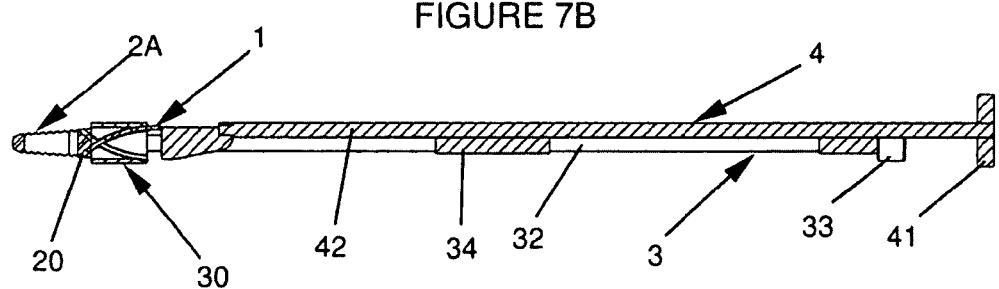
Figure 7C:
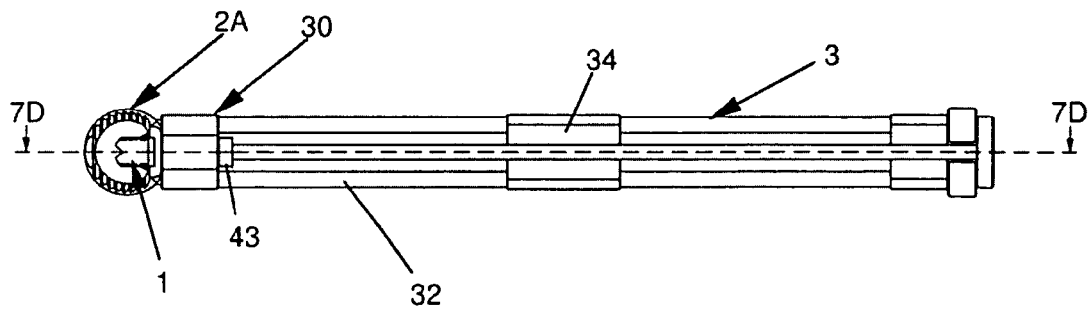
Figure 7D:
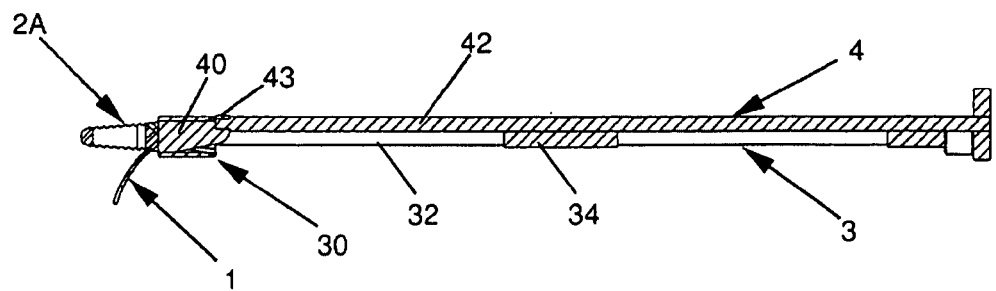

FIGS. 7A and 7C represent views from above of an assembly according to one method of implementation of the invention, of an implantation guide, of an impactor, of a cage and of an anchoring device, respectively, ready to be impacted and impacted, FIGS. 7B and 7D represent views in section of this assembly along section plane 7B-7B represented in FIG. 7A and section plane 7D-7D represented in FIG. 7C, respectively.

Figure 8A:
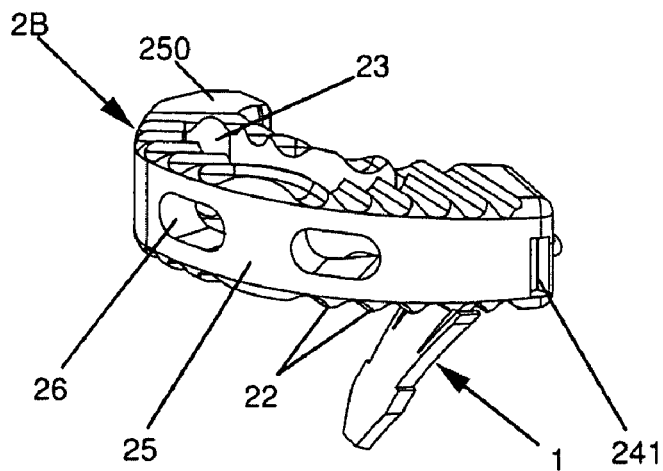
Figure 8B:
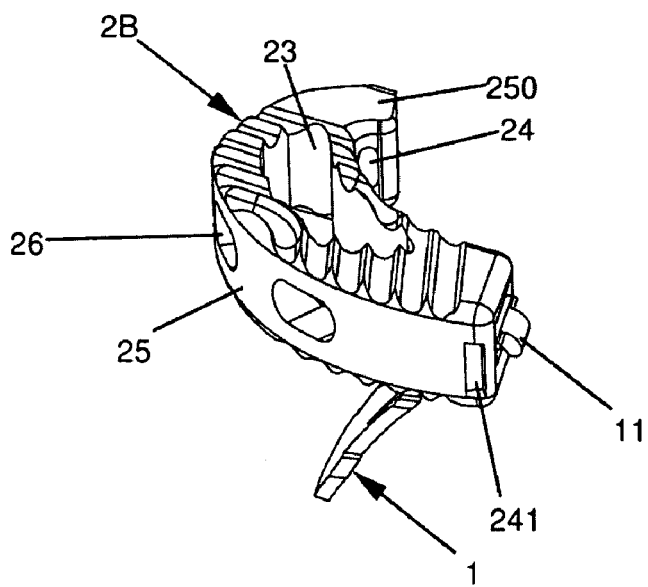
Figure 8C:
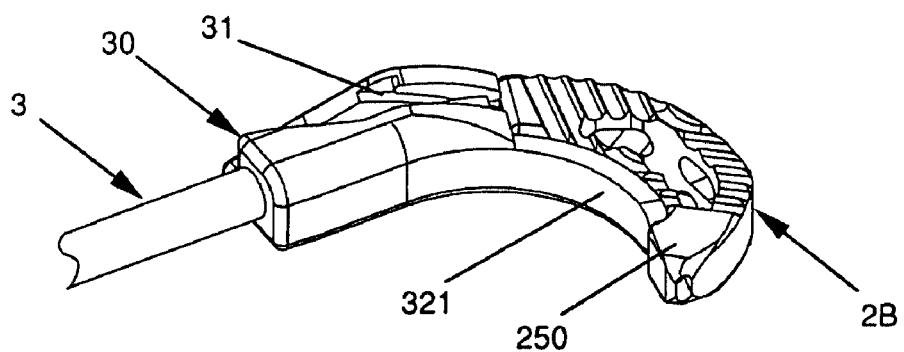

FIGS. 8A and 8B represent views in perspective of an intersomatic cage equipped with an anchoring device according to one method of implementation of the invention and FIG. 8C represents a view in perspective of the end of an implantation guide carrying an intersomatic cage according to one method of implementation of the invention.

Figure 9A:
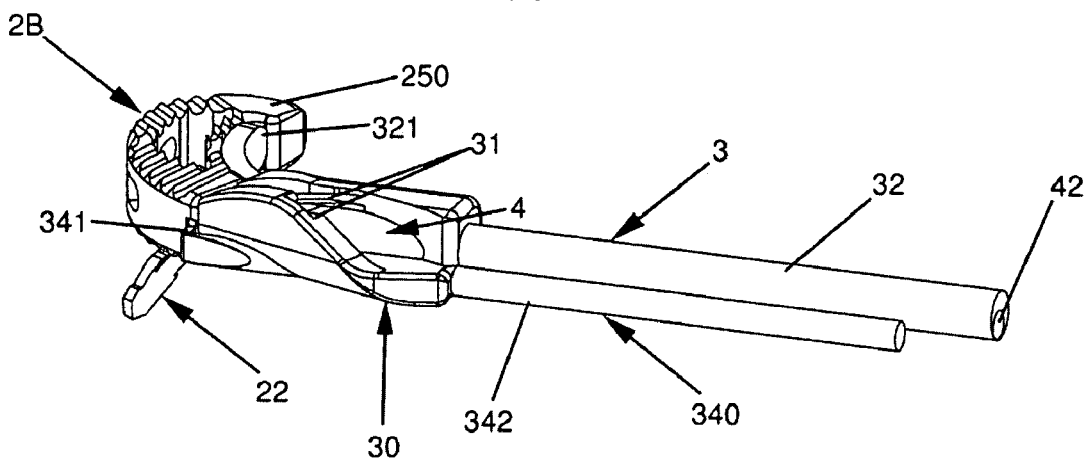
Figure 9B:
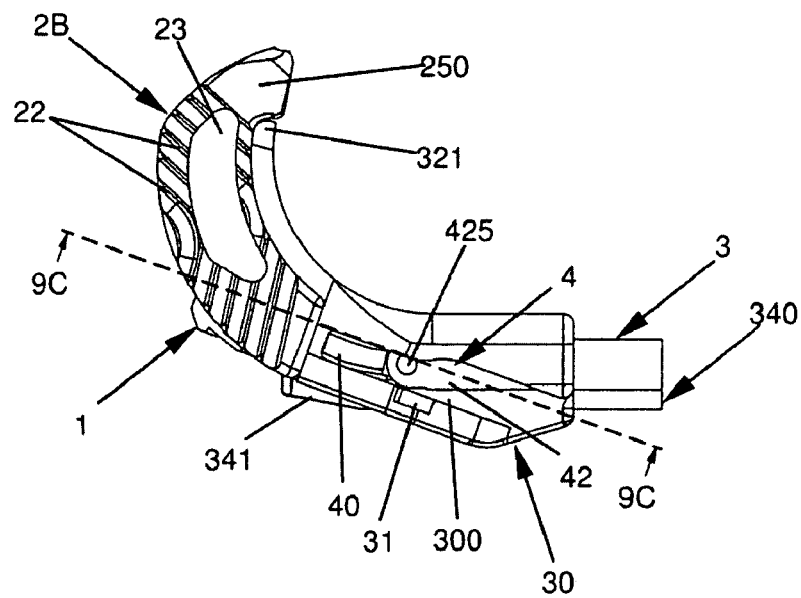
Figure 9C:
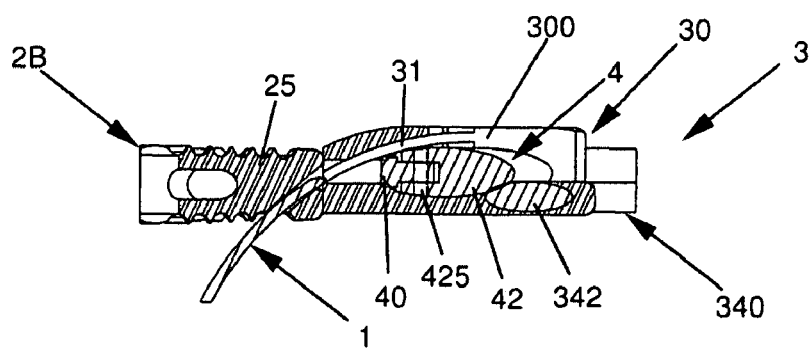

FIGS. 9A and 9B respectively represent a view in perspective and a view from above, of the end of an implantation guide carrying an intersomatic cage equipped with an anchoring device according to one method of implementation of the invention and FIG. 9C represents a view in section on section plane 9C-9C represented in FIG. 9B.

Figure 10A:
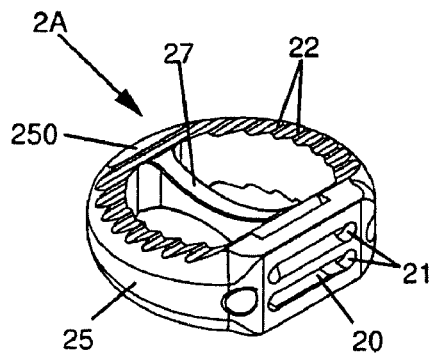
Figure 10B:
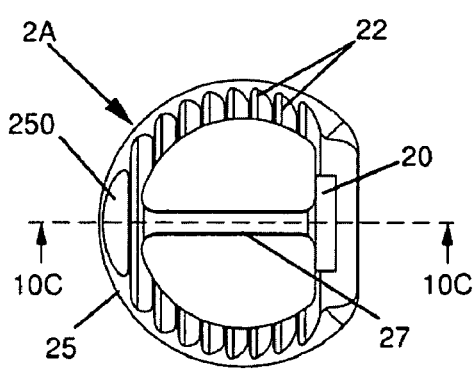
Figure 10C:
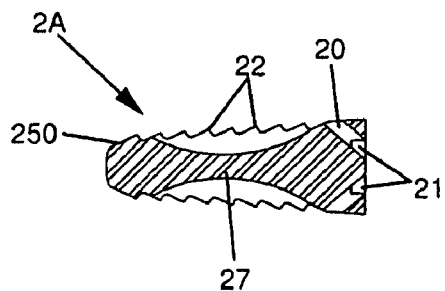
Figure 10D:
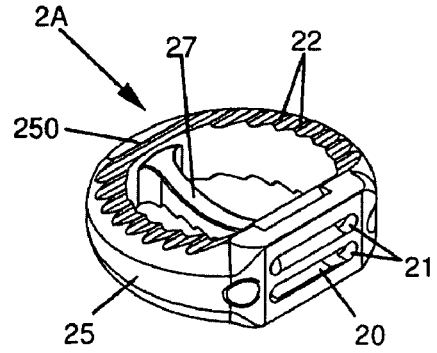
Figure 10E:
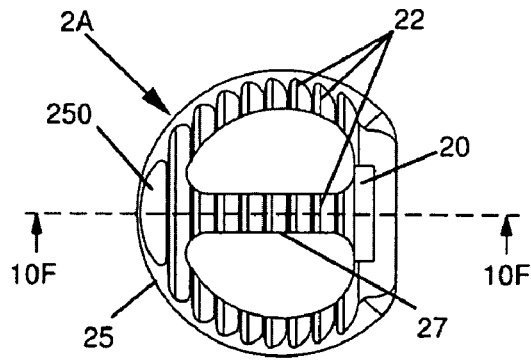
Figure 10F:
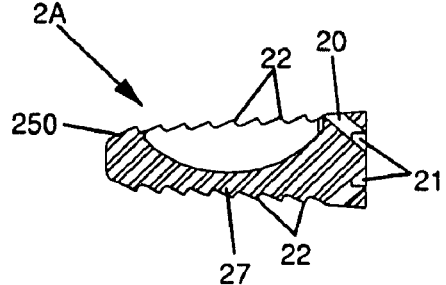

FIGS. 10A, 10B and 10C respectively represent a view in perspective, a view from above and a view in section along axis 10C-10C of FIG. 10B, of one method of implementation of a braced intersomatic cage and FIGS. 10D, 10E and 10F respectively represent a view in perspective, a view from below and a view in section along axis 10F-10F of FIG. 10E, of another method of implementation of a braced intersomatic cage.

Figure 11A:
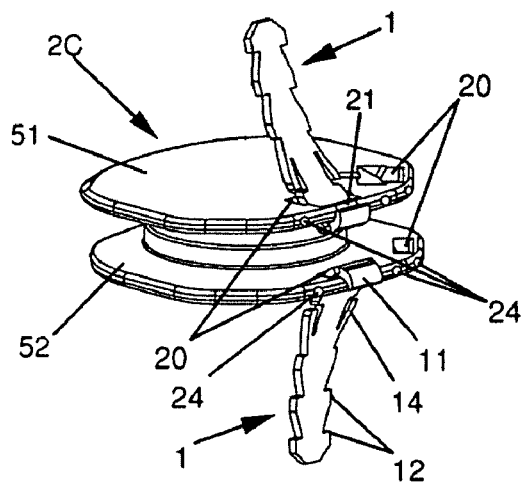
Figure 11C:
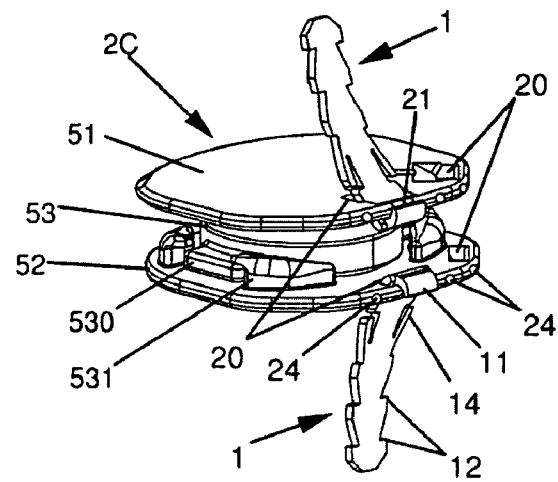
Figure 11B:
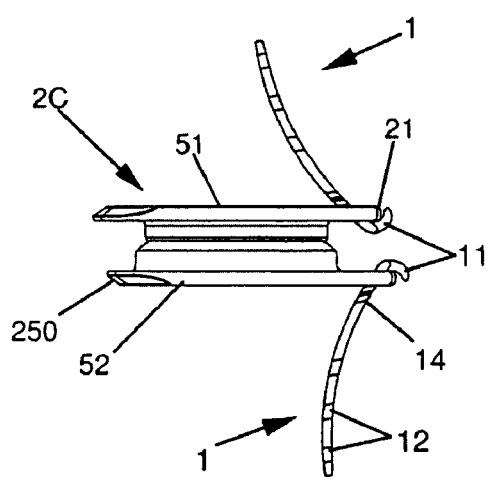
Figure 11D:
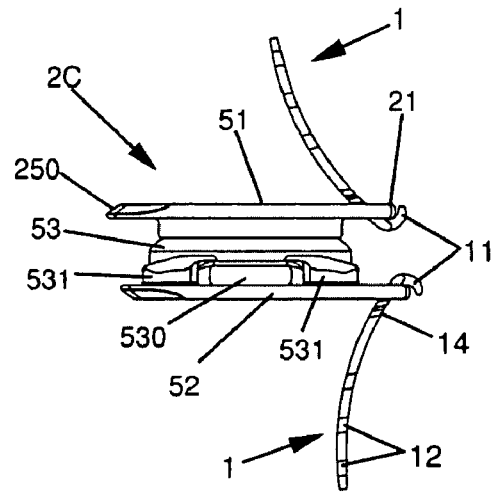

FIGS. 11A and 11B respectively represent a view in perspective and a view in profile of one method of implementation of an intervertebral prosthesis equipped with anchoring devices, and FIGS. 11C and 11D respectively represent a view in perspective and a view in profile of another method of implementation of an intervertebral prosthesis equipped with anchoring devices.

DETAILED DESCRIPTION OF VARIOUS EMBODIMENTS

This present invention concerns an anchoring device (1) that is usable for intersomatic cages (2A, 2B) or intervertebral disc prostheses (2C). In various embodiments, the anchoring device (1) fits onto at least one slot (20) located on the cage (2A, 2B) or the prosthesis (2C) that it secures. This present invention also concerns intersomatic cages (2A, 2B) and intervertebral disc prostheses (2C), which in various embodiments may have a slot (20) or other receptacles adapted to receive the anchoring device (1). This present invention also concerns an instrument for the implantation of a cage (2A, 2B) or of a prosthesis (2C) and for implantation of an anchoring device to secure the cage (2A, 2B) or the prosthesis (2C). In various embodiments, the instrument is designed for the anchoring device (1) so as to secure the latter in the vertebrae and also to the intersomatic cages (2A, 2B) or to the intervertebral disc prostheses (2C), which include at least one means (24) of retaining or attaching an implantation instrument so as to allow them to be gripped or otherwise engaged by the instrument. This attachment device may include at least one recess (24) that accommodates at least one gripping resource (321) of the instrument, as shown in the Figures and described below in greater detail. However, this attachment resource (24) may also include a portion projecting on the outside of the cage or of the prosthesis and that is inserted into a recess of a gripping resource (not shown). In addition, in certain implementation variants, this attachment resource (24) may be formed at least in part by different surfaces of the cage (2A, 2B) or of the prosthesis (2C), with the gripping resources (321) of the instrument then having a shape that is complementary to these surfaces so as to allow gripping of the cage or of the prosthesis.

Various embodiments allow a reduction in the dimensions of the device and of the associated instrument, so as to allow implantation of the anchoring device on an approach axis that is substantially along the plane of the intervertebral space (disc space).

The anchoring device (1) also may include a body (10) of elongated shape along a longitudinal axis extending between a first end and a second end. In this present description, the first end is called the penetration end and the second end is called the abutment end. The body (10) of the anchoring device (1) of various embodiments may have a curved shape that, along the longitudinal axis, describes an arc, for example a circular arc or an elliptic arc, whose dimensions and radius (or radii) of curvature are designed in such a manner that the anchoring device (1) is implantable in the vertebral plate of a vertebra by presenting the longitudinal axis of the device (1) approximately along the plane of the intervertebral space. Various implementation variants may feature a differing radius (or radii) of curvature of the anchoring device (1). The device also may have several different radii of curvature on different portions of the body (10), or may have a radius of curvature that varies along the body (10). Thus, this body may, for example, have a shape of a circular arc or of an elliptic arc, but may also describe a more complex curvature, such as if several circular arcs, having the same radius of curvature or different radii of curvature, were end to end or if several elliptic arcs, having the same radius of curvature or different radii of curvature, were end to end, or even any combination thereof, or even a radius of curvature that is a function of position along the body. In the present description, the terms "arc," "circular arc," and "radius of curvature" correspond to all these possibilities.

Accordingly, some embodiments of this present invention provide different implementation variants regarding the radius of curvature of the anchoring device (1). For example, depending on the use of the device (1), and in particular of the vertebrae between which the cage or the prosthesis is to be implanted, the device (1) preferably may have a radius of curvature that is greater or smaller in dimension in various places. Depending on the radius of curvature of the anchoring device (1), the axes passing respectively through the penetration end and through the abutment end of the device (1) form an angle (AC), as may be seen particularly in FIGS. 1C and 1D. This angle (AC) typically will be in the range of 90° to 180°, inclusively, although it may also be chosen to be less than 90°. Preferably, the angle (AC) will be between 110° and 160°, which in many circumstances will facilitate the implantation of the device better than an angle (AC) outside this range. Depending on the securing arrangement desired, an angle (AC) may be chosen that is substantially open. For example, if it is desired to secure the cage or the prosthesis by flattening it solidly against the vertebral plates, an angle (AC) will be chosen that ranges from 120° to 180°, while if instead it is desired to secure the cage or the prosthesis so as to prevent its movement in the plane of the disc space, an angle (AC) will be chosen that is between 90° and 150°. Different implementation variants may provide different angles for the anchoring device (1) to secure the cage or the prosthesis. In one of the preferred methods of implementation, angle (AC) may have a mutually accommodating value, such as close to 135°, for example, for securing the device by both flattening the cage or the prosthesis against a vertebral plate and inhibiting the movement of the cage or the prosthesis in the plane of the disc space.

In addition, depending on the method of implementation of the cage or of the prosthesis, it is possible to choose different angles for the device, in particular to promote secure fixing despite a natural or pathological lordosis or one imposed by the prosthesis. The anchoring device (1) may be inserted through a slot (20) located on at least one peripheral wall of the cage (2A, 2B) or on at least one plate of the intervertebral disc prosthesis (2C) and traverse at least one portion of this cage (2A, 2B) or of this prosthesis (2C). This slot (20) may extend from a peripheral surface of the wall (25) of the cage (2A, 2B) or of the plate of the prosthesis (2C) up to a top or bottom surface of this cage (2A, 2B) or of this plate, with an orientation designed for the radius of curvature of the anchoring device (1), so as to orientate the latter in the direction of the vertebral plate of one of the vertebrae between which the cage (2A, 2B) or the prosthesis is implanted. By means of this orientation of the slot (20), the anchoring device (1) may penetrate into at least one vertebral plate and secure the cage (2A, 2B) or the prosthesis (2C) against this vertebral plate. Depending on the radius of curvature and the angle (AC) of the anchoring device (1), the thickness and the orientation of the slot (20) may vary in accordance with the various methods of implementation.

Some embodiments of this present invention therefore provide an intersomatic cage (2A, 2B) that includes a peripheral wall (25) forming a cavity (23) that receives a graft of bony tissue or a substitute. Such a cage may include a cavity (23) in its centre, formed by its wall (25), as shown in the Figures, but it may also, in other implementation variants, consist of a block that does not have a cavity inside it, such cage being, for example, used at least in pairs, so as to form a cavity between the cages as is known from the previous designs. In an implementation variant represented in FIG. 10A, the intersomatic cage (2A) includes a brace (27) traversing its cavity (23) from side to side, which may be configured to strengthen the wall (25) of the cage (2A). This brace (27) may have different forms and orientations and may, for example, be orientated along the insertion axis of the cage (2A) between the vertebrae. In various methods of implementation, the brace (27) may have a height that is less than that of the rest of the cage. This smaller height of the brace (27) in relation to the rest of the cage may allow the cage to hug any shape irregularities of the vertebral plates. Thus, as illustrated, for example, in FIGS. 10A to 10C, the top and bottom surfaces of the brace (27) are located lower and higher than the top and bottom surfaces, respectively, of the cage (2A). Thus, if the vertebral plates of the two adjacent vertebrae have bumps, the cage will follow the shape of these plates and generally provide better stability. In this implementation example represented in FIGS. 10A to 10C, the brace is not equipped with notches since it will not be in contact with the vertebral plates. However, the brace (27) may nevertheless be equipped with notches (22), even in this case, for example, so as to enhance stability of the cage when the osseous graft has grown around the cage. In the implementation example of FIGS. 10D to 10F, the bottom surface of the brace (27) is located at the same level as the bottom surface of the rest of the cage (2A) but the top surface of the brace (27) is located lower than the top surface of the rest of the cage (2A), as may be seen particularly in FIG. 10E. In this implementation example, the bottom surface of the brace (27) is equipped with notches (22) adding to the notches present on the rest of the cage in order to oppose the movement of the latter. In a variant, this brace may not include notches. In a variant, this type of cage may also be used in an inverse configuration in relation to this example. Thus, in this variant, the brace (27) will have a top surface at the same level as the top surface of the rest of the cage and a bottom surface located higher than the rest of the cage. All of these possible variants of the brace may naturally be combined with the other variants concerning the other characteristics of the cage.

In some embodiments of this present invention, the wall (25) of the cage (2A, 2B) includes at least one slot (20) having a width that allows the passage of this anchoring device (1) despite its curvature. This slot (20) may have a width (the height of the aperture described by the slot) substantially larger than the height of the anchoring device (1), to increase the ease of such passage. This slot (20) traverses the cage (2A, 2B) between a peripheral surface of the wall (25) and a top or bottom surface of the cage (2A, 2B), with an orientation that is designed for the radius of curvature of the anchoring device (1), so as to orientate the latter in the direction of the vertebral plate of one of the vertebrae between which the cage (2A, 2B) is implanted.

Some embodiments of this present invention provide an intervertebral disc prosthesis (2C). The prosthesis (2C) includes at least one first plate (51) and one second plate (52) that articulate along a curved surface. In one method of implementation, particularly visible in FIGS. 11A and 11B, the prosthesis (2C) includes only two plates (51, 52), each of which has a curved surface. These curved surfaces of the two plates (51, 52) are complementary and fit together to allow an articulation of plates (51, 52) by rotation about an axis that is more-or-less perpendicular to the plane of the plates and/or by sloping the plates in relation to each other. In another method of implementation that is particularly visible in FIGS. 11C and 11D, the prosthesis (2C) includes two plates (51, 52) and a central core (53), which is mobile in relation to at least one of the plates (51, 52). In one method of implementation, this core (53) includes a surface that is substantially plane, fitting onto a surface that is substantially plane of one of the plates (51, 52) and a curved surface fitting onto a complementary curved surface of the other plate (52, 51). The curved surface allows an articulation as described previously (inclination and/or rotation) and the plane surface allows a linear movement of the core in relation to the plate that includes the plane surface and/or a rotation of the core in relation to this plate, about an axis that is more-or-less perpendicular to the plane of the plates. In addition, according to the methods of implementation employed, the core (53) may include complementary mating resources (530) on at least one of the plates (51, 52) so as to limit the movement of the core (53) in rotation and/or in linear movement in relation to this plate. In some embodiments of the present invention, at least one of the plates (51, 52) of the prosthesis (2C) includes at least one slot (20) having a width that that allows the passage of this anchoring device (1) despite its curvature. This slot (20) may have a width (the height of the aperture described by the slot) substantially larger than the height of the anchoring device (1). Similar to some embodiments having an intersomatic cage (2A, 2B) discussed above, the intervertebral prosthesis (2C) may have one or more slots (20) that traverse the plate (51, 52) and orient the anchoring device (1) in the direction of the vertebral plate of one of the vertebrae between which the prosthesis (2C) is implanted. In some embodiments, the dimensions and orientation of the slot(s) (20) may be adapted, respectively, to the dimensions and to the radius of curvature of the anchoring device (1).

In a preferred method of implementation of the invention, the width of the slot (20) will be slightly greater than the thickness of the anchoring device (1), sufficiently to allow the passage of the latter within the slot, but by sufficiently little to enhance retention of the cage (2A, 2B) or of the prosthesis (2C) by the anchoring device (1), without excessive play of the latter within the slot (20). In various embodiments, the curvature of the device (1) along the abutment end may be configured to interfere with the slot (20) sufficiently to enhance the retention of the cage (2A, 2B) or of the prosthesis (2C) by the anchoring device (1). In certain methods of implementation of the invention, the length of the slot (20) may be substantially to the same as the width of the device (1) so that the latter has little or no play once inserted into the slot (20). The length of the anchoring device (1) may be designed for the depth of the slot (20) to be traversed and to the depth to which it must penetrate to the vertebral plates.

Thus, the anchoring device (1), by means of its radius of curvature and the orientation of the slot (20) in which it is inserted, may be implanted on an approach axis that is substantially along the plane of the intervertebral space, meaning the plane along which the cage (2A, 2B) or the prosthesis (2C) is implanted, which facilitates the approach of all of the elements of the intervertebral prosthesis or cage and the anchoring device to the edges of the intervertebral space. In one method of implementation, the arc described by the body (10) has dimensions, and a radius of curvature that are designed in such a manner that the anchoring device (1) is implantable in a vertebral plate on an approach axis forming an angle with the vertical axis of the vertebral column of between 40° and 140°, and preferably an angle of approximately 90°. This angle may vary for a given anchoring device (1) depending on the dimensions at the edges of the vertebrae, and may also vary from one anchoring device (1) to another depending on the radius of curvature of the device (1) used and the angle (AC) formed between its abutment and penetration ends.

In one method of implementation of the invention, the curved and elongated body (10) includes at least one curved plate, as may be seen particularly in FIG. 1 (A to D). This plate may be substantially rectangular as shown in the Figures, but may naturally have various shapes without moving outside the spirit of the invention. Likewise, in other implementation variants, the body (10) may include a curved rod, with the slot (20) then having a shape to suit the section of this rod, but the invention naturally allows other methods of implementation, in particular regarding the shape of the body (10). In other implementation variants (not shown), the body (10) of this anchoring device (1) may include two plates (or two rods), generally parallel to each other, and connected together at the abutment end by an inward-curving part that fits onto a rod present at the centre of the slot (20) in the cage, for example as described in U.S. patent application Ser. No. 10/483,563, or U.S. patent application Ser. No. 11/109,276, each of which is incorporated herein by reference.

The penetration end of the anchoring device (1) penetrates into the vertebral plate of one of the vertebrae between which the cage (or the prosthesis) is to be implanted. In one method of implementation of the invention, the penetration end includes a chamfer (13) or a bevel to facilitate the penetration of the device (1) into the vertebra, as may be seen particularly in FIGS. 1C and 1D. In an implementation variant, this penetration end may also include an indentation (15), in the form of a V-shaped notch, for example, as shown in FIG. 1B, to facilitate the penetration of the penetration end into the vertebral plates. The abutment end is butted up against a surface of the cage or of the prosthesis that the device secures, so as to hold the latter against the vertebral plate, preferably firmly and tightly.

In different implementation variants of the anchoring device (1), the abutment end of the body (10) includes at least one stop element (11) that mates with at least one surface of the cage (2A, 2B) or of the prosthesis (2C) that the device (1) secures. In a complementary manner, in different implementation variants of the cage (2A, 2B) or of the prosthesis (2C), at the level of the peripheral surface of the wall (25), the slot (20) includes at least one stop element surface (21) that mates with at least one stop element (11) of the anchoring device (1). In one method of implementation, particularly visible in FIGS. 1A and 1D, the stop element (11) includes a projecting lug on at least one face of the anchoring device (1). In the example shown, this stop element consists simply of a lug orientated toward the interior of the circle of which the arc described by the body (10) forms part, but the lug may adopt different orientations. The cage (2A, 2B) or the prosthesis (2C) may then simply include, below the slot (20), a contact surface for this stop element (11). The stop element surface (21) of the cage (2A, 2B) or of the prosthesis (2C) may then include a peripheral surface of the wall (25) or of the plate (51, 52) to accommodate this projecting lug on at least one face of the body (10) of the anchoring device (1). In another method of implementation that is particularly visible in FIGS. 1B and 1C, the stop element (11) includes two projecting lugs on the sides of the body (10). These two lugs may consist of two latches click-fitted in the slot. In this method of implementation, the stop element surface (21) of the cage (2A, 2B) or of the prosthesis (2C) may include, for example, two recesses (21) located on either side of the slot (20) to accommodate two projecting lugs on the sides of the body (10) of the anchoring device (1). These two recesses may, for example, have a shape and dimensions to suit the click-fitting of the lugs of the anchoring device (1). In addition, as may be seen particularly in FIGS. 11A and 11C, the periphery of the plates form an opening at the level of the slot for the insertion of the device and the edge located between this opening and the periphery of the plate forms a sort of rod onto which the stop element (11) of the anchoring device (1) may fit. Thus, the stop element (11) of the device (1) may consist of a curved portion that click-fits on the edge of the plate. Thus, the device (1) may be removable (in many methods of implementation) and may be implanted in the vertebrae and fitted onto the plates of the prosthesis after the implantation of the latter between the vertebrae. This method of implementation allows adjustment, where appropriate, of the position of the prosthesis between the vertebrae before definitive securing.

In certain methods of implementation of the invention, the body (10) includes, on at least one of its sides, one or more flexible lugs (14) orientated toward the abutment end and forming a stop element to oppose the withdrawal of the anchoring device (1). As may be seen particularly in FIGS. 1A and 1B, this flexible lug (14) may be present on the two lateral sides of the body (10), but it may naturally be located on a single face of the body, such as the top or bottom face, for example. This (or these) flexible lug(s) (14) are used to secure the anchoring device (1) in relation to the cage (2A, 2B) or the prosthesis (2C), by means of their orientation in the direction of the abutment end. When the device (1) is inserted into the slot (20), the lugs (14) fold up because of their flexibility, thus allowing the passage of the device (1) in the slot even if the width of the body (10) is substantially the same as the length of the slot (20), as mentioned previously, as a result, for example, of the recesses in the body (10) provided for the folding over of these lugs (14) or by means of the shape of the body (10) in relation to the slot (20). The position of these flexible lugs (14) on the body (10) may also be arranged so that they emerge at the other side of the slot (20), along the bottom or top surface of the wall (25) of the cage (2A, 2B) or at the bottom or top surface of the plate (51, 52) of the prosthesis (2C). In this method of implementation, at the bottom or top surface of the wall (25), the slot (20) may include at least one stop element surface that mates with these lugs. On the other hand, the position of these flexible lugs (14) on the body (10) may also be arranged so that they do not emerge from the slot (20), which may then have at least one recess allowing the lugs (14) to unfold and oppose the withdrawal of the anchoring device (1).

In certain methods of implementation of the invention, the body (10) is equipped with notches (12) that are orientated so as to oppose the withdrawal of the device (1) after it has been implanted in a vertebra. As may be seen particularly in FIGS. 1A and 1B, the number, the dimension and the shape of these notches (12) may vary according to the implementation variants, without moving outside the spirit of the invention.

Depending on the methods of implementation, the cage (2A, 2B) may have different shapes. The description that follows gives some non-limiting implementation variants with reference to the appended Figures, but the cage (2A, 2B) and the prosthesis (2C) may of course have other shapes without moving outside the spirit of the invention. For example, the cage (2A) represented in FIG. 2 (A to E) is substantially annular, with a periphery that is substantially circular, except at the location of the slot (20) for insertion of the anchoring device (1), at which point it will be held by an implantation instrument (3, 4). The shape of the cage (2A, 2B) or of the prosthesis (2C) may vary, of course, and the shape of the end of the said instrument (3, 4) in contact with the cage (2A, 2B) or the prosthesis (2C) may vary as a consequence, according to some of the methods of implementation. The cage (2A, 2B) and the prosthesis (2C) may, for example, have different shapes, which preferably have a slot (20) designed for the insertion of the device (1), and attachment resources (24) adapted to mate with one end of an implantation instrument. Depending on the methods of implementation, these attachment resources (24) may be associated with a particular shape of the cage (2A, 2B) or of the prosthesis (2C) close to these attachment resources (24) to allow a good fit with the instrument or may even have such particular shapes fitting onto complementary shapes of the instrument. For example, the instrument may include a contact surface fitting closely onto the shape of the prosthesis (2C) close to the recess (24) and/or of the slot (20). Likewise, as mentioned previously, the cage (2A, 2B) may include a cavity (23) at its centre or not, to the extent that it is common to implant several intersomatic cages (2A, 2B) in a given intervertebral space (on condition that the dimensions allow it). The cages thus implanted are generally used to enclose bony tissue (a graft) which will grow within the intervertebral space and allow a fusion (arthrodesis) of the two vertebrae between which it is implanted. It is also common to use a substitute instead of an osseous graft. In any event, the aim of the cage (2A, 2B) is to restore or maintain a space between the vertebrae. Before the growth of the graft and the fusion of the vertebrae, the cage (2A, 2B) should remain correctly in position in the disc space, and various embodiments of this present invention facilitate its immobilisation.

Before the implantation of the anchoring device (1) used to maintain the cage (2A, 2B) in position, there may be a risk that the cage (2A, 2B) will move within the disc space. In certain methods of implementation, at least one of the top and bottom surfaces of the wall (25) will include notches (22) that prevent movement of the cage (2A, 2B) between the vertebrae between which it is implanted. Likewise, at least one of the plates (51, 52) of the prosthesis (2C) may be fitted, on its surface in contact with the vertebrae, with stabilisation resources, such as notches or fins or any type of structure that may be used to prevent its movement between the vertebrae, so as to enhance stability of the prosthesis before it is secured by the anchoring device (1). Thus, at least one of the top and bottom surfaces of at least one of the plates (51, 52) may include notches (22) that prevent movement of the prosthesis (2C) between the vertebrae between which it is implanted. According to various methods of implementation, these notches (22) or other stabilisation resources may have different orientations, so as to prevent movement of the cage (2A, 2B) or of the prosthesis (2C) in one or more directions. For example, the notches (22) may be substantially parallel to each other and all orientated perpendicularly to the axis of insertion of the cage (2A, 2B) or of the prosthesis (2C), but on the other hand the notches (22) may have different orientations on different portions of the cage (2A, 2B) or of the prosthesis (2C), so as to prevent movement in any direction.

In some situations, in particular depending on the vertebrae between which the cage (2A, 2B) or the prosthesis (2C) must be implanted, it is desirable that the cage (2A, 2B) or the prosthesis (2C) allow the imposition of a lordosis or kyphosis in addition to maintaining the space between the vertebrae. Certain methods of implementation therefore provide that the mean planes passing along the top and bottom surfaces of the cage (2A, 2B) form an angle (A1) that imposes a lordosis on the vertebrae between which the cage (2A, 2B) is implanted. For example, FIG. 2B represents a view from above of a cage (2A) according to one method of implementation of the invention. This cage is implanted substantially along axis 2C-2C representing, in FIG. 2B, the plane of the view in section of FIG. 2C. FIG. 2C shows that the mean planes (28) of the bottom and top surfaces of the cage (2A) form an angle (A1) which imposes a lordosis along axis 2C-2C. On the other hand, in certain methods of implementation, the mean planes passing along the top and bottom surfaces of the cage (2A, 2B) may be substantially parallel to each other. Likewise, the prostheses (2C) may include plates whose top and bottom surfaces are substantially parallel to each other but may include plates whose top and bottom surfaces form an angle that may, for example, impose a lordosis or a kyphosis. Thus, in certain methods of implementation, the mean plane passing along the top and bottom surface of at least one of the plates (51, 52) of the prosthesis (2C) forms an angle (A1) that imposes a lordosis on the vertebrae between which the prosthesis (2C) is implanted, for example as described in U.S. patent application Ser. No. 11/109,276 or U.S. patent application Ser. No. 11/098,266, each of which is incorporated herein by reference. In other methods of implementation, the mean planes passing along the top and bottom surfaces of at least one of the plates (51, 52) of the prosthesis (2C) are substantially parallel to each other. In the case of prostheses that include a mobile central core (53) whose movement is limited by mating resources (530), the lordosis may be obtained by a core (53) that at rest is moved off-centre by means of these mating resources (530) and/or the mating resources (531) of the plate.

In addition, in certain methods of implementation, the peripheral wall (25) of the cage (2A, 2B) may include at least one chamfer (250) on at least one peripheral portion of at least one of its top and bottom surfaces, so as to facilitate the insertion of the cage (2A, 2B) between the vertebrae. As may be seen particularly in FIG. 2B, this chamfer (250) of the cage (2A) may be located substantially in the axis (2C-2C, FIG. 2B) of implantation of the prosthesis. In addition, as may be seen particularly in FIG. 2D, this chamfer (250) may be present on the two bottom and top surfaces of the cage (2A). This chamfer (250) or bevelled profile facilitates the implantation of the cage (2A, 2B) by according it a height that is somewhat less on its attacking edge (that is inserted first) than on the rest of the cage. Likewise, the plates of the prosthesis (2C) may include, on the periphery of their surface in contact with the vertebrae, at least one chamfer to facilitate the insertion of the prosthesis (2C) in the disc space.

In certain methods of implementation, the peripheral wall (25) of the cage (2A, 2B) includes two superimposed slots (20) each of which is orientated toward one of the top and bottom surfaces, so as to allow anchoring of the anchoring device (1) in each of the vertebrae between which the cage (2A, 2B) is implanted. Likewise, each of the plates (51, 52) may include a slot (20), each of which may be orientated toward one of the top and bottom surfaces, so as to allow the securing of each of the plates (51, 52) by the anchoring of an anchoring device (1) in each of the vertebrae between which the prosthesis (2C) is implanted. In other methods of implementation, the cage (2A, 2B) may have only single slot (20). In some embodiments, only one plate (51, 52) of the prosthesis (2C) has a slot and the other plate has none.

In certain methods of implementation, the cage (2A, 2B) may be implantable on an axis located substantially along the plane of the intervertebral space but which is oblique in relation to the vertical axis of the vertebral column so as, for example, to allow the implantation between the vertebrae at the point at which blood vessels pass, preventing frontal access to the intervertebral space. In this case, the cage (2A) should be implanted on an axis of implantation that is oblique in relation to the antero-posterior axis of the vertebral column (the sagittal axis) meaning the axis in which a lordosis may have to be imposed. As shown in FIG. 3B, the axis of insertion of the anchoring device (1) is orientated along axis 3C-3C, representing the section plane of FIG. 3C and the cage (2A) is implanted on this axis, but because of the possible dimensions of the access to the intervertebral space, the antero-posterior axis of the vertebrae may be orientated along axis 3D-3D in relation to the cage, which may thus be implanted obliquely. As may be seen particularly in FIG. 3A, and by comparison with FIGS. 3C and 3D, cage (2A) may allow the imposition of a lordosis by means of an angle (A1, FIG. 3A) of inclination between its top and bottom surfaces, but the axis of inclination of the mean planes (28) passing along its top and bottom surfaces is orientated along axis 3D-3D and not along axis 3C-3C. The cage therefore imposes a larger lordosis along axis 3D-3D than along axis 3C-3C in order that it may be implanted along oblique axis 3C-3C in relation to axis 3D-3D corresponding to the antero-posterior axis of the vertebrae (the sagittal axis). Thus, a cage according to this particular method of implementation may be implanted obliquely and allow the imposition of a lordosis that is aligned correctly with respect to the vertebral column.

In other methods of implementation, the peripheral wall (25) may include at least two slots (20) located alongside each other, with each of these defining one possible axis of insertion of the anchoring device (1) in the cage (2A, 2B) and, indirectly, one possible axis of insertion of the cage (2A, 2B) between the vertebrae. For example, as may be seen particularly in FIGS. 4A and 4B, the cage (2A) includes 2 superimposed slots (20) each of which is orientated toward one of the top and bottom surfaces of the cage on a first axis (4C-4C, FIG. 4B) located alongside 2 superimposed slots (20) each of which is orientated toward one of the top and bottom surfaces of the cage on a second axis (4D-4D, FIG. 4B). In this implementation variant, the cage (2A) may be implanted along axis 4C-4C or along axis 4D-4D but the inclination of the mean planes passing along the top and bottom surfaces of the cage is orientated along axis 4C-4C, as may be seen by comparison with FIGS. 4C and 4D. This type of cage may therefore be implanted obliquely (along axis 4D-4D) or frontally (along axis 4C-4C). In a relatively similar manner, the plates (51, 52) of the prostheses represented in FIGS. 11A to 11D include several slots (20) each. In the examples shown, these slots are located on the edges of the plates, but either centred in relation to the antero-posterior axis of the prosthesis, or moved off-centre. These slots then define two possible axes of insertion of the osseous anchoring device (1), namely either on the antero-posterior axis, or on an oblique axis. In addition, the attachment resources (24) of the prosthesis (2C) are located close to each of these slots, so as to allow gripping of the prosthesis during the impacting of the device (1) in the vertebrae. Thus, these attachment resources (24) also define two possible axes of insertion of the prosthesis (2C) between the vertebrae by the instrument, namely either an antero-posterior axis, or an oblique axis. After appreciating this disclosure, those of skill in the art will appreciate that the invention allows many variants regarding the position and the shape of these attachment resources (24) and of the slots (20). It will be noted in passing that in FIGS. 11A and 11B, for example, the devices (1) of the two anchoring plates do not have the same orientation as each other, which may be explained by a different orientation of their slot (20). Naturally, these Figures are simply illustrative, and in no way limiting, since it is possible to envisage any type of combination of orientations and of shapes and of position slots (20) on the plates after appreciating this disclosure.

In other methods of implementation, the intersomatic cage may be of the transforaminal type, meaning implanted through the foramen. This type of cage, which is described, for example, in patent application FR 06 01315 and U.S. patent application Ser. No. 11,378,165 each submitted by the present applicant and which are incorporated herein by reference, is particularly advantageous because it is relatively small and may therefore be implanted by the transforaminal route. In various methods of implementation of this present invention, the cage (2B) is in the shape of a circular arc, as may be seen particularly in FIGS. 8A and 8B, and includes at least one slot (20) of shape, dimension and orientation to suit the insertion of a curved anchoring device (1) according to the different methods of implementation of this present invention. As may be seen particularly in FIG. 8A, the wall (25) of the cage may form a cavity (23), internal or not, as for the cages (2A) described previously. In addition, as may be seen particularly in FIG. 8A, the wall (25) may include at least one lateral opening (26) that allows the growth of the graft through the cage (2B). Although these lateral openings have not been represented in the other Figures with reference to the cages (2A) described previously, after appreciating this disclosure those of skill in the art will recognize that these too may also include such openings (26), where appropriate. This type of cage (2B) has an arcuate peripheral wall (25), for example describing a circular arc. The radius of curvature of the cage (2B) and the dimensions of the latter may naturally vary according to the methods of implementation, and according to the vertebrae between which they must be implanted. The wall (25) in an arc of the cage (2B) is extended, at one of its ends, by a return part extending in the direction of the inside of the curve described by the wall (25). In certain methods of implementation, as may be seen particularly in FIGS. 8B and 8C, this return part may include a chamfer (250) to facilitate its implantation between the vertebrae. Like for the first implementation variants of intersomatic cages (2A), these transforaminal implementation variants of the intersomatic cages (2B) may be equipped with notches (22) on at least one part of at least one of their bottom or top surfaces. Whatever the type of cage (2A, 2B), these notches (22) may have different orientations and present a pattern that is linear or circular, or any other type of pattern, and the lines or circles described by the notches may either cross each other or not. For example, as may be seen particularly in FIGS. 8B and 8C, the notches (22) may describe a pattern of chevrons or of circular arcs. The different methods of implementation of the anchoring device (1) described previously with reference to the previous methods of implementation of intersomatic cages (2A) may naturally be adapted to these transforaminal implementation variants of the cage (2B) and vice versa. Likewise, the different methods of implementation concerning the slots (20) may be adapted to this type of transforaminal cage (2B) and vice versa, on condition that the dimensions allow it or are adapted to allow it.

In some methods of implementation, the intersomatic cages (2A, 2B) or the intervertebral prostheses (2C) will be implanted by means of a special instrument (3, 4) that is used to implant them between the vertebrae and that may be used to implant the anchoring devices (1) in the vertebral plates. In these methods of implementation, the peripheral wall (25) of the cages (2A, 2B) or at least one of the plates (51, 52) may include at least one attachment resource (24) that mates with a gripper end of an instrument (3, 4) for implantation of the cage (2A, 2B) or of the prosthesis (2C). As mentioned previously, this attachment resource (24) may include at least one recess (24) that receives the end of a gripping resource (321). As may be seen particularly in FIG. 3A, the cage may include two recesses (24) each located on one side of the slot, to facilitate gripping of the cage, but the recesses of course may be located in other places, preferably for these recesses to facilitate the gripping of the cage (2A, 2B) or of the prosthesis (2C) by a complementary instrument. As may be seen particularly in FIG. 4A, a slot (20) in the cage may be associated with a single recess (24) but it is possible to provide several recesses (24) around the slots (20), even when the cage (2A, 2B) includes several slots (20) as in this implementation example. These different variants concerning the number and the position of the attachment resources (24) and of the slot (20) described here naturally apply equally well to the cages (2A, 2B) and to the prostheses (2C).

Various embodiments of the present invention therefore also concern an instrument (3, 4) for the implantation of an intersomatic cage (2A, 2B) or of an intervertebral disc prosthesis (2C) between the vertebrae and for the implantation of an anchoring device (1) in at least one of these vertebrae. The instrument may include an impactor (4) that includes a head (40) whose shape and dimensions are designed to push on the anchoring device (1). The instrument may also include a guide (3) of elongated shape on a longitudinal axis extending between a first end, called the gripping end of the cage or of the prosthesis, and a second end, called the push end. The gripping end includes at least one gripping resource (321) that mates with at least one means (24) of attaching the cage (2A, 2B) or the prosthesis (2C). Depending on the methods of implementation, the push end may include a handle (33) that is used to push the guide holding the cage (2A, 2B) or the prosthesis (2C) in order to insert the latter into the intervertebral space. This handle may also consist of a stop element on which the surgeon may tap, by means of a tool of known type for example, in order to introduce the cage or the prosthesis between the vertebrae. After appreciating this disclosure those of skill in the art will recognize that the different elements of the instrument (3, 4) described here may be present whatever the method of implementation of the cage (2A, 2B) or of the prosthesis (2C), unless it is expressly specified in this present description that a particular element concerns only one type of cage described previously or a single type of prosthesis.

The guide (3) of the instrument may include a head (30) whose shape and dimensions are designed to at least partially accommodate the head (40) of the impactor, and includes at least one guidance surface (31) having a radius of curvature that is substantially the same as the radius of curvature of the anchoring device (1). This curved surface (31) may guide this anchoring device (1) through the slot (20) of an intersomatic cage (2A, 2B) or of an intervertebral prosthesis (2C), for the impacting of the anchoring device (1) into a vertebral plate of one of the vertebrae between which the cage (2A, 2B) or the prosthesis (2C) is implanted.

The guide (3) may include an elongated body (32) that allows an approach to the intervertebral space without needing a lot of space. The impactor (4) also may include an elongated body (42), which slides in relation to the body (32) of the guide (3). In certain methods of implementation, the impactor (4) includes a handle (41) which is used to cause the body (42) of the impactor to slide in relation to the guide (3). This handle may also play the role of a stop element on which the surgeon may tap, by means of a tool of known type for example, in order to cause the anchoring device (1) to penetrate into a vertebral plate. In addition, in certain methods of implementation, the impactor (4) may include at least one stop element (43) which limits the penetration of the head (40) of the impactor (4) within the head (30) of the guide (3). In certain variants, the position of this stop element may be adjustable along the body (42) of the impactor (4), for use in adjusting the penetration of the impactor to the size of the head (30) of the guide (3) and to the size of the anchoring device (1) employed. For example, as mentioned previously, the anchoring device (1) may have a length that is variable to suit the circumstances and the head (30) of the guide, and in particular the curved guidance surface (31) will also be of a size designed for this length of the anchoring device (1).

Depending on the methods of implementation, the body (32) of the guide (3) may have two rods or tubes (32), as shown in FIG. 6B, but the guide (3) may have a single rod or a single tube, even if the guide includes several gripping resources (321), preferably allowing these resources (321) to secure the cage or the prosthesis. As may be seen particularly in FIG. 6D, in certain methods of implementation, the gripping resources (321) may consist of rods (321) fitted freely within the tubes (32) constituting the body of the guide (3). In some embodiments, these rods may not be within the body (32). In different methods of implementation, the gripping resource (321) may comprise one end of a rod which slides in a body (32) of the guide (3) when it is operated by a handle (33) so as to enter and leave the recess (24) of the cage (2A). In these implementation variants, these gripping resources (321) may include threads at their ends so as to be screwed within the recess (24) of the cage (2A, 2B), which may include a tapping. In certain implementation variants, the rod (321) may therefore include a threaded end fitting into a tapping in the recess (24) in order to secure the cage (2A) when the rod is operated by the handle (33). In other variants, the rod may have dimensions that are adjusted to penetrate exactly into the recess, and allow the retention of the cage by this exact adjustment. These different variants of the rod (321) and of the recess (24) naturally may also be applied to prostheses (2C). For example, the prostheses represented in FIGS. 11A to 11D include plates (51, 52) that include recesses (24) to accommodate these gripping resources (321). In the examples of implementation represented, the gripping resources (321) may be located close to the top and bottom surfaces of the head (30) of the guide (3) so that these resources (321) allow the correct gripping of two plates (51, 52) of the prosthesis (2C). Various embodiments of the invention allow other methods of implementation of the attachment resources (24) and of the gripping resources (321), for example as mentioned previously. In addition, in the implementation example of the prosthesis (2C) of FIGS. 11C and 11D that includes two plates (51, 52) and a core (53), the attachment resources (24) may also include attachment resources located on the core, so that the latter is also retained by the instrument. For example, the surface of the head (30) of the guide facing the prosthesis (2C) may have a shape that is complementary to the two plates and to the core assembly, so as to hug the shape of the prosthesis and keep the elements of the prosthesis stable.

In the methods of implementation represented in FIG. 6 (A to E) and 7 (A to D), the body (32) includes a guidance plate (34) that is used to guide the impactor (4). In these methods of implementation, the plate (34) includes a groove that guides the impactor on the axis of the body (32) of the guide. In other possible methods of implementation, as represented in FIG. 9A, for example, the body (42) of the impactor (4) may be mounted to slide within the body (32) of the guide, but the invention naturally allows other implementation variants, preferably allowing the impactor (4) to be guided in relation to the head (30) and to slide in relation to the guide (3).

As may be seen particularly in FIG. 5A, the head (30) of the guide (3) includes a cavity (300) whose shape and dimensions are designed to receive the anchoring device (1) and, at least partially, the head (40) of the impactor (4). Various embodiments of the invention naturally allow different methods of implementation of the head (30) and the examples given here are only by way of illustration. The head (30) of the guide may include at least one passage (320) through which the gripping resource (321) of the cage or of the prosthesis will be inserted in order to hold the cage or the prosthesis at the end of the guide (3). In the method of implementation represented in FIGS. 5A and 5B, this head includes two identical passages on either side of the cavity (300), since this method of implementation of the head (30) is designed to be mounted on a guide (3) that has two gripping resources (321). After appreciating this disclosure those of skill in the art will recognize that the invention will allow the use of only one gripping resource (321) or, on the other hand, an increase in their number by reducing their size and by distributing them differently around the cavity, for example, with the provision of complementary recesses on the cages to be implanted. In addition, a given instrument (3, 4) may serve for the implantation of different types of cages (2A, 2B) or prostheses (2C), preferably with the gripping resources (321) of the guide (3) and the attachment resources (24) of the cages (2A, 2B) or of the prostheses (2C) being designed to be complementary. For example, the instrument that includes a head (30) as represented in FIG. 5E, may serve for the implantation of the cage (2A) of FIG. 4A, even though one of the gripping resources (321) of the guide (3) will not be used in this case. Inside the cavity (300) of the head (30) of the guide (3) there may be at least one curved guidance surface (31) of the anchoring device (1). In the methods of implementation illustrated here by way of example, this guidance surface (31) may include at least two curved grooves (31) each located on either side of this cavity (300) to guide the anchoring device (1) on both sides of its body (10). The head (40) of the impactor (4) is then designed to penetrate into the cavity (300) from one end to the other of these grooves (31), so as to push the anchoring device (1) from one end to the other of these grooves (31). In the method of implementation represented in FIG. 5 (A to E), the cavity (300) of the head (30) may receive two guidance elements (310) (particularly visible in FIGS. 5C and 5D), with each including the guidance grooves (31) and each located on one side of the cavity (300), as may be seen particularly in FIG. 5E. In this implementation example, the guidance elements (310) are assembled with the head (30) by inserting it into the cavity (300) which may include securing resources that are used to immobilise these guidance elements (310). In other examples of implementation such as, for example, the head (30) of the guide (3) represented in FIGS. 8C and 9 (A to C), the head (30) will be made with of the guidance grooves (31) directly on the inside of the cavity (300). In this case, the head may be made in two assembled parts in order to facilitate the machining of the curved grooves (31).

In certain methods of implementation, as shown in FIGS. 3A, 4A and 5A, the recess (24) of the cages (2A) may be created close to the slot (20), and the passage (320) for the gripping resources (321) may be close to the cavity (300) so as to allow correct gripping of the cage close to the site at which the anchoring device (1) is likely to apply pressure on the cage under the action of the impactor (4). The resource (24) for attachment of the prostheses (2C) may naturally be made in the same way.

As may be seen particularly in FIGS. 6C and 9B, the gripping resource (321) may protrude beyond the head (30) of the guide (3) at the position of the gripping end. As may be seen particularly in FIGS. 7A and 7B or in FIGS. 9A and 9C, the guide may allow the gripping of the cage (2A, 2B) with one end of the guidance surface (31) ending in the slot (20) in the cage (2A, 2B) thus held, and the other end of the guidance surface (31) remaining accessible for the insertion of the anchoring device (1). In these methods of implementation, the anchoring device (1) may be inserted in the head (30) after the cage (2A, 2B) has been mounted on the gripping resources (321), but other methods of implementation, which may be less advantageous but less costly to implement, may require insertion of the anchoring device (1) prior to the mounting of the cage (2A, 2B). These variants also may apply to the prostheses (2C) which may be designed in the same way and may therefore be implanted with the same instrument as that described for these cages (2A, 2B).

In the case of the transforaminal cages (2B), the instrument may allow the cage to be held over virtually the whole of its length, which may facilitate the insertion of the cage (2B) into the intervertebral space and protect it from damage. In this method of implementation of the cage (2B), the gripping resource (321) may be the end of a curved rod, such as a spatula, which may have a radius of curvature substantially identical to a radius of curvature of the cage (2B) having a peripheral wall (25) describing an arc. In this method of implementation, the recess (24) may be located on the return part extending one end of the circular arc described by the wall (25) of the cage (2B) in the direction of the centre of the circle of which the circular arc described by the wall (25) forms part. The spatula may hug the shape of the cage (2B) between this return part and the other end of the circular arc described by the wall (25) of the cage (2B). At this other end of the wall (25), the cage (2B) advantageously may include a second gripping resource to hold the cage (2B). In certain methods of implementation of the transforaminal cage, this second gripping resource may be located at the base of the spatula, but on the side opposite to that carrying the spatula. This second gripping resource may include a second recess (241) to accommodate a latch (341) mounted on a rod (340) of the guide (3). As explained previously for the body (32) of the guide and the body (42) of the impactor or the gripping resources (321), this rod (340) may be mounted freely within the body (32) of the guide or on the outside, preferably so that it is guided in relation to the head (30). This rod (340) may be operated by a handle and may pivot between at least one position at which the latch (341) engages the second recess (241), and a position at which the latch (341) exits from the second recess (241) and thus frees the cage (2B).

In certain methods of implementation of the implantation instrument (3, 4), particularly suitable for the transforaminal cages whose insertion must be accomplished along an arc or an oblique axis in relation to the antero-posterior axis of the vertebrae, the head (30) of the guide (3) may be curved or bent substantially along the radius of curvature of the arc described by the cage (2B). Thus, the bent instrument allows easier passage through the foramens, although it may be used in another context. In this bent method of implementation of the head (30) of the guide (3), the head (40) of the impactor (4) may have a shape that is more or less curved or bent so that it has a radius of curvature compatible with its passage in the head (30) of the guide (3). In addition, in a particularly advantageous variant, this head (40) of the impactor (4) may be mounted on an axis (425) of rotation mounted on the body (42) of the impactor. This axis (425) allows the head (40) of the impactor to pivot in order to pass the curvature or the bend in the head (30) of the guide (3), as may be seen particularly in FIG. 9B. In another implementation variant, the impactor (4) may be straight and designed to be inserted in the head (30) on an oblique axis, substantially parallel to axis 9C-9C of FIG. 9B for example, with the head (30) then having an opening of sufficient size to allow the introduction of the head (40) of the impactor (4).

After appreciating this disclosure those of skill in the art will recognize that this present invention allows methods of implementation in many other specific forms without moving outside the scope of the invention. As a consequence, these present methods of implementation must be considered to be illustrations only, but may be modified within the area defined by the scope of the attached claims, and the invention should not be limited to the details given above.

The invention claimed is:

1. An apparatus for implantation of a spinal implant comprising:
    an intersomatic cage configured for implantation in an intervertebral space between adjacent vertebrae of a spinal column, the intersomatic cage comprising a peripheral wall and a receptacle extending from a surface of the peripheral wall and traversing at least a portion of the peripheral wall, the receptacle configured for passage of an anchoring device having a body with a curved shape along a longitudinal axis that describes an arc and for orientation of the anchoring device during implantation of the anchoring device in a vertebra;
    an anchoring device for anchoring the intersomatic cage between the adjacent vertebrae, the anchoring device comprising a body having an elongated shape along a longitudinal axis extending between a penetration end and an abutment end, the body having a curved shape along the longitudinal axis that describes an arc, and the body having dimensions and a radius of curvature configured for implantation of the anchoring device in one of the vertebrae by presentation of the longitudinal axis along an approach axis that is substantially along a plane of the intervertebral space and by insertion of the anchoring device through the receptacle in the intersomatic cage with the anchoring device traversing at least a portion of the intersomatic cage; and
    an instrument comprising
        an impactor having an impactor head configured to push the anchoring device; and
        an elongated guide having a gripping end and a push end, the guide comprising
            a gripping device disposed at the gripping end and configured to grip the intersomatic cage, and
            a guide head configured to at least partially accommodate the impactor head, the guide head comprising at least one guidance surface having a radius of curvature substantially the same as the radius of curvature of the anchoring device and configured to guide the anchoring device through a receptacle of the intersomatic cage.

2. An apparatus for implantation of a spinal implant according to claim 1, in which the dimensions and radius of curvature of the body of the anchoring device are configured for implantation of the device by presentation of the longitudinal axis along an approach axis forming an angle of approximately 90° with the vertical axis of the spinal column.

3. An apparatus for implantation of a spinal implant according to claim 1 in which the body of the anchoring device includes at least one curved plate.

4. An apparatus for implantation of a spinal implant according to claim 1 in which the penetration end of the anchoring device comprises a chamfer to facilitate the penetration of the device into the vertebrae.

5. An apparatus for implantation of a spinal implant according to claim 1 in which the body of the anchoring device comprises notches orientated to oppose withdrawal of the device when implanted in a vertebra.

6. An apparatus for implantation of a spinal implant according to claim 1 in which the abutment end of the anchoring device comprises a stop element configured to mate with a surface of the implant.

7. An apparatus for implantation of a spinal implant according to claim 6 in which the stop element of the anchoring device comprises a projecting lug on a side of the body.

8. An apparatus for implantation of a spinal implant according to claim 1 in which the body of the anchoring device comprises a flexible lug disposed along a side of the body, the flexible lug orientated toward the abutment end and forming a stop.

9. An apparatus for implantation of a spinal implant according to claim 1 in which the receptacle of the intersomatic cage comprises a slot having a first stop configured to mate with a second stop of the anchoring device.

10. An apparatus for implantation of a spinal implant according to claim 9 in which the first stop of the intersomatic cage comprises a recess configured to accommodate a projecting lug of the anchoring device.

11. An apparatus for implantation of a spinal implant according to claim 9 in which the first stop of the intersomatic cage comprises a portion of the surface of the peripheral wall configured to accommodate a projecting lug of the anchoring device.

12. An apparatus for implantation of a spinal implant according to claim 1 in which the receptacle of the intersomatic cage comprises a stop configured to mate with a flexible lug of the anchoring device to oppose withdrawal of the anchoring device from the receptacle.

13. An apparatus for implantation of a spinal implant according to claim 1 in which the peripheral wall of the intersomatic cage comprises an attachment device configured to mate with a gripper of an implantation instrument.

14. An apparatus for implantation of a spinal implant according to claim 1 in which the intersomatic cage comprises top and bottom surfaces, at least one of which having notches configured to prevent movement of the intersomatic cage when the intersomatic cage is implanted.

15. An apparatus for implantation of a spinal implant according to claim 1 in which the intersomatic cage comprises top and bottom surfaces each having a mean plane passing therethrough, and the mean planes are configured to form an angle configured imposes for imposing a lordosis on the adjacent vertebrae.

16. An apparatus for implantation of a spinal implant according to claim 1 in which the intersomatic cage comprises plural receptacles, at least one of which plural receptacles is configured for orientation of the anchoring device during implantation of the anchoring device in a first one of the adjacent vertebrae and at least one of which plural receptacles is configured for orientation of the anchoring device during implantation of the anchoring device in a second one of the adjacent vertebrae.

17. An apparatus for implantation of a spinal implant according to claim 1 in which the intersomatic cage comprises top and bottom surfaces and in which the peripheral wall comprises at least one chamfer on at least one of the top and bottom surfaces.

18. The apparatus according to claim 1 in which the guide head further comprises a cavity configured to receive the anchoring device and, at least partially, the impactor head, and the guidance surface includes at least two curved grooves disposed along adjacent sides of the cavity.

19. The apparatus according to claim 1 in which the impactor comprises a rod slideable in relation to the guide and operable by a handle.

20. The apparatus according to claim 19 in which the impactor comprises a stop element configurable to limit travel of the impactor head with respect to the guide head.

21. The apparatus according to claim 19 in which the rod comprises a threaded end configured to engage a tapping in the intersomatic cage.

22. The apparatus according to claim 1 in which the guidance surface is configured for a first end of the guidance surface to align with the receptacle of the intersomatic cage and for a second end of the guidance surface to be accessible for the insertion of the anchoring device.

23. The apparatus according to claim 1 further comprising a rod slideable in a body of the guide and operable by a handle, and in which the gripping device comprises an end of the rod that is configured to engage a recess in the intersomatic cage.

24. An apparatus for implantation of a spinal implant comprising:
an intersomatic cage configured for implantation in an intervertebral space between adjacent vertebrae of a spinal column, the intersomatic cage comprising a peripheral wall and a receptacle extending from a surface of the peripheral wall and traversing at least a portion of the peripheral wall, the receptacle configured for passage of an anchoring device having a body with a curved shape along a longitudinal axis that describes an arc and for orientation of the anchoring device during implantation of the anchoring device in a vertebra;
an anchoring device for anchoring the intersomatic cage between the adjacent vertebrae, the anchoring device comprising a body having an elongated shape along a longitudinal axis extending between a penetration end and an abutment end, the body having a curved shape along the longitudinal axis that describes an arc, and the body having dimensions and a radius of curvature configured for implantation of the anchoring device in one of the vertebrae by presentation of the longitudinal axis along an approach axis that is substantially along a plane of the intervertebral space and by insertion of the anchoring device through a receptacle in the intersomatic cage having dimensions and orientation adapted to the dimensions and radius of curvature of the anchoring device, with the anchoring device traversing at least a portion of the intersomatic cage; and
an instrument comprising
an impactor having an impactor head configured to push the anchoring device; and
an elongated guide having a gripping end and a push end, the guide comprising
a gripping device disposed at the gripping end and configured to grip the intersomatic cage, and
a guide head configured to at least partially accommodate the impactor head, the guide head comprising at least one guidance surface having a radius of curvature substantially the same as the radius of curvature of the anchoring device and configured to guide the anchoring device through a receptacle of the intersomatic cage.

25. The apparatus according to claim 24 in which the guide head further comprises a cavity configured to receive the anchoring device and, at least partially, the impactor head, and the guidance surface includes at least two curved grooves disposed along adjacent sides of the cavity.

26. The apparatus according to claim 25 in which the impactor comprises a rod slideable in relation to the guide and operable by a handle.

27. The apparatus according to claim 26 in which the impactor comprises a stop element configurable to limit travel of the impactor head with respect to the guide head.

28. The apparatus according to claim 27 in which the guidance surface is configured for a first end of the guidance surface to align with the receptacle of the intersomatic cage and for a second end of the guidance surface to be accessible for the insertion of the anchoring device.

29. The apparatus according to claim 28 in which the rod comprises a threaded end configured to engage a tapping in the intersomatic cage.

30. The apparatus according to claim 24 further comprising a rod slideable in a body of the guide and operable by a handle, and in which the gripping device comprises an end of the rod that is configured to engage a recess in the intersomatic cage.

31. An apparatus for implantation of a spinal implant comprising:
  an intersomatic cage configured for implantation in an intervertebral space between adjacent vertebrae of a spinal column, the intersomatic cage comprising:
    a peripheral wall; and
    a receptacle extending from a surface of the peripheral wall and traversing at least a portion of the peripheral wall, the receptacle configured with dimensions and orientation that are adapted
      to receive an anchoring device having an arcuate shape along a longitudinal axis that is configured for implantation in one of the vertebrae by presentation of the longitudinal axis along an approach axis that is substantially along a plane of the intervertebral space and
      to orient the anchoring device during implantation of the anchoring device in a vertebra;
  an anchoring device for anchoring the intersomatic cage between the adjacent vertebrae, the anchoring device comprising a body having an elongated shape along a longitudinal axis extending between a penetration end and an abutment end, the body having a curved shape along the longitudinal axis that describes an arc, and the body having dimensions and a radius of curvature configured for implantation of the anchoring device in one of the vertebrae by presentation of the longitudinal axis along an approach axis that is substantially along a plane of the intervertebral space and by insertion of the anchoring device through a receptacle in the intersomatic cage having dimensions and orientation adapted to the dimensions and radius of curvature of the anchoring device, with the anchoring device traversing at least a portion of the intersomatic cage; and
  an instrument comprising:
    an impactor having an impactor head configured to push the anchoring device; and
    an elongated guide having a gripping end and a push end, the guide comprising
      a gripping device disposed at the gripping end and configured to grip the intersomatic cage, and
      a guide head configured to at least partially accommodate the impactor head, the guide head comprising at least one guidance surface having a radius of curvature substantially the same as the radius of curvature of the anchoring device and configured to guide the anchoring device through a receptacle of the intersomatic cage.

32. The apparatus of claim 31 in which the body of the anchoring device includes at least one curved plate.

33. The apparatus of claim 32 in which the abutment end of the anchoring device comprises a stop element configured to mate with a surface of the implant.

34. The apparatus of claim 33 in which the stop element of the anchoring device comprises a projecting lug on a side of the body.

35. The apparatus of claim 34 in which the body of the anchoring device comprises a flexible lug disposed along a side of the body, the flexible lug orientated toward the abutment end and forming a stop.

36. The apparatus of claim 35 in which the receptacle of the intersomatic cage comprises a stop configured to mate with the flexible lug of the anchoring device to oppose withdrawal of the anchoring device from the receptacle.

37. The apparatus of claim 34 in which the receptacle of the intersomatic cage comprises a slot having a stop configured to mate with the projecting lug.

38. The apparatus of claim 37 in which the stop configured to mate with the projecting lug comprises a recess configured to accommodate the projecting lug.

39. The apparatus of claim 38, in which the body of the anchoring device comprises a flexible lug disposed along a side of the body, the flexible lug orientated toward the abutment end and forming a stop and the receptacle of the intersomatic cage comprises a stop configured to mate with the flexible lug of the anchoring device to oppose withdrawal of the anchoring device from the receptacle.

40. The apparatus of claim 33 in which the intersomatic cage comprises plural receptacles, at least one of which plural receptacles is configured for orientation of the anchoring device during implantation of the anchoring device in a first one of the adjacent vertebrae and at least one of which plural receptacles is configured for orientation of the anchoring device during implantation of the anchoring device in a second one of the adjacent vertebrae.

41. The apparatus according to claim 31 in which the guide head further comprises a cavity configured to receive the anchoring device and, at least partially, the impactor head, and the guidance surface includes at least two curved grooves disposed along adjacent sides of the cavity.

42. The apparatus according to claim 41 in which the impactor comprises a rod slideable in relation to the guide and operable by a handle.

43. The apparatus according to claim 42 in which the impactor comprises a stop element configurable to limit travel of the impactor head with respect to the guide head.

44. The apparatus according to claim 43 in which the guidance surface is configured for a first end of the guidance surface to align with the receptacle of the intersomatic cage and for a second end of the guidance surface to be accessible for the insertion of the anchoring device.

45. The apparatus according to claim 44 in which the rod comprises a threaded end configured to engage a tapping in the intersomatic cage.

46. The apparatus according to claim 31 further comprising a rod slideable in a body of the guide and operable by a handle, and in which the gripping device comprises an end of the rod that is configured to engage a recess in the intersomatic cage.

* * * * *